(12) United States Patent
Peled et al.

(10) Patent No.: US 8,455,450 B2
(45) Date of Patent: Jun. 4, 2013

(54) METHODS FOR OBTAINING A THERAPEUTICALLY EFFECTIVE AMOUNT OF HEMATOPOIETIC PRECURSOR CELLS AND LONG TERM ENGRAFTMENT THEREOF

(75) Inventors: Amnon Peled, Tel Aviv (IL); Michal Begin, Jerusalem (IL); Katia Beider, Jerusalem (IL); Michal Abraham, Mevaseret Zion (IL)

(73) Assignee: Biokine Therapeutics Ltd., Nes Ziona (IL)

( * ) Notice: Subject to any disclaimer, the term of this patent is extended or adjusted under 35 U.S.C. 154(b) by 707 days.

(21) Appl. No.: 12/520,699

(22) PCT Filed: Dec. 23, 2007

(86) PCT No.: PCT/IL2007/001596
§ 371 (c)(1),
(2), (4) Date: Nov. 18, 2009

(87) PCT Pub. No.: WO2008/075369
PCT Pub. Date: Jun. 26, 2008

(65) Prior Publication Data
US 2010/0166715 A1   Jul. 1, 2010

Related U.S. Application Data

(60) Provisional application No. 60/876,145, filed on Dec. 21, 2006.

(51) Int. Cl.
*C07K 7/08*   (2006.01)
*A61P 7/00*   (2006.01)
*A61K 38/10*  (2006.01)

(52) U.S. Cl.
USPC .................. 514/21.5; 514/13.5; 530/327

(58) Field of Classification Search
None
See application file for complete search history.

(56) References Cited

U.S. PATENT DOCUMENTS

| | | | |
|---|---|---|---|
| 4,179,337 | A | 12/1979 | Davis |
| 4,342,828 | A | 8/1982 | Takaku |
| 5,206,018 | A | 4/1993 | Sehgal et al. |
| 5,250,732 | A | 10/1993 | Kogan et al. |
| 5,492,126 | A | 2/1996 | Hennige et al. |
| 5,595,756 | A | 1/1997 | Bally et al. |
| 6,128,522 | A | 10/2000 | Acker et al. |
| 6,365,583 | B1 | 4/2002 | MacFarland |
| 6,576,875 | B1 | 6/2003 | Kleffner et al. |
| 6,875,738 | B1 | 4/2005 | Clark-Lewis |

(Continued)

FOREIGN PATENT DOCUMENTS

| | | |
|---|---|---|
| CA | 1297007 B1 | 3/1992 |
| EP | 169566 B2 | 1/1986 |

(Continued)

OTHER PUBLICATIONS

Wells (1990) Biochemistry 29(37): 8509-8517.*

(Continued)

*Primary Examiner* — Zachary Howard

(57) ABSTRACT

The present invention is directed to novel therapeutic uses of T-140 analog peptides and compositions comprising same. Specifically, the invention provides compositions and methods useful for providing improved bone marrow transplantation and in the treatment of other conditions wherein bone marrow depletion or suppression is involved.

2 Claims, 26 Drawing Sheets

U.S. PATENT DOCUMENTS

| | | | |
|---|---|---|---|
| 6,946,445 B1 | 9/2005 | Clark-Lewis et al. | |
| 7,138,488 B2 | 11/2006 | Fujii | |
| 7,169,750 B2 | 1/2007 | Bridger et al. | |
| 7,291,631 B2 | 11/2007 | Bridger | |
| 7,423,007 B2 | 9/2008 | Fujii et al. | |
| 7,595,298 B2 | 9/2009 | Fujii | |
| 7,630,750 B2 | 12/2009 | Liang et al. | |
| 8,017,585 B2 | 9/2011 | Fujii et al. | |
| 2002/0156034 A1 | 10/2002 | Tudan et al. | |
| 2004/0116655 A1 | 6/2004 | Fujii | |
| 2004/0209921 A1 | 10/2004 | Bridger et al. | |
| 2005/0002939 A1 | 1/2005 | Zlotnik et al. | |
| 2005/0043367 A1* | 2/2005 | Bridger et al. | 514/357 |
| 2006/0008465 A1 | 1/2006 | Steinaa | |
| 2006/0035829 A1 | 2/2006 | Bridger et al. | |
| 2006/0079492 A1 | 4/2006 | Ahlem et al. | |
| 2006/0264378 A1 | 11/2006 | Fujii et al. | |
| 2006/0264605 A1 | 11/2006 | Fujii | |
| 2007/0129760 A1 | 6/2007 | Demarais et al. | |
| 2007/0167459 A1 | 7/2007 | Habashita et al. | |
| 2009/0181897 A1 | 7/2009 | Fujii et al. | |
| 2010/0143334 A1 | 6/2010 | Peled et al. | |
| 2010/0166715 A1 | 7/2010 | Peled et al. | |
| 2010/0184694 A1 | 7/2010 | Peled et al. | |
| 2010/0222256 A1 | 9/2010 | Fujii | |
| 2011/0269686 A1 | 11/2011 | Fujii et al. | |
| 2012/0094907 A1 | 4/2012 | Abraham et al. | |
| 2012/0207748 A1 | 8/2012 | Peled et al. | |

FOREIGN PATENT DOCUMENTS

| | | |
|---|---|---|
| EP | 215126 B2 | 3/1987 |
| EP | 217404 B2 | 4/1987 |
| EP | 230980 B2 | 8/1987 |
| EP | 231819 B2 | 8/1987 |
| EP | 220520 B2 | 9/1987 |
| EP | 237545 B2 | 9/1987 |
| EP | 243153 A1 | 10/1987 |
| EP | 263490 B2 | 4/1988 |
| EP | 272703 B2 | 6/1988 |
| EP | 331186 B2 | 9/1989 |
| EP | 335423 B2 | 10/1989 |
| EP | 355811 B2 | 2/1990 |
| EP | 370205 B2 | 5/1990 |
| EP | 373679 B2 | 6/1990 |
| EP | 396158 A1 | 11/1990 |
| EP | 401384 B2 | 12/1990 |
| EP | 459516 A1 | 12/1991 |
| EP | 459630 B2 | 12/1991 |
| EP | 459795 B2 | 12/1991 |
| EP | 473268 B2 | 3/1992 |
| EP | 344796 B2 | 9/1994 |
| EP | 1323730 | 7/2003 |
| EP | 1541585 | 6/2005 |
| EP | 2058395 | 5/2009 |
| JP | 2002-506830 | 3/2002 |
| JP | 2002-247843 | 8/2002 |
| WO | 91/07988 A1 | 6/1991 |
| WO | 93/15211 A1 | 8/1993 |
| WO | WO 95/10534 | 4/1995 |
| WO | WO 99/47158 | 9/1999 |
| WO | 00/09152 A1 | 2/2000 |
| WO | WO 00/06086 | 2/2000 |
| WO | WO 00/09152 | 2/2000 |
| WO | WO 01/38352 | 5/2001 |
| WO | WO 01/64716 | 9/2001 |
| WO | 01/85196 A1 | 11/2001 |
| WO | WO 01/85196 | 11/2001 |
| WO | 02/20561 A1 | 3/2002 |
| WO | WO 02/20561 | 3/2002 |
| WO | 2004/020462 A1 | 3/2004 |
| WO | 2004/024178 A1 | 3/2004 |
| WO | WO 2004/020462 | 3/2004 |
| WO | WO 2004/024178 | 3/2004 |
| WO | 2004/087068 A1 | 10/2004 |
| WO | WO 2004/087068 | 10/2004 |
| WO | WO 2008/017025 | 2/2008 |
| WO | WO 2008/075369 | 6/2008 |
| WO | WO 2008/075370 | 6/2008 |
| WO | WO 2008/075371 | 6/2008 |
| WO | WO 2010/146578 | 12/2010 |
| WO | WO 2010/146584 | 12/2010 |
| WO | WO 2012/095849 | 7/2012 |

OTHER PUBLICATIONS

Ngo et al (1994) "The Protein Folding Problem and Tertiary Structure Prediction, Chapter 14: Computational Complexity Protein Structure Prediction, and the Levinthal Paradox" pp. 433-440 and 492-495 only.*

Bork (2000) Genome Research 10:398.*

Skolnick et al (2000) Trends in Biotech. 18(1): 34.*

Doerks et al (1998) Trends in Genetics 14(6): 248.*

Brenner (1999) Trends in Genetics 15(4): 132.*

AACR "97th Annual Meeting 2006: Publications", AACR, American Association fo Cancer Research, Retreived From the Internet, 2006.

Avniel et al. "Involvement of the CXCL12/CXCR4 Pathway in the Recovery of Skin Following Burns", Journal of Investigative Dermatology, 126(2): 468-476, 2006.

Balkwill "The Significance of Cancer Cell Expression of the Chemokine Receptor CXCR4", Seminars in Cancer Biology, 14: 171-179, 2004.

Broxmeyer et al. "Rapid Mobilization of Murine and Human Hematopoietic Stem and Progenitor Cells With AMD3100, A CXCR4 Antagonist", The Journal of Experimental Medicine, 201(8): 1307-1318, Apr. 18, 2005.

Dar et al. "Chemokine Receptor CXCR4-Dependent Internalization and Resecretion of Functional Chemokine SDF-1 by Bone Marrow Endothelial and Stromal Cells", Nature Immunology, 6(10): 1038-1046, Oct. 2005.

Darash-Yahana et al. "Role of High Expression Levels of CXCR4 in Tumor Growth, Vascularization, and Metastasis", The FASEB Journal, 18: 1240-1242, 2004.

Flomenberg et al. "The Use of AMD3100 Plus G-CSF for Autologous Hematopoietic Progenitor Cell Mobilization Is Superior to G-CSF Alone", Blood, 106(5): 1867-1874, 2005.

Kim et al. "In Vitro Behavior of Hematopoietic Progenitor Cells Under the Influence of Chemoattractants: Stromal Cell-DErived Factor-1, Steel Factor, and the Bone Marrow Environment", Blood, 91(1): 100-110, 1998.

Kollet et al. "Human CD34+CXCR4− Sorted Cells Harbor Intracellular CXCR4, Which Can Be Functionally Expressed and Provide NOD/SCID Repopulation", Blood, 100(8): 2778-2786, 2002.

Lack et al. "A Pharmacokinetic-Pharmacodynamic Model for the Mobilization of CD34+ Hematopoietic Progenitor Cells by AMD3100", Clinical Pharmacology and Therapeutics, 77(5): 427-436, 2005.

Lapidot et al. "How Do Stem Cells Find Their Way Home?", Blood, 106(6): 1901-1910, 2005.

Lapidot et al. "The Essential Roles of the Chemokine SDF-1 and Its Receptor CXCR4 in Human Stem Cell Homing and Repopulation of Transplanted Immune-Deficient NOD/SCID and NOD/SCID/B2m<Null> Mice", Leukemia, 16(10): 1992-2003, 2002.

Levesque et al. "Disruption of the CXCR4/CXCL12 Chemotactic Interaction During Hematopoietic Stem Cell Mobilization Induced by GCSF or Cyclophosphamide", Journal of Clinical Investigation, 111(2): 187-196, Jan. 2003.

Martin et al. "Chemokines Acting Via CXCR2 and CXCR4 Control the Release of Neutrophils From the Bone Marrow and Their Return Following Senescence", Immunity, 19(4): 583-593, Oct. 2003.

Mueller et al. "Involvement of Chemokine Receptors in Breast Cancer Metastasis", Nature, 410: 50-56, Mar. 2001.

Nagasawa et al. "Molecular Cloning and Structure of a Pre-B-Cell Growth-Stimulating Factor", Proc. Natl. Acad. sci. USA, 91: 2305-2309, Mar. 1994.

Peled et al. "Dependence of Human Stem Cell Engraftment and Repopulation of NOD/SCID Mice on CXCR4", Science, 283(5403): 845-848, 1999.

Phillips et al. "The Stromal Derived Factor-1/CXCL12-CXC Chemokine Receptor 4 Biological Axis in Non-Small Cell Lung Cancer Metastasis", 167: 1676-1686, 2003.

Princen et al. "HIV Chemokine Receptor Inhibitors as Novel Anti-HIV Drugs", Cytokine & Growth Factor Reviews, 16(6): 659-677, 2005.
Rossi et al. "The Biology of Chemokines and Their Receptors", Annual Reviews of Immunology, 18: 217-242, 2000.
Tamamura et al. "A Low-Molecular-Weight Inhibitor Against the Chemokine Receptor CXCR4: A Strong Anti-HIV Paptide T140", Biochemical and Biophysical Research Communications, 253(3): 877-882, 1998.
Tamamura et al. "Enhancement of the T140-Based Pharmacophores Leads to the Development of More Potent and Bio-Stable CXCR4 Antagonists", Organic Biomolecular Chemistry, 1: 3663-3669, 2003.
Tamamura et al. "The Therapeutic Potential of CXCR4 Antagonists in the Treatment of HIV Infection, Cancer Metastasis and Rheumatoid Arthritis", Expert Opinion of Therapeutic Targets, 9(6): 1267-1282, 2005.
Zannettino et al. "Elevated Serum Levels of Stromal-Derived Factor-1Alpha Are Associated With Increased Osteoclast Activity and Osteolytic Bone Disease in Multiple Myeloma Patients", Cancer Research, 65(5): 1700-1709, Mar. 1, 2005.
Zhou et al. "CXCR4 Is a Major Chemokine Receptor on Glioma Cells and Mediates Their Survival", The Journal of Biological Chemistry, 277(51): 49481-49487, Dec. 29, 2002.
Zuluaga et al. "Neutropenia Induced in Outbred Mice by a Simplified Low-Dose Cyclophosphamide Regimen: Characterization and Applicability to Diverse Experimental Models of Infectious Diseases", BMC Infectious Diseases, 6(55): 110, Mar. 17, 2006.
Restriction Official Action Dated Dec. 28, 2011 From the U.S. Appl. No. 12/520,803.
International Preliminary Report on Patentability Dated Jun. 24, 2009 From the International Bureau of WIPO Re. Application No. PCT/IL2007/001596.
International Preliminary Report on Patentability Dated Jun. 24, 2009 From the International Bureau of WIPO Re. Application No. PCT/IL2007/001598.
International Search Report and the Written Opinion Dated Jun. 4, 2008 From the International Searching Authority Re. Application No. PCT/IL2007/001598.
International Search Report and the Written Opinion Dated Dec. 5, 2008 From the International Searching Authority Re. Application No. PCT/IL2007/001596.
Respone Dated Jan. 4, 2012 to Office Action of Sep. 4, 2011 From the Israel Patent Office Re. Application No. 199468 and Its Translation Into English.
International Search Report and the Written Opinion Dated Jun. 24, 2009 From the International Searching Authority Re. Application No. PCT/IL2007/001597.
Esler et al. "Renal Sympathetic Denervation in Patients With Treatment-Resistant Hypertension (The Symplicity HTN-2 Trial): A Randomised Controlled Trial", The Lancet, 376: 1903-1909, Published Online Nov. 17, 2010.
Official Action Dated Mar. 5, 2012 From the U.S. Appl. No. 12/520,803.
Heredia et al. "Rapamycin Causes Down-Regulation of CCR5 and Accumulation of Anti-HIV Beta-Chemokines: An Approach to Suppress R5 Strains of HIV-1 ", Proc. Natl. Acad. Sci. USA, PNAS, 100(18): 10411-10416, Sep. 2, 2003.
Ulvatne et al. "Short Antibacterial Peptides and Erythromycin Act Synergically Against *Escherichia Coli*", Journal of Antimicrobial Chemotherapy, 48: 203-208, 2001.
Restriction Official Action Dated Mar. 28, 2012 From the U.S. Appl. No. 12/520,811.
Avniel S. et al., "Involvement of the CXCL12/CXCR4 Pathway in the Recovery of Skin Following Burns", J. Invest. Dermatol., 126(2):468-476 (2006).
Balkwill F., "The significance of cancer cell expression of the chemokine receptor CXCR4", Semin. in Canc. Biol., 14:171-179 (2004).
Broxmeyer H.E. et al., "Rabid mobilization of murine and human hematopoietic stem and progenitor cells with AMD3100, a CXCR4 antagonist", J. Exp. Med., 201(8)1307-1318 (2005).
Dar A. et al., "Chemokine receptor CXCR4-dependent internalization and resecretion of functional chemokine SDF-1 by bone marrow endothelial and stromal cells", Nat. Immunol. 6(10):1038-1046 (2005).
Flomenberg N. et al., "The use of AMD3100 plus G-CSF for autologous hematopoietic progenitor cell mobilization is superior to G-CSF alone", Blood, 106(5):1867-1874 (2005).
Kim C.H. et al., "In Vitro Behavior of Hematopoietic Progenitor Cells Under the Influence of Chemoattractants: Stromal Cell-Derived Factor-1, Steel Factor, and the Bone Marrow Environment", Blood, 91(1):100-110 (1998).
Kollet O. et al., "Human CD34+CXCR4− sorted cells harbor intracellular CXCR4, which can be functionally expressed and provide NOD/SCID repopulation", Blood, 100(8):2778-2786 (2002).
Lack N.A. et al., "A pharmacokinetic-pharmacodynamic model for the mobilization of CD34+ hematopoietic progenitor cells by AMD3100", Clin. Pharmacol. Ther., 77(5):427-436 (2005).
Lapidot T., et al., "The essential roles of the chemokine SDF-1 and its receptor CXCR4 in human stem cell homing and repopulation of transplanted immune-deficient NOD/SCID and NOD/SCID/B2mnull mice", Leukemia, 16(10):1992-2003 (2002).
Lapidot T. et al., "How do stem cells find their way home", Blood, 106(6):1901-1910 (2005).
Levesque J.P. et al., "Disruption of the CXCR4/CXCL12 chemotactic interaction during hematopoietic stem cell mobilization induced by GCSF or cyclophosphamide", J. Clin. Invest., 111(2):187-196 (Jan. 2003).
Martin C. et al., Chemokines Acting via CXCR2 and CXCR4 Control the Release of Neutrophils from the Bone Marrow and Their Return following Senescence, Immunity, 19(4):583-593 (Oct. 2003).
Muller A. et al.,"Involvement of chemokine receptors in breast cancer metastasis", Nature, 410:50-56 (Mar. 2001).
Nagasawa T. et al., "Molecular cloning and structure of a pre-B-cell growth-stimulating factor", Proc. Nat. Aca. Sci., 91:2305-2309 (Mar. 1994).
Peled A., et al., "Dependence of Human Stem Cell Engraftment and Repopulation of NOD/SCID Mice in CXCR4", Science, 283(5403):845-848 (1999).
Phillips R. J. et al., "The Stromal Derived Factor-1/CXCL12-CXC Chemokine Receptor 4 Biological Axis in Non-Small Cell Lung Cancer Metastases", Amer. J. Respir. Critic. Care Med., 167:1676-1686 (2003).
Princen K., et al., "HIV chemokine receptor inhibitors as novel anti-HIV drugs", Cytokine Grow. Fac. Rev., 16(6):659-677 (2005).
Rossi, D. et al., "The Biology of Chemokines and Their Receptors", Ann. Rev. Immun., 18:217-242 (2000).
Tamamura H. et al.,. "A Low-Molecular-Weight Inhibitor against the Chemokine Receptor CXCR4: A Strong Anti-HIV Peptide T140", Biochem. Biophys. Res. Commun., 253(3):877-882 (1998).
Tamamura H. et al., "Enhancement of the T140-based pharmacophores leads to the development of more potent and bio-stable CXCR4 antagonists", Org. Biomol. Chem., 1:3663-3669 (2003).
Tamamura H. et al., "T140analogs as CXCR4 antagonists identified as anti-matastatic agents in the treatment of breast cancer", FEBS letters. 550:79-83, published online Jul. 30, 2003.
Tamamura H. et al., "The therapeutic potential of CXCR4 antagonists in the treatment of HIV infection, cancer metastasis and rheumatoid arthritis", Expert Opin. Ther. Targets, 9(6):1267-1282 (2005).
Zuluaga A. F. et al. "Neutorpenia induced in outbred mice by a simplified low-dose cyclophosphamide regimen: characterization and applicability to diverse experimental models of infectious diseases", BMC Infect Dis., 6:55 (Mar. 17, 2006).
Requisition—Sequence Listing Dated Jan. 5. 2011 From the Canadian Intellectual Property Office Re. Application No. 2,673,719.
Response Dated Mar. 22, 2011 to Requisition—Sequence Listing of Jan. 5, 2011 From the Canadian Intellectual Property Office Re. Application No. 2,673,719.
Office Action Dated May 4, 2010 From the Israel Patent Office Re. Application No. 199468.
Office Action Dated May 4, 2010 From the Israel Patent Office Re. Application No. 199469.

Office Action Dated Sep. 4, 2011 From the Israel Patent Office Re. Application No. 199468 and Its Translation Into English.
Office Action Dated Oct. 31, 2011 From the Israel Patent Office Re. Application No. 199469 and Its Translation Into English.
Response Dated Oct. 21, 2010 to Office Action of May 4, 2010 From the Israel Patent Office Re. Application No. 199468.
Response Dated Oct. 21. 2010 to Office Action of May 4, 2010 From the Israel Patent Office Re. Application No. 199469.
Burger et al. "Small Peptide Inhibitors of the CXCR4 Chemokine Receptor (CD184) Antagonize the Activation, Migration, and Antiapoptotic Responses of CXCL12 in Chronic Lymphocytic Leukemia B Cells", Blood, 106(5): 1824-1830, Sep. 1, 2005.
Ghobrial et al. "Molecular Mechanisms Involved in Homing and Migration of Plasma Cells in Response to CXCR4", Blood, XP002629051, 104(11): 1-33, Apr. 12, 2005.
Menu et al. "The Involvement of Stromal Derived Factor 1Alpha in Homing and Progression of Multiple Myeloma in the 5TMM Model", Haematologica/The Hematology Journal, 91(5): 605-612, 2006.
Phillips et al. "Epidermal Growth Factor and Hypoxia-Induced Expression of CXC Chemokine Receptor 4 on Non-Small Cell Lung Cancer Cells Is Regulated by the Phosphatidylinositol 3-Kinase/PTEN/AKY/Mammalian Target of Rapamycin Signaling Pathway and Activation of Hypoxia Inducible Factor-1Alpha", The Journal of Biological Chemistry, 280(23): 22473-22481, 2005.
Ratajczak et al. "T140 Enhances G-CSF-Induced Mobilization of Hematopoietic Stem Cells", Experimental Hematology, 31: 154, Abstract #280, 2003.
Tamamura et al. "T140 Analogs as CXCR4 Antagonists Identified as Anti-Metastatic Agents in the Treatment of Breast Cancer", FEBS Letters, 550: 79-83, 2003.
Tsutsumi et al. "Therapeutic Potential of the Chemokine Receptor CXCR4 Antagonists as Multifunctional Agents", Biopolymers (Peptide Science), XP002629052, 88(2): 279-289, 2006.
Weekes et al. "Stromal Derived Factor1Alpha Mediates Resistance to mTOR Inhibition by the Preservation of Hypoxia Inducible Factor-1Alpha (HIF-1Alpha) Expression", Proceedings of the Annual Meeting of the American Association for Cancer Research, AACR, 47: 553, Abstract #2341, 2006.
Official Action Dated Jun. 25, 2012 From the US Patent and Trademark Office Re. U.S. Appl. No. 12/520,811.
Official Action Dated Sep. 10, 2012 From the US Patent and Trademark Office Re. U.S. Appl. No. 12/583,746.
Official Action Dated Sep. 12, 2012 From the US Patent and Trademark Office Re. U.S. Appl. No. 12/520,803.
Notice of Allowance Dated Dec. 10, 2012 From the US Patent and Trademark Office Re. U.S. Appl. No. 13/178,737.
Kucia et al. "Trafficking of Normal Stem Cells and Metastasis of Cancer Stem Cells Involve Similar Mechanisms: Pivotal Role of the SDF-1-CXCR4 Axis", Stem Cells, 23(7): 879-894, Aug. 2005.
Voerruans et al. "Migratory Behavior of Leukemic Cells From Acute Myeloid Leukemia Patients", Leukemia, 16(4): 650-657, Apr. 2002.
Supplementary European Search Report and the European Search Opinion Dated Jan. 3, 2013 From the European Patent Office Re. Application No. 10789103.8.
Amendment Dated May 15, 2008 After Notice of Allowance of Apr. 14, 2008 From the US Patent and Trademark Office Re. U.S. Appl. No. 10/525,838.
Communication Pursuant to Article 94(3) EPC Dated Oct. 4, 2010 From the European Patent Office Re. Application No. 03791288.8.
Communication Pursuant to Article 94(3) EPC Dated Apr. 9, 2008 From the European Patent Office Re. Application No. 03791288.8.
Communication Pursuant to Article 94(3) EPC Dated Dec. 15, 2008 From the European Patent Office Re. Application No. 03791288.8.
Communication Pursuant to Article 94(3) EPC Dated Sep. 15, 2009 From the European Patent Office Re. Application No. 03791288.8.
Communication Pursuant to Article 96(2) EPC Dated Feb. 6, 2006 From the European Patent Office Re. Application No. 10963414.6.
Communication Pursuant to Article 96(2) EPC Dated Mar. 17, 2005 From the European Patent Office Re. Application No. 10963414.6.
Communication Pursuant to Article 96(2) EPC Dated Jul. 18, 2006 From the European Patent Office Re. Application No. 10963414.6.

Communication Pursuant to Article 96(2) EPC Dated Jul. 26, 2007 From the European Patent Office Re. Application No. 10963414.6.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Mar. 12, 2012 From the European Patent Office Re. Application No. 10176632.7.
Communication Under Rule 71(3) EPC Dated Apr. 16, 2012 From the European Patent Office Re. Application No. 03791288.8.
European Search Report and the European Search Opinion Dated Feb. 3, 2012 From the European Patent Office Re. Application No. 10176632.7.
International Preliminary Report on Patentability Dated Apr. 19, 2002 From the International Preliminary Examining Authority Re. PCT/JP2001/007668.
International Preliminary Report on Patentability Dated Aug. 19, 2004 From the International Preliminary Examining Authority Re. Application No. PCT/JP2003/010753.
International Preliminary Report on Patentability Dated Dec. 29, 2011 From the International Bureau of WIPO Re. Application No. PCT/IL2010/000466.
International Search Report and the Written Opinion Dated Oct. 15, 2010 From the International Searching Authority Re. Application No. PCT/IL2010/000466.
International Search Report and the Written Opinion Dated May 30, 2012 From the International Searching Authority Re. Application No. PCT/IL2012/050008.
International Search Report Dated Nov. 4, 2003 From the International Searching Authority Re. Application No. PCT/JP2003/010753.
International Search Report Dated Dec. 11, 2001 From the International Searching Authority Re. Application No. PCT/JP2001/007668.
Interview Summary Dated May 3, 2005 From the US Patent and Trademark Office Re. U.S. Appl. No. 10/363,209.
Interview Summary Dated Feb. 21, 2006 From the US Patent and Trademark Office Re. U.S. Appl. No. 10/363,209.
Notice of Allowance Dated Mar. 9, 2006 From the US Patent and Trademark Office Re. U.S. Appl. No. 10/363,209.
Notice of Allowance Dated Apr. 11, 2011 From the US Patent and Trademark Office Re. U.S. Appl. No. 12/172,007.
Notice of Allowance Dated Apr. 14, 2008 From the US Patent and Trademark Office Re. U.S. Appl. No. 10/525,838.
Notice of Allowance DAted May 21, 2009 From the US Patent and Trademark Office Re. U.S. Appl. No. 11/497,225.
Official Action Dated Jul. 1, 2010 From the US Patent and Trademark Office Re. U.S. Appl. No. 12/172,007.
Official Action Dated Nov. 3, 2005 From the US Patent and Trademark Office Re. U.S. Appl. No. 10/363,209.
Official Action Dated Jul. 11, 2007 From the US Patent and Trademark Office Re. U.S. Appl. No. 10/525,838.
Official Action Dated Jun. 15, 2005 From the US Patent and Trademark Office Re. U.S. Appl. No. 10/363,209.
Official Action Dated May 18, 2012 From the US Patent and Trademark Office Re. U.S. Appl. No. 13/178,737.
Official Action Dated Jan. 24, 2011 From the US Patent and Trademark Office Re. U.S. Appl. No. 12/172,007.
Official Action Dated Aug. 28, 2008 From the US Patent and Trademark Office Re. U.S. Appl. No. 11/497,225.
Official Action Dated Dec. 28, 2011 From the US Patent and Trademark Office Re. U.S. Appl. No. 12/583,746.
Requisition by the Examiner Dated Jul. 6, 2012 From the Canadian Intellectual Property Office Re. Application No. 2,421,183.
Requisition by the Examiner Dated Mar. 8, 2011 From the Canadian Intellectual Property Office Re. Application No. 2,421,183.
Requisition by the Examiner Dated Oct. 17, 2011 From the Canadian Intellectual Property Office Re. Application No. 2,537,158.
Requisition by the Examiner Dated May 19, 2011 From the Canadian Intellectual Property Office Re. Application No. 2,421,183.
Requisition by the Examiner Dated Aug. 25, 2009 From the Canadian Intellectual Property Office Re. Application No. 2,421,183.
Requisition by the Examiner Dated May 25, 2010 From the Canadian Intellectual Property Office Re. Application No. 2,537,158.

Response Dated Jul. 1, 2005 to Communication Pursuant to Article 96(2) EPC of Mar. 17, 2005 From the European Patent Office Re. Application No. 10963414.6.
Response Dated Nov. 1, 2010 to Official Action of Jul. 1, 2010 From the US Patent and Trademark Office Re. U.S. Appl. No. 12/172,007.
Response Dated Feb. 3, 2006 to Official Action of Nov. 3, 2005 From the US Patent and Trademark Office Re. U.S. Appl. No. 10/363,209.
Response Dated Jun. 4, 2008 to Restriction Official Action of Apr. 8, 2008 From the US Patent and Trademark Office Re. U.S. Appl. No. 11/497,225.
Response Dated Sep. 7, 2011 to Requisition by the Examiner of Mar. 8, 2011 From the Canadian Intellectual Property Office Re. Application No. 2,421,183.
Response Dated Dec. 8, 2009 to Office Action of Aug. 11, 2009 From the Japanese Patent Office Re. Application No. 2003-301176.
Response Dated Jan. 8, 2008 to Official Action of Jul. 11, 2007 From the US Patent and Trademark Office Re. U.S. Appl. No. 10/525,838.
Response Dated May 9, 2006 to Communication Pursuant to Article 96(2) EPC of Feb. 6, 2006 From the European Patent Office Re. Application No. 10963414.6.
Response Dated Jun. 10, 2009 to Restriction Official Action of Mar. 26, 2009 From the US Patent and Trademark Office Re. U.S. Appl. No. 12/172,007.
Response Dated Oct. 12, 2010 to Communication Pursuant to Article 94(3) EPC of Oct. 4, 2010 From the European Patent Office Re. Application No. 03791288.8.
Response Dated Oct. 14, 2011 to Restriction Official Action of Sep. 14, 2011 From the US Patent and Trademark Office Re. U.S. Appl. No. 12/583,746.
Response Dated Apr. 15, 2009 to Communication Pursuant to Article 94(3) EPC of Dec. 15, 2008 From the European Patent Office Re. Application No. 03791288.8.
Response Dated Oct. 15, 2008 to Communication Pursuant to Article 94(3) EPC of Apr. 9, 2008 From the European Patent Office Re. Application No. 03791288.8.
Response Dated Sep. 15, 2005 to Official Action of Jun. 15, 2005 From the US Patent and Trademark Office Re. U.S. Appl. No. 10/363,209.
Response Dated Nov. 16, 2007 to Communication Pursuant to Article 96(2) EPC of Jul. 26, 2007 From the European Patent Office Re. Application No. 10963414.6.
Response Dated Apr. 18, 2005 to Restriction Official Action of Mar. 18, 2005 From the US Patent and Trademark Office Re. U.S. Appl. No. 10/363,209.
Response Dated Jan. 21, 2010 to Communication Pursuant to Article 94(3) EPC of Sep. 15, 2009 From the European Patent Office Re. Application No. 03791288.8.
Response Dated Mar. 23, 2011 to Official Action of Jan. 24, 2011 From the US Patent and Trademark Office Re. U.S. Appl. No. 12/172,007.
Response Dated Feb. 24, 2010 to Requisition by the Examiner of Aug. 25, 2009 From the Canadian Intellectual Property Office Re. Application No. 2,421,183.
Response Dated May 25, 2007 to Restriction Official Action of Feb. 6, 2007 From the US Patent and Trademark Office Re. U.S. Appl. No. 10/525,838.
Response Dated Nov. 25, 2011 to Requisition by the Examiner of May 25, 2010 From the Canadian Intellectual Property Office Re. Application No. 2,537,158.
Response Dated Jan. 26, 2009 to Official Action of Aug. 28, 2008 From the US Patent and Trademark Office Re. U.S. Appl. No. 11/497,225.
Response Dated Jan. 29, 2007 to Communication Pursuant to Article 96(2) EPC of Jul. 18, 2006 From the European Patent Office Re. Application No. 10963414.6.
Response Dated Jun. 30, 2010 to Requisition by the Examiner of May 19, 2011 From the Canadian Intellectual Property Office Re. Application No. 2,421,183.
Response Dated Jan. 31, 2011 to Office Action of Oct. 19, 2010 From the Japanese Patent Office Re. Application No. 2003-301176.
Restriction Official Action Dated Feb. 6, 2007 From the US Patent and Trademark Office Re. U.S. Appl. No. 10/525,838.
Restriction Official Action Dated Apr. 8, 2008 From the US Patent and Trademark Office Re. U.S. Appl. No. 11/497,225.
Restriction Official Action Dated Sep. 14, 2011 From the US Patent and Trademark Office Re. U.S. Appl. No. 12/583,746.
Restriction Official Action Dated Feb. 16, 2012 From the US Patent and Trademark Office Re. U.S. Appl. No. 13/178,737.
Restriction Official Action Dated Mar. 18, 2005 From the US Patent and Trademark Office Re. U.S. Appl. No. 10/363,209.
Restriction Official Action Dated Mar. 26, 2009 From the US Patent and Trademark Office Re. U.S. Appl. No. 12/172,007.
Second Amendment Dated Jul. 14, 2008 to Amendment of May 15, 2008 After Notice of Allowance of Apr. 14, 2008 From the US Patent and Trademark Office Re. U.S. Appl. No. 10/525,838.
Supplementary European Search Report Dated Nov. 19, 2004 From the European Patent Office Re. Application No. 01963414.6.
Supplementary Partial European Search Report Dated Nov. 28, 2007 From the European Patent Office Re. Application No. 03791288.8.
Translation of Office Action Dated Aug. 11, 2009 From the Japanese Patent Office Re. Application No. 2003-301176.
Translation of Office Action Dated Oct. 19, 2010 From the Japanese Patent Office Re. Application No. 2003-301176.
Arakaki et al. "T134, A Small-Molecule CXCR4 Inhibitor, Has No Cross-Drug Resistance With AMD3100, a CXCR4 Antagonist With a Different Structure", Journal of Virology, XP002199036, 73(2): 1719-1723, Feb. 1999.
Auerbach et al. "Angiogenesis Assays: Problems, Pitfalls and Potential", Cancer and Metastasis Reviews, 19: 167-172, 2000.
Di Cesare et al. "In Vitro Characterization and Inhibition of the CXCR4/CXCL12 Chemokine Axis in Human Uveal Melanoma Cell Lines", Cancer Cell International, XP021036445, 7(17): 1-8, Nov. 14, 2007. Abstract, Last Para, Title, P.5, Right Col., Last Para.
Fransen et al. "Suppression of Dualtropic Human Immunodeficiency Virus Type 1 by the CXCR4 Antagonist AMD3100 is Associated With Efficiency of CXCR4 Use and Baseline Virus Composition", Antimicrobial Agents and Chemotherapy, 52(7): 2608-2615, Apr. 28, 2008.
Fujii.
Fujii et al. "Peptide-Lead CXCR4 Antagonists With High Anti-HIV Activity", Current Opinion in Investigational Drugs, 2(9): 1198-1202, 2001.
Gotoh et al. "Increase of R5 HIV-1 Infection and CCR5 Expression in T Cells Treated With High Concentrations of CXCR4 Antagonists and SDF-1", Journal of Infection and Chemotherapy, 7(1): 28-36, 2001.
Gura "Cancer Models: Systems for Identifying New Drugs Are Often Faulty", Science, 278(5340): 1041-1042, Nov. 7, 1997.
Hatse et al. "CXC-ChemokineReceptor 4 as a Potential New Therapeutic Target for Neuroblastoma and Breast Cancer", International Journal of Cancer, XP001156644, Supplement, 13: 349, Abstract # p. 669, Jul. 2002.
Hendrix et al. "Safety, Pharmacokinetics, and Antiviral Activity of AMD3100, a Selective CXCR4 Receptor Inhibitor, in HIV-1 Infection", Journal of Aquired Immune Deficiency Syndromes, JAIDS, 37(2): 1253-1261, Oct. 1, 2004.
Hesselgesser et al. "Neuronal Apoptosis Induced by HIV-1 Gp120 and the Chemokine SDF-1Alpha Is Mediated by the Chemokine Receptor CXCR4", Current Biology, 8: 595-598, Apr. 27, 1998.
Hiramatsu et al. "Synthesis of CXCR4 Antagonists, T140 Derivatives With Improved Biostability, and Their SAR Study", Peptide Science, XP009092185, 203: 213-216, 2002. Abstract, Fig.1.
Jain "Barriers to Drug Delivery in Solid Tumors. Many Tumors Resist Full Penetration by Anticancer Agents. Such Resistance May Help Explain Why Drugs That Eradicate Tumor Cells in Laboratory Dishes Often Fail to Eliminate Malignancies in the Body", Scientific American, p. 58-65, Jul. 1994.
Koshiba et al. "Expression of Stromal Cell-Derived Factor 1 and CXCR4 Ligand Receptor System in Pancreatic Cancer: A Possible Role for Tumor Progression", Clinical Cancer Research, 6(9): 3530-3535, Sep. 2000.
Matthys et al. "AMD3100, a Potent and Specific Antagonist of the Stromal Cell-Derived Factor-1 Chemokine Receptor CXCR4, Inhibits Autoimmune Joint Inflammation in IFN-Gamma Receptor-Deficient Mice", The Journal of Immunology, 167(8): 4686-4692, 2001.

Merck "Clinical Aspects of Cancer", The Merck Manual, Jun. 26, 2007.

Merck "Introduction: Overview of Cancer", The Merck Manual, Jun. 26, 2007.

Merck "Rheumatoid Arthritis (RA)", The Merck Manual, 18th Ed., 2005.

Mori et al. "Involvement of Stromal Cell-Derived Factor 1 and CXCR4 Receptor System in Pancreatic Cancer", Gastroenterology, XP009021758, 122(4/Suppl.1): A490, Abstract #T1608, Apr. 2002.

Nakashima et al. "Anti-Human Immunodeficiency Virus Activity of a Novel Synthetic Peptide, T22 ([Tyr-5,12, Lys-7]Polyphemusin II): A Possible Inhibitor of Virus-Cell Fusion", Antimicrobial Agents and Chemotherapy, 36(6): 1249-1255, Jun. 1992.

Neidl "Failure Modes in the Discovery Process", Cancer Drug Design and Discovery, Chap.18.2.2: 427-431, 2008.

Omagari et al. "Development of Specific CXCR4 Inhibitors Based on an Anti-HIV Peptide, T140, and Their Structure-Activity Relationships Study", Peptide Science, 2000(37): 129-132, 2001.

Sporn et al. "Chemoprevention of Cancer", Carcinogenesis, 21(3): 525-530, 2000.

Tamamura "Development of Selective Antagonists Against an HIV Second Receptor", Yakugaku Zasshi, 121(11): 781-792, 2001. Abstract in English.

Tamamura et al. "A Future Perspective on the Development of Chemokine Receptor CXCR4 Antagonists", Database EMBASE [Online], XP002675634, Database Accession No. EMB-2008509452, Oct. 2008. & Expert Opinion on Drug Discovery, 3(10): 1155-1166, Oct. 2008.

Tamamura et al. "A Low-Molecular-Weight Inhibitor Against the Chemokine Receptor CXCR4: A Strong Anti-HIV Peptide T140", Biochemic and Biophysical Research Communications, XP002169961, 253(3): 877-882, Jan. 1, 1998. Abstract, Fig.1.

Tamamura et al. "A Low-Molecular-Weight Inhibitor Against the Chemokine Receptor CXCR4: A Strong Anti-HIV Peptide T140", Biochemical and Biophysical Research Communications, 253(3): 877-882, 1998.

Tamamura et al. "Certification of the Critical Importance of L-3-(2-Naphtyl)Alanine at Position 3 of a Specific CXCR4 Inhibitor, T140, Leads to an Exploratory Performance of Its Downsizing Study", Bioorganic & Medicinal Chemistry, 10: 1417-1426, 2002.

Tamamura et al. "Development of Specific CXCR4 Inhibitors Possessing High Selectivity Indexes as Well as Complete Stability in Serum Based on an Anti-HIV Peptide T140", Bioorganic & Medicinal Chemistry Letters, XP002265743, 11(14): 1897-1902, Jul. 23, 2001. Abstract, Fig.1, p. 1901, r-h Col., Last Sentence Before 'Acknowledgements'.

Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, 6: 473-479, 1998.

Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, XP002458598, 6(4): 473-479, Apr. 1998. Abstract, Fig.1.

Tamamura et al. "Effective Lowly Cytotoxic Analogs of an HIV-Cell Fusion Inhibitor, T22 ([Tyr5,12, Lys7]-Polyphemusin II)", Bioorganic & Medicinal Chemistry, 6(2): 231-238, 1998.

Tamamura et al. "Effective Lowly Cytotoxic Analogs of an HIV-Cell Fusion Inhibitor, T22 ([Tyr5,12, Lys7]-Polyphemusin II)", Bioorganic & Medicinal Chemistry, XP002906341, 6(2): 231-238, Jan. 1, 1998. Abstract, Fig.1.

Tamamura et al. "Efficient Analogs of an Anti-HIV Peptide, T22 ([Tyr5,12, Lys7]-Polyphemusin II), Having Low Cytotoxicity", Peptide Science—Present and Future, Proceedings of the 1st International Peptide Symposium, XP002973954, 1997: 427-429, Jan. 1, 1999. Abstract, Fig.2.

Tamamura et al. "HIV-Cell Fusion Inhibitors Targeted to the HIV Second Receptor: T22 and Its Downsized Analogs With High Activity", Peptide Science, 1998(35): 49-52, 1999.

Tamamura et al. "Pharmacophore Identification of a Specific CXCR4 Inhibitor, T140, Leads to Development of Effective Anti-HIV Agents With Very High Selectivity Indexes", Bioorganic & Medicinal Chemistry Letters, 10(23): 2633-2637, 2000.

Tamamura et al. "T140 Analogs as CXCR4 Antagonists Identified as Anti-Metastatic Agents in the Treatment of Breast Cancer", FEBS Letters, XP004448372, 550: 79-83, Aug. 28, 2003.

* cited by examiner

METHODS FOR OBTAINING A THERAPEUTICALLY EFFECTIVE AMOUNT OF HEMATOPOIETIC PRECURSOR CELLS AND LONG TERM ENGRAFTMENT THEREOF

RELATED APPLICATION DATA

This application is the U.S. national stage of PCT/IL2007/001596 filed on Dec. 23, 2007, which claims priority to and benefit of U.S. Provisional Patent Application No. 60/876,145 filed on Dec. 21, 2006, the content of each of which is expressly incorporated herein in its entirety by reference hereto.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 47,627 byte ASCII (text) file named "Seq_List" created on Jun. 22, 2009.

FIELD OF THE INVENTION

The present invention is directed to compositions comprising T-140 peptide analogs having CXCR4 super-agonist activity and to novel therapeutic uses thereof in modulating recovery of the hematopoietic system, particularly in the treatment of conditions associated with damage to the bone marrow.

BACKGROUND OF THE INVENTION

Chemokines, a family of small pro-inflammatory cytokines, and their receptors, regulate a variety of immune responses to infection, inflammation and tissue repair. Chemokines are divided between two major families on the basis of relative position of cysteine residues in the mature protein (C—C and C—X—C). Primarily, they are responsible for the directional migration, or chemotaxis, of lymphocytes to specific lymphoid tissues, and the recruitment of leukocytes to the sites of infection or tissue damage. In addition to their chemotactic function, chemokines are implicated in other biological events including embryogenesis, lymphopoiesis, vascularization, and HIV pathogenesis. More recently, it has been established that cancer cells exploit signaling through chemokine receptors for several key steps involved in initiation and progression of primary and metastatic cancer. Different types of cancers express different CC and CXC chemokine receptors. There is one chemokine receptor, however, that appears to be expressed by the majority of cancer types, namely, CXCR4.

The CXCR4/CXCL12 Axis

The chemokine receptor CXCR4 is a G-protein coupled receptor that is expressed in a wide assortment of normal tissues, and plays a fundamental role in fetal development, mobilization of hematopoietic stem cells and trafficking of naive lymphocytes (Rossi and Zlotnik, 2000). Besides normal tissues, CXCR4 appears to be expressed by at least 23 different epithelial, mesenchymal and hematopoietic cancers, including prostate cancer, and acute and chronic myeloid leukemias (Balkwill, 2004). The chemokine CXCL12 (also known as stromal-derived factor-1, or SDF-1) is CXCR4's only natural ligand. CXCL12 is expressed constitutively in a variety of tissues, including lung, liver, bone marrow and lymph nodes. These organs with highest expression of CXCL12 correlate with common metastatic destinations in many cancers. The chemokine receptor, CXCR4, and its ligand, CXCL12, appear to be an important chemokine axis regulating tumor growth and metastasis (Nagasawa, et al., 1994; Muller et al., 2001; Phillips, et al., 2003).

Binding of CXCL12 to CXCR4 activates a variety of intracellular signal transduction pathways and effector molecules that regulate cell chemotaxis, adhesion, survival, and proliferation. There are a number of key molecules that mediate signaling through CXCR4, and some of them will be described below.

CXCL12 and CXCR4 stimulate the phosphatidyl-inositol-3-kinase pathway that subsequently activates the protein kinase, Akt. Activated Akt phosphorylates a variety of intracellular targets, functioning to inhibit apoptosis and prolonging survival in different types of cancer cells. Beyond cell survival, Akt has also been implicated in effects of CXCR4 on migration of cells toward CXCL12 and their proliferation.

The mitogen-activated protein (MAP) kinase pathway is another signal transduction pathway regulated by CXCR4. Following stimulation with CXCL12, CXCR4 activates the kinase MEK, which in turn activates ERK1/2 MAP kinases. Activated ERK1/2 kinases phosphorylate transcription factors such as Elk-1; this process increases expression of genes that promote survival and proliferation of cancer cells.

CXCR4 also appears to regulate angiogenesis, the process that is important for both normal physiology and growth of tumors. Mice lacking CXCR4 or CXCL12 have defective formation of blood vessels in the gastrointestinal tract. Proangiogenic effect of CXCR4 signaling may be mediated through up-regulation of vascular-endothelial growth factor (VEGF). Thus, another potential function of CXCR4 signaling in tumor development is promotion of blood vessel production.

The CXCR4/CXCL12 Axis in Hematopoietic Stem Cell Mobilization

All mature blood cells are derived from hematopoietic stem cells (HSC) through intermediates that are termed hematopoietic progenitor cells (HPCs). Hematopoietic cells at various stages of differentiation are localized within the bone marrow (BM), their main site of production. Their mobilization between BM and blood is a physiological process, but under steady-state conditions HPCs and HSCs circulate in the blood at frequencies too low to allow for efficient collection of numbers sufficient to transplantation. Recently, the use of peripheral blood as source of HSCs for transplantations has replaced bone marrow as the preferred source of hematopoietic rescue. Stem cell frequencies in blood are considerably increased both in responses to various growth factors and during the recovery phase following myelosuppressive chemotherapy. Increased number of hematopoietic cells in the blood and amelioration of their mobilization ability will improve the efficiency of transplantation and will shorten the time of cytopenia and engraftment.

Granulocyte Colony-stimulating Factor (G-CSF)-mobilized peripheral-blood mononuclear cells are routinely used as a source of hematopoietic stem cells for transplantation. However, this mobilization results in broad inter-individual variations in circulating progenitor cell numbers. Thus, optimal methods to mobilize and collect peripheral-blood progenitor cells for hematopoietic rescue still need to be found.

Over recent years it has become apparent that the interaction between CXCL12 and its receptor, CXCR4, plays pivotal role in mobilization and engraftment of hematopoietic cells (Kollet et al., 2002; Lapidot et al., 2002; Levesque et al., 2003; Peled et al., 1999; Lapidot et al., 2005; Dar et al., 2005).

The CXCR4 receptor is widely expressed on many cell types including HSCs and HPCs and the interaction with its ligand seems to be involved in their chemotaxis, homing and survival. The CXCL12/CXCR4 axis was found to be involved in the retention of hematopoietic cells within the bone marrow microenvironment (Kim et al., 1998) and consequently, it was suggested that antagonizing the interactions of marrow-produced CXCL12 with CXCR4 expressed on HSCs might be an effective HSC mobilizing strategy.

CXCR4 Modulators and T-140 Analogs

Various uses of chemokine receptor modulators, including CXCR4 agonists and antagonists, have been described in the art (Princen et al., 2005; Tamamura et al., 2005). For example, the bicyclam drug termed AMD3100, originally discovered as an anti-HIV compound, specifically interacts with CXCR4 in an antagonistic manner. Blocking CXCR4 receptor with AMD3100 results in the mobilization of hematopoietic progenitor cells; when combining AMD3100 with G-CSF, additive effects were detected (Flomenberg et al., 2005; Broxmeyer et al., 2005). AMD3100 is currently undergoing clinical trials to evaluate its ability to increase stem cells available for transplant (Lack et al., 2005). U.S. Pat. No. 6,365,583 discloses a method to treat a subject who would be benefited by elevation of white blood cell count which method comprises administering to said subject a cyclic polyamine such as AMD3100. Martin et al. (2003) show that the mobilization of neutrophils from the bone marrow by the CXCR2-chemokine, KC, was enhanced by AMD3100, examined 60 minutes after administration to normal BALB/c mice.

U.S. Patent Application Publication No. 2004/0209921 discloses heterocyclic compounds that bind to chemokine receptors, including CXCR4 and CCR5, which may possess protective effects against infection of target cells by a human immunodeficiency virus (HIV). Other potential uses for these compounds suggested by '921 are enhancing the population of progenitor and/or stem cells, stimulating the production of white blood cells, and/or effecting regeneration of cardiac tissue.

U.S. Pat. No. 6,946,445 discloses CXCR4 antagonists comprising the sequence KGVSLSYR. The antagonists disclosed by the '445 patent are suggested to be potentially useful for reducing interferon gamma production by T-cells, treatment of an autoimmune disease, treatment of multiple sclerosis, treatment of other neurological diseases, treatment of cancer, and regulation of angiogenesis. U.S. Pat. No. 6,875,738 discloses methods for treating a solid tumor in a mammal and for inhibiting angiogenesis in a mammal using these antagonists.

U.S. Patent Application Publication No. 2005/0002939 discloses a method of treating ovarian cancer in a mammal, the method comprising administering to the mammal a therapeutically effective dose of a CXCR4 inhibitor. The '939 application suggests that an anti-CXCR4 antibody may impact the survival or growth of a CXCR4-expressing tumor derived from a bladder tumor cell line in a mouse model.

T-140 is a 14-residue synthetic peptide developed as a specific CXCR4 antagonist that suppress HIV-1 (X4-HIV-1) entry to T cells through specific binding to CXCR4 (Tamamura et al., 1998). Subsequently, peptide analogs of T-140 were developed as specific CXCR4 antagonist peptides with inhibitory activity at nanomolar levels (see Tamamura et al., 2003, WO 2002/020561 and WO 2004/020462).

WO 2002/020561 discloses novel peptide analogs and derivatives of T-140. The '561 publication demonstrates that the claimed peptides are potent CXCR4 inhibitors, manifesting high anti-HIV virus activity and low cytotoxicity.

WO 2004/020462 discloses additional novel peptide analogs and derivatives of T-140, including 4F-benzoyl-TN14003 (SEQ ID NO:1). The '462 publication further discloses novel preventive and therapeutic compositions and methods of using same utilizing T-140 analogs for the treatment of cancer and chronic rheumatoid arthritis. The specification of '462 demonstrates the ability of these peptides to inhibit cancer cell migration, including breast cancer and leukemia cells, and to inhibit metastasis formation in vivo. Further demonstrated therein is inhibition of delayed-type hypersensitivity reaction in mice and collagen-induced arthritis, an animal model of rheumatoid arthritis.

WO 2004/087068 is directed to a method for treating or preventing a CXCR4 mediated pathology comprising administering a CXCR4 peptide antagonist to a host in an amount sufficient to inhibit CXCR4 signal transduction in a cell expressing a CXCR4 receptor or homologue thereof, wherein the CXCR4 peptide antagonist is not an antibody or fragment thereof. The '068 publication discloses that exemplary CXCR4 peptide antagonists include T140 and derivatives of T140, and that the pathology includes cancer such as breast, brain, pancreatic, ovarian, prostate, kidney, and non-small lunch cancer. Other publications directed to the use of CXCR4 antagonists in cancer therapy include, for example, WO 00/09152, US 2002/0156034, and WO 2004/024178.

WO 01/85196 suggests that hematopoietic cell proliferation may be modulated by ex vivo exposure to CXCR4 antagonists derived from SDF-1 (P2G), in which glycine is substituted for proline at amino acid position 2.

A recent publication by some of the inventors of the present invention (Avniel et al., 2006) discloses that blocking the CXCR4/CXCL12 axis by a T-140 analog resulted in a significant reduction in eosinophil accumulation in the dermis and improved epithelialization, thus significantly improving skin recovery after burns.

None of the prior art discloses or suggests that CXCR4 inhibitor peptides belonging to the T-140 analog family may also affect CXCR4 activity in an agonist manner. There exists a long felt need for compositions and methods useful for modulating CXCR4-mediated processes involved in pathological conditions in vivo.

SUMMARY OF THE INVENTION

The present invention is directed to novel therapeutic applications of T-140 analog peptides. The present invention discloses, for the first time, that T-140 analogs, hitherto known as CXCR4 inhibitors, unexpectedly also possess CXCR4 superagonistic properties. The present invention thus provides compositions and methods utilizing T-140 analogs in applications in which activation of CXCR4 in an agonistic manner is beneficial, such as for modulating hematopoietic precursor and mature cells in the blood and within the bone marrow.

The instant invention is based, in part, on the surprising discovery that the known T-140 analog 4F-benzoyl-TN14003 (4F-benzoyl-Arg-Arg-NaI-Cys-Tyr-Cit-Lys-DLys-Pro-Tyr-Arg-Cit-Cys-Arg-NH$_2$, SEQ ID NO:1) demonstrates a qualitatively and quantitatively distinct mobilization pattern of white blood cells and hematopoietic progenitor cells from the bone marrow into blood circulation, compared to the response induced by the bicyclam CXCR4 inhibitor AMD3100. 4F-benzoyl-TN14003 was significantly more potent in mobilizing selectively hematopoietic progenitor cells and stem cells, when administered either alone or in combination with G-CSF; the cell populations mobilized by 4F-benzoyl-TN14003 and AMD3100 were also qualitatively distinct, and cells mobilized by 4F-benzoyl-TN14003 were markedly more efficient in rescuing lethally-irradiated mice than were cells mobilized by AMD3100, when equal amounts of blood from AMD3100 and 4F-benzoyl-TN14003 treated mice were administered to recipient mice.

In addition, 4F-benzoyl-TN14003 was surprisingly found to induce proliferation of hematopoietic progenitor cells and to enhance the formation of mature hematopoietic cells in the bone marrow of lethally irradiated mice; AMD3100 did not demonstrate such effects.

The present invention provides compositions and methods using 4F-benzoyl-TN14003 or other peptides of the T-140 analog family, useful for improving the efficiency and safety of stem cell transplantation, for enhancing the recovery of the bone marrow following chemotherapy and irradiation and for treating patients having impaired peripheral blood white blood cell counts, as detailed herein.

Thus, according to a first aspect of the present invention, there is provided a method for elevating the levels of at least one type of hematopoietic cells in a subject comprising administering to the subject an effective amount of a peptide having an amino acid sequence as set forth in SEQ ID NO:1 or an analog or derivative thereof.

The 4F-benzoyl-TN14003 analogs and derivatives used in the novel compositions and methods of the invention are the structurally and functionally related peptides disclosed in patent applications WO 2002/020561 and WO 2004/020462, also known as "T-140 analogs", as detailed hereinbelow.

In various particular embodiments, the analog or derivative has an amino acid sequence as set forth in the following formula (I) or a salt thereof:

(I)
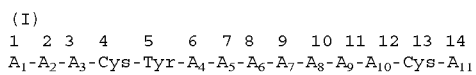
$A_1$-$A_2$-$A_3$-Cys-Tyr-$A_4$-$A_5$-$A_6$-$A_7$-$A_8$-$A_9$-$A_{10}$-Cys-$A_{11}$ wherein:
 $A_1$ is an arginine, lysine, ornithine, citrulline, alanine or glutamic acid residue or a N-α-substituted derivative of these amino acids, or $A_1$ is absent;
 $A_2$ represents an arginine or glutamic acid residue if $A_1$ is present, or $A_2$ represents an arginine or glutamic acid residue or a N-α-substituted derivative of these amino acids if $A_1$ is absent;
 $A_3$ represents an aromatic amino acid residue;
 $A_4$, $A_5$ and $A_9$ each independently represents an arginine, lysine, ornithine, citrulline, alanine or glutamic acid residue;
 $A_6$ represents a proline, glycine, ornithine, lysine, alanine, citrulline, arginine or glutamic acid residue;
 $A_7$ represents a proline, glycine, ornithine, lysine, alanine, citrulline or arginine residue;
 $A_8$ represents a tyrosine, phenylalanine, alanine, naphthylalanine, citrulline or glutamic acid residue;
 $A_{10}$ represents a citrulline, glutamic acid, arginine or lysine residue;
 $A_{11}$ represents an arginine, glutamic acid, lysine or citrulline residue wherein the C-terminal carboxyl may be derivatized;
and the cysteine residue of the 4-position or the 13-position can form a disulfide bond, and the amino acids can be of either L or D form.

Exemplary peptides according to formula (I) are peptides having an amino acid sequence as set forth in any one of SEQ ID NOS:1-72, as presented in Table 1 hereinbelow.

In another preferable embodiment, the analog or derivative has an amino acid sequence as set forth in SEQ ID NO:65 (H-Arg-Arg-Nal-Cys-Tyr-Cit-Lys-DLys-Pro-Tyr-Arg-Cit-Cys-Arg-OH; TC14003).

In certain other particular embodiments, said analog or derivative is selected from the group consisting of:

(SEQ ID NO: 1)
4F-bezoyl-Arg-Arg-Nal-Cys-Tyr-Cit-Lys-DLys-Pro-Tyr-Arg-Cit-Cys-Arg-NH₂, (SEQ ID NO: 2)
Ac-Arg-Arg-Nal-Cys-Tyr-Cit-Lys-DLys-Pro-Tyr-Arg-Cit-Cys-Arg-OH, (SEQ ID NO: 3)
Ac-Arg-Arg-Nal-Cys-Tyr-Arg-Lys-DCit-Pro-Tyr-Arg-Cit-Cys-Arg-OH, (SEQ ID NO: 4)
Ac-Arg-Arg-Nal-Cys-Tyr-Cit-Lys-DCit-Pro-Tyr-Arg-Cit-Cys-Arg-OH, (SEQ ID NO: 10)
Ac-Arg-Arg-Nal-Cys-Tyr-Cit-Lys-DCit-Pro-Tyr-Arg-Cit-Cys-Arg-NH₂, (SEQ ID NO: 46)
TMguanyl-Arg-Arg-Nal-Cys-Tyr-Cit-Lys-DCit-Pro-Tyr-Arg-Cit-Cys-Arg-NH₂;, (SEQ ID NO: 47)
Aca-Arg-Arg-Nal-Cys-Tyr-Cit-Lys-DCit-Pro-Tyr-Arg-Cit-Cys-Arg-NH₂, (SEQ ID NO: 51)
Ac-Arg-Arg-Nal-Cys-Tyr-Cit-Lys-DLys-Pro-Tyr-Arg-Cit-Cys-Arg-NH₂, (SEQ ID NO: 52)
Ac-Arg-Arg-Nal-Cys-Tyr-Arg-Lys-DCit-Pro-Tyr-Arg-Cit-Cys-Arg-NH₂, (SEQ ID NO: 53)
4F-benzoyl-Arg-Arg-Nal-Cys-Tyr-Cit-Lys-DGlu-Pro-Tyr-Arg-Cit-Cys-Arg-NHMe, (SEQ ID NO: 54)
4F-benzoyl-Arg-Arg-Nal-Cys-Tyr-Cit-Lys-DGlu-Pro-Tyr-Arg-Cit-Cys-Arg-NHEt (SEQ ID NO: 55)
4F-benzoyl-Arg-Arg-Nal-Cys-Tyr-Cit-Lys-DGlu-Pro-Tyr-Arg-Cit-Cys-Arg-NHiPR, (SEQ ID NO: 56)
4F-benzoyl-Arg-Arg-Nal-Cys-Tyr-Cit-Lys-DGlu-Pro-Tyr-Arg-Cit-Cys-Arg-tyramine, (SEQ ID NO: 65)
H-Arg-Arg-Nal-Cys-Tyr-Cit-Lys-DLys-Pro-Tyr-Arg-Cit-Cys-Arg-OH, (SEQ ID NO: 66)
H-Arg-Arg-Nal-Cys-Tyr-Cit-Lys-DLys-Pro-Tyr-Arg-Cit-Cys-Arg-NH₂, (SEQ ID NO: 68)
H-Arg-Arg-Nal-Cys-Tyr-Cit-Lys-DLys-Pro-Tyr-Arg-Cit-Cys-Arg-NH₂, (SEQ ID NO: 70)
H-Arg-Arg-Nal-Cys-Tyr-Cit-Lys-DLys-Pro-Tyr-Arg-Cit-Cys-Arg-OH,
and (SEQ ID NO: 71)
H-Arg-Arg-Nal-Cys-Tyr-Cit-Lys-DLys-Pro-Tyr-Arg-Cit-Cys-Arg-OH.

According to some embodiments, the T-140 peptide analogs of the invention are herein demonstrated to be superior to other mobilizing agents, including known CXCR4 modulators (such as CXCR4 antagonists), in elevating peripheral blood levels of various hematopoietic cell populations including, but not limited to, mononuclear cells (MNC), mature macrophages, hematopoietic progenitor cells and hematopoietic stem cells (alone and/or in combination with G-CSF).

Thus, in one embodiment, there is provided a method for elevating the levels of hematopoietic cells in peripheral blood of a subject comprising administering to the subject an effective amount of a peptide having an amino acid sequence as set forth in SEQ ID NO:1 or an analog or derivative thereof. In certain embodiments, the T-140 analogs may be used to elevate MNC, monocyte, mature macrophage and/or neutrophil peripheral blood levels in conditions wherein such cells are depleted, e.g. due to chemotherapy or irradiation in cancer patients. Thereby, the risk of death and complication due to bacterial, fungal or viral infection may be reduced in these patients. In other embodiments, the T-140 analogs may be used to elevate the levels of hematopoietic progenitor (e.g., CFU-GEMM, BFU-E CFU-GM and CFU-M) and/or stem cells in peripheral blood, e.g. for mobilizing and subsequent harvesting hematopoietic progenitor and/or stem cells for bone marrow transplantation. In a particular embodiment, said cells are selected from CFU-GEMM and BFU-E.

In certain embodiments, the peptide may be administered to said subject in combination with one or more agents used to induce mobilization of white blood cells, e.g. with at least one cytokine that stimulates mobilization of hematopoietic cells (e.g. progenitor and/or stem cells). In one preferable but optional embodiment, the T-140 analog peptides of the invention are administered in combination with Granulocyte Colony-stimulating Factor (G-CSF) or an analog or derivative thereof.

In another embodiment, a T-140 analog of the invention, e.g. a peptide having an amino acid sequence as set forth in SEQ ID NO:1, is used for promoting the recovery of the bone marrow depleted e.g. by irradiation or chemotherapy, for example in cancer patients, and patients with irradiation injuries.

Thus in another embodiment, there is provided a method for elevating the levels of hematopoietic precursor cells in the bone marrow of a subject suffering from or at risk of bone marrow suppression associated with exposure to radiation or chemotherapy, comprising administering to the subject an effective amount of a peptide having an amino acid sequence as set forth in SEQ ID NO:1 or an analog or derivative thereof. In a particular embodiment, said cells are hematopoietic progenitor cells. In various embodiments, said cells are selected from CFU-GEMM, BFU-E CFU-GM and CFU-M, and preferably said cells are selected from CFU-GEMM and BFU-E. In another particular embodiment, said cells are hematopoietic stem cells.

In another aspect, the invention provides a method for obtaining a therapeutically effective amount of hematopoietic precursor cells from a subject, comprising:
 a) administering to the subject an effective amount of a peptide having an amino acid sequence as set forth in SEQ ID NO:1 or an analog or derivative thereof;
 b) harvesting said precursor cells by apheresis; and optionally
 c) repeating steps (a) and (b) until a therapeutically effective amount of hematopoietic precursor cells is obtained.

In certain embodiments, the peptide may be administered to said subject in combination with at least one cytokine that stimulates mobilization of hematopoietic cells. In one preferable but optional embodiment, the T-140 analog peptides of the invention are administered in combination with G-CSF.

In another aspect, there is provided a method for obtaining long term engraftment of hematopoietic precursor cells, comprising the steps of:
 a) administering to a first subject an effective amount of a peptide having an amino acid sequence as set forth in SEQ ID NO:1 or an analog or derivative thereof;
 b) harvesting said hematopoietic precursor cells by apheresis;
 c) optionally repeating steps (a) and (b) until a therapeutically effective amount of hematopoietic precursor cells is obtained; and
 d) transplanting the resulting cells to the first subject or to a second subject in need thereof.

In certain embodiments, the peptide may be administered to said subject in combination with at least one cytokine that stimulates mobilization of hematopoietic cells. In one preferable but optional embodiment, the T-140 analog peptides of the invention are administered in combination with G-CSF.

In another aspect, there is provided a method of increasing G-CSF-induced hematopoietic precursor cell mobilization, comprising administering to a subject an effective amount of G-CSF in concurrent or sequential combination with a peptide having an amino acid sequence as set forth in SEQ ID NO:1 or an analog or derivative thereof. In a particular embodiment, said cells are selected from CFU-GEMM and BFU-E.

In another aspect, there is provided a method of increasing G-CSF-induced elevation of mononuclear cell blood counts, comprising administering to a subject an effective amount of G-CSF in concurrent or sequential combination with a peptide having an amino acid sequence as set forth in SEQ ID NO:1 or an analog or derivative thereof.

In one embodiment, the compositions of the invention are particularly useful for the treatment of cytopenia, e.g. for treating neutropenia. The invention demonstrates, for the first time, that a combination of a neutrophil mobilizing agent such as G-CSF together with a T-140 analog of the invention is capable of restoring neutrophil counts to normal levels. Unexpectedly, as demonstrated hereinbelow using an experimental animal model, mice recovered from neutropenia after 7 days from the onset of treatment. Thus, in another aspect, there is provided a method for reducing the duration of cytopenia in a subject in need thereof comprising administering to the subject an effective amount of G-CSF in concurrent or sequential combination with a peptide having an amino acid sequence as set forth in SEQ ID NO:1 or an analog or derivative thereof.

In some embodiments, said subject is suffering from e.g. cytopenia associated with high dose chemotherapy or irradiation, cytopenia associated with conventional oncology therapy, drug-induced cytopenia, toxin-induced cytopenia, and radiation-induced cytopenia or cytopenia associated with conventional bone marrow transplantation. In certain other embodiments, the duration of cytopenia (e.g. neutropenia) is reduced to a period of 2-3 weeks or less from initiation of the combination therapy, preferably below 2 weeks, more preferably below 10 days, still more preferably below 7 days, even more preferably below 4 days, and most preferably below 3 days. In other embodiments, the duration of cytopenia is reduced below 2 days and is preferably reduced to 1 day or less from the onset of treatment.

In another aspect, there is provided a pharmaceutical composition comprising as active ingredients effective amounts of G-CSF and a peptide having an amino acid sequence as set forth in SEQ ID NO:1 or an analog or derivative thereof.

In another aspect, there is provided a pharmaceutical kit containing: i) G-CSF and ii) a peptide having an amino acid sequence as set forth in SEQ ID NO:1 or an analog or derivative thereof.

Other objects, features and advantages of the present invention will become clear from the following description and drawings.

BRIEF DESCRIPTION OF THE DRAWINGS

FIG. 1 demonstrates that 4F-benzoyl-TN14003 enhances MIP3α secretion by the prostate cancer cell line PC3 in a CXCR4-dependent manner.

FIG. 2 illustrates kinetic analysis of 4F-benzoyl-TN14003 administration on mobilization of WBCs.

FIG. 3 presents a dose response analysis of 4F-benzoyl-TN14003 administration on mobilization of WBCs.

FIG. 6 demonstrates that 4F-benzoyl-TN14003 synergizes with G-CSF to mobilize WBC and is more potent in this ability than AMD3100. C57BL/6 mice were s.c. injected with G-CSF 2.5 μg twice a day for four days. 18 hours after the last injection mice were injected with 5 mg/kg of either 4F-benzoyl-TN14003 or AMD3100 and 2 h later sacrificed and peripheral blood cells were obtained.

FIG. 7 presents time and dose response effects of 4F-benzoyl-TN14003 on mobilization of hematopoietic progenitor cells to the blood.

FIG. 8 demonstrates that 4F-benzoyl-TN14003 synergizes with G-CSF to mobilize HPCs and is more potent in this ability than AMD3100. C57BL/6 mice were s.c. injected with G-CSF 2.5 μg twice a day for four days. 18 hours after the last injection mice were injected with 5 mg/kg of either 4F-benzoyl-TN14003 or AMD3100 and 2 h later sacrificed and peripheral blood cells were obtained.

FIG. 11 depicts neutralization of 4F-benzoyl-TN14003 function with proteinase K.

FIG. 12 depicts the effect of 4F-benzoyl-TN14003 on chemotherapy-induced neutropenia. Neutrophil counts in cyclophosphamide-administered mice treated with either G-CSF, 4F-benzoyl-TN14003 or a combination thereof, was determined.

FIG. 13 illustrates the effect of 4F-benzoyl-TN14003 on granulocyte counts in the blood and bone marrow in a chemotherapy model.

FIG. 14 illustrates the effects of 4F-benzoyl-TN14003 AND G-CSF on granulocyte counts in the blood and bone marrow in a chemotherapy model.

(squares), CPM and G-CSF (crosses) or CPM, G-CSF and 4F-benzoyl-TN14003 (circles) assessed by flow cytometry.

FIG. 15 presents the effects of 4F-benzoyl-TN14003 AND G-CSF on the survival of mice upon bacterial infection in a chemotherapy model.

FIG. 16 illustrates the effect of 4F-benzoyl-TN14003 on cell counts in a bone marrow transplantation model.

FIG. 17 depicts in vitro production of progenitors and mature cells.

DETAILED DESCRIPTION OF THE INVENTION

Figure 1A:
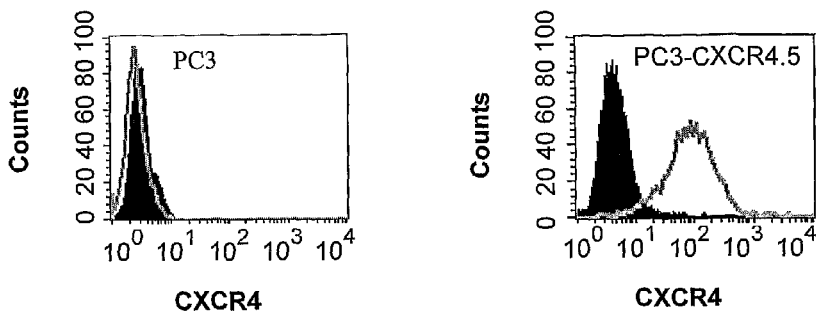
FIG. 1A illustrates FACS analysis of PC3 cells (left panel) and PC3-CXCR4.5 cells (right panel) stained for the control and CXCR4 antibodies.

The present invention is directed to novel compositions and methods wherein T-140 analog peptides, hitherto known as CXCR4 antagonists, are used to stimulate CXCR4-mediated processes in an agonistic manner.

The present invention discloses for the first time that 4F-benzoyl-TN14003 (SEQ ID NO:1), a known CXCR4 inhibitor belonging to the T-140 peptide family, mediates unique beneficial effects, which are not mediated by other CXCR4 inhibitors such as AMD3100. A unique pattern of hematopoietic stem cell (HSC) mobilization was surprisingly found when 4F-benzoyl-TN14003 was administration in vivo—4F-benzoyl-TN14003 was significantly more potent than AMD3100, both alone and when combined with G-CSF, in inducing HSC mobilization, measured both by the increase in HSC blood counts and by the increased ability of the cells to prolong the survival of lethally-irradiated mice.

In addition, 4F-benzoyl-TN14003 was surprisingly found to enhance the level of hematopoietic precursor cells in the bone marrow of lethally irradiated mice, whereas AMD3100 did not demonstrate such effect. 4F-benzoyl-TN14003 was also significantly more potent than AMD3100 in mobilizing various other subpopulations of leukocytes, either alone or with G-CSF; unexpectedly, 4F-benzoyl-TN14003, but not AMD3100, synergized with G-CSF to further stimulate the mobilization of MNCs and mature macrophages.

T-140 Analogs

The peptides described in this specification have an N-terminus (amino-terminal) at the left extremity and a C-terminus (carboxyl-terminal) at the right extremity in accordance with the customary practice of peptide notations.

In this specification and drawings, the representations of amino acids, etc. by brevity codes are made by the use of the codes prescribed by IUPAC-IUB Commission on Biochemical Nomenclature or by the codes customarily used in the relevant art. Examples of such codes are shown below. If an optical isomer exists with respect to an amino acid, it preferably represents the L form unless otherwise expressly specified.

Gly or G: glycine; Ala or A: alanine; Val or V: valine; Leu or L: leucine; Ile or I: isoleucine; Ser or S: serine; Thr or T: threonine; Cys or C: cysteine; Met or M: methionine; Glu or E: glutamic acid; Asp or D: aspartic acid; Lys or K: lysine; Arg or R: arginine; H is or H: histidine; Phe or F: phenylalanine; Tyr or Y: tyrosine; Trp or W: tryptophan; Pro or P: proline; Asn or N: asparagine; Gln or Q: glutamine; pGlu: pyroglutamic acid; Nal: 3-(2-naphthyl) alanine; Cit: citrulline; DLys: D-lysine; DCit: D-citrulline; DGlu: D-glutamic acid; Me: methyl group; Et: ethyl group; Bu: butyl group; Ph: phenyl group.

The substituents, protective group and reagents often used in this specification are indicated by the following codes.

BHA: benzhydrylamine
pMBHA: p-methylbenzhydrylamine
Tos: p-toluenesulphonyl
CHO: formyl
HONB: N-hydroxy-5-norbornene-2,3-dicarboximide
OcHex: cyclohexyl ester
Bzl: benzyl
Cl$_2$-Bzl: dichloro-benzyl
Bom: benzyloxymethyl
Z: benzyloxycarbonyl
Br—Z: 2-bromobenzyloxycarbonyl
Boc: t-butyloxycarbonyl
DCM dichloromethane
HOBt: 1-hydroxybenzotriazole
DCC: N,N'-dicyclohexylcarbodiimide
TFA: trifluoroacetic acid
DIEA: diisopropylethylamine
Fmoc: N-9-fluorenylmethoxycarbony
DNP: dinitrophenyl
Bum: tertiarybutoxymethyl
Trt: trityl
Ac: acetyl
Guanyl: guanyl
Succinyl: succinyl
glutaryl: glutaryl
TMguanyl: tetramethylguanyl
2F-benzoyl: 2-fluorobenzoyl
4F-benzoyl: 4-fluorobenzoyl
APA: 5-aminopentanoyl
ACA: 6-aminohexanoyl
desamino-Arg: 2-desamino-arginyl deamino TMG-APA: the following formula

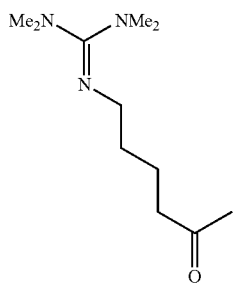

R—CH2: the following formula (V):

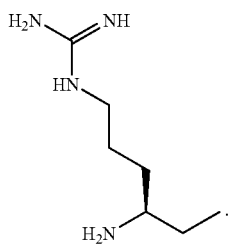

In N-terminal amino acids, [H—] indicates that the terminal amino group is not derivatized, and in C-terminal amino acids, [—OH] indicates that the terminal carboxyl group is not derivatized.

The 4F-benzoyl-TN14003 analogs and derivatives of the invention belong to a family of structurally closely related peptides, also known as T-140 analogs.

T-140 is a known peptide having the amino acid sequence H-Arg-Arg-NaI-Cys-Tyr-Arg-Lys-DLys-Pro-Tyr-Arg-Cit-Cys-Arg-OH (SEQ ID NO:69, Tamamura et al., 2003). The preferable peptides of the invention include analogs and derivatives disclosed in patent applications WO 2002/020561 and WO 2004/020462.

In one aspect, the present invention relates to the use of pharmaceutical compositions comprising as an active ingredient a peptide indicated by the following formula (I) or a salt thereof:

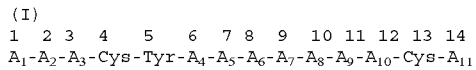

wherein:

$A_1$ in the above-mentioned formula (I) represents an arginine, lysine, ornithine, citrulline, alanine or glutamic acid residue (either L or D form) which may be derivatized at the N-terminus, or $A_1$ is a hydrogen atom, or it is preferable that $A_1$ is an arginine, citrulline, alanine or D-glutamic acid residue, or $A_1$ is a hydrogen atom.

Examples of "N-terminal derivatized peptides" or "N-α-substituted derivatives" include, but are not limited to, those protected by formyl group; acyl group, e.g., acetyl group, propionyl group, butyryl group, pentanoyl group, C2-6alkanoyl group e.g. hexanoyl group, benzoyl group, arylcarbonyl group e.g. substituted benzoyl group (e.g.: 2-fluorobenzoyl, 3-fluorobenzoyl group, 4-fluorobenzoyl group, 2-bromobenzoyl group, 3-bromobenzoyl group, 4-bromobenzoyl group, 2-nitrobenzoyl group, 3-nitrobezoyl group, 4-nirtobenzoyl group), succinyl group, glutaryl group; nicotinyl group; isonicotinyl group; alkylsulfonyl group (e.g.: methanesulfonyl group, ethanesulfonyl group, propanesulfonyl group, camphorsulfonyl group); arylsulfonyl group (e.g.: p-toluenesulfonyl group, 4-fluorobenzenesulfonyl group, mesitylenesulfonyl group, 4-aminobenzenesulfonyl group, dansyl group, 4-bromobenzenesulfonyl group) etc. Or, the N-terminal amino acid group may be absent.

Optionally and preferably, the peptide is derivatized at the N terminus with a substituted benzoyl group. In a particular embodiment, the substituted benzoyl group is a 4-fluorobenzoyl group. In another particular embodiment, the substituted benzoyl group is a 2-fluorobenzoyl group.

$A_2$ in the above-mentioned formula (I) represents an arginine or glutamic acid residue (either L or D form) if A1 is an arginine, lysine, ornithine, citrulline, alanine or glutamic acid residue (either L or D form) which may be derivatized at the N-terminus, or $A_2$ represents an arginine or glutamic acid residue (either L or D form) which may be derivatized at the N-terminus if $A_1$ is absent, or it is preferable that $A_2$ is an arginine or glutamic acid residue if $A_1$ is an arginine, citrulline, alanine or glutamic acid residue which may be derivatized at the N-terminus, or $A_2$ is an arginine or glutamic acid residue which may be derivatized at N-terminus if $A_1$ is absent. Examples of "peptides derivatized at the N-terminus" include, but are not limited to, the same ones as those mentioned in A1.

$A_3$ in the above-mentioned formula (I) represents an aromatic amino acid residue (e.g., phenylalanine, tryptophan, 3-(2-naphthyl)alanine, tyrosine, 4-fluorophenylalanine, 3-(1-naphthyl)alanine (either L or D form), or preferably, $A_3$ represents phenylalanine, tryptophan or 3-(2-naphthyl)alanine.

$A_4$ in the above-mentioned formula (I) represents an arginine, lysine, ornithine, citrulline, alanine or glutamic acid residue (either L or D form), or it is preferable that $A_4$ is an arginine, citrulline, alanine or L- or D-glutamic acid residue.

$A_5$ in the above-mentioned formula (I) represents an arginine, lysine, ornithine, citrulline, alanine or glutamic acid residue (either L or D form), or it is preferable that $A_5$ is an arginine, citrulline, alanine, lysine or glutamic acid residue.

$A_6$ in the above-mentioned formula (I) represents a proline, glycine, ornithine, lysine, alanine, citrulline, arginine or glutamic acid residue (either L or D form), or it is preferable that $A_6$ is a D-lysine, D-alanine, D-citrulline or D-glutamic acid residue.

$A_7$ in the above-mentioned formula (I) represents a proline, glycine, ornithine, lysine, alanine, citrulline or arginine residue (either L or D form), or it is preferable that $A_7$ is a proline or alanine residue.

$A_8$ in the above-mentioned formula (I) represents a tyrosine, phenylalanine, alanine, naphthylalanine, citrulline or glutamic acid residue (either L or D form), or it is preferable that $A_8$ is a tyrosine, alanine or D-glutamic acid residue.

$A_9$ in the above-mentioned formula (I) represents an arginine, lysine, ornithine, citrulline, alanine or glutamic acid residue (either L or D form), or it is preferable that $A_9$ is an arginine, citrulline or glutamic acid residue.

$A_{10}$ in the above-mentioned formula (I) represents a citrulline, glutamic acid, arginine or lysine residue (either L or D form), or it is preferable that $A_{10}$ is a citrulline or D-glutamic acid residue.

$A_{11}$ in the above-mentioned formula (I) represents an arginine, glutamic acid, lysine or citrulline residue (either L or D form) which may be derivatized at C-terminus, or it is preferable that $A_{11}$ is an arginine or glutamic acid residue which may be derivatized at the C-terminus.

"C-terminal derivatization" or "C-terminal carboxyl derivatization" includes, without limitation, amidation (—CONH$_2$, —CONHR, —CONRR') and esterification (—COOR). Herein, R and R' in amides and esters include, for example, $C_{1-6}$ alkyl group e.g. methyl, ethyl, n-propyl, isopropyl, or n-butyl, $C_{3-8}$ cycloalkyl group e.g. cyclopentyl, cyclohexyl, $C_{6-12}$ aryl group e.g. phenyl and α-naphthyl, phenyl-$C_{1-2}$ alkyl group e.g. benzyl, phenethyl or $C_{7-14}$ aralkyl group e.g. $C_{1-2}$ alkyl group e.g. α-naphthyl methyl group, and additionally, pivaloyloxymethyl group which is generally used as an oral bioavailable ester.

If a peptide of the present invention has carboxy groups (or carboxylates) at side-chain terminals other than C-terminus, the peptide having amidated or esterificated carboxy groups at side-chain terminals is included in the peptides of the present invention. As the amides and esters in this case, for example, the amides and esters exemplified in $A_{11}$ are similarly used. Also, the peptides of the present invention include peptides in which substituents (e.g. —OH, —SH, amino group, imidazole group, indole group, guanidino group, etc.) on the intramolecular amino acid side chains are protected by suitable protective group (e.g. C1-6 acyl group, C2-6 alkanoyl such as formyl group, acetyl group, etc.), or complex peptides such as glycopeptides combined with sugar chain in the above-mentioned peptides.

Salts of the peptides of the present invention include physiologically acceptable salts of acids or bases and particularly, physiologically acceptable acid addition salts are preferable. Such salts are exemplified by salts of inorganic acids (e.g. hydrochloric acid, phosphoric acid, hydrobromic acid, sulfuric acid), or salts of organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

In one embodiment, the composition comprises a peptide as set forth in formula (I) as defined hereinabove, wherein $A_1$ is a glutamic acid residue or is absent.

In another embodiment, the composition comprises a peptide as set forth in formula (I) as defined hereinabove, wherein $A_4$ is a glutamic acid residue.

In another embodiment, the composition comprises a peptide as set forth in formula (I) as defined hereinabove, wherein $A_6$ is a glutamic acid residue.

In another embodiment, the composition comprises a peptide as set forth in formula (I) as defined hereinabove, wherein $A_8$ is a glutamic acid residue.

In another embodiment, the composition comprises a peptide as set forth in formula (I) as defined hereinabove, wherein $A_9$ is a glutamic acid residue.

In another embodiment, the composition comprises a peptide as set forth in formula (I) as defined hereinabove, wherein $A_5$ is an arginine or glutamic acid residue.

In another embodiment, the composition comprises a peptide as set forth in formula (I) as defined hereinabove, wherein $A_{10}$ is a glutamic acid, arginine or lysine residue.

In another embodiment, the composition comprises a peptide as set forth in formula (I) as defined hereinabove, wherein $A_{11}$ is a glutamic acid, lysine or citrulline residue.

In another embodiment, the peptide has an amino acid sequence as set forth in any one of SEQ ID NOS:1-72 presented in Table 1 herein:

TABLE 1

T-140 and currently preferred T-140 analogs

| Analog | SEQ ID NO: | Amino acid sequence |
|---|---|---|
| 4F-benzoyl-TN14003 | 1 | 4F-benzoly-Arg-Arg-Nal-Cys-Tyr-Cit-Lys-DLys-Pro-Tyr-Arg-Cit-Cys-Arg-NH$_2$ |
| AcTC14003 | 2 | Ac-Arg-Arg-Nal-Cys-Tyr-Cit-Lys-DCit-Pro-Tyr-Arg-Cit-Cys-Arg-OH |
| AcTC14005 | 3 | Ac-Arg-Arg-Nal-Cys-Tyr-Arg-Lys-DCit-Pro-Tyr-Arg-Cit-Cys-Arg-OH |
| AcTC14011 | 4 | Ac-Arg-Arg-Nal-Cys-Tyr-Cit-Lys-DCit-Pro-Tyr-Arg-Cit-Cys-Arg-OH |
| AcTC14013 | 5 | Ac-Arg-Arg-Nal-Cys-Tyr-Cit-Lys-DLys-Pro-Tyr-Cit-Cit-Cys-Arg-OH |
| AcTC14015 | 6 | Ac-Cit-Arg-Nal-Cys-Tyr-Cit-Lys-DLys-Pro-Tyr-Arg-Cit-Cys-Arg-OH |
| AcTC14017 | 7 | Ac-Cit-Arg-Nal-Cys-Tyr-Arg-Lys-DCit-Pro-Tyr-Arg-Cit-Cys-Arg-OH |
| AcTC14019 | 8 | Ac-Arg-Arg-Nal-Cys-Tyr-Arg-Lys-DCit-Pro-Tyr-Cit-Cit-Cys-Arg-OH |
| AcTC14021 | 9 | Ac-Cit-Arg-Nal-Cys-Tyr-Arg-Lys-DLys-Pro-Tyr-Cit-Cit-Cys-Arg-OH |
| AcTC14012 | 10 | Ac-Arg-Arg-Nal-Cys-Tyr-Cit-Lys-DCit-Pro-Tyr-Arg-Cit-Cys-Arg-NH$_2$ |
| AcTC14014 | 11 | Ac-Arg-Arg-Nal-Cys-Tyr-Cit-Lys-DLys-Pro-Tyr-Cit-Cit-Cys-Arg-NH$_2$ |
| AcTC14016 | 12 | Ac-Cit-Arg-Nal-Cys-Tyr-Cit-Lys-DLys-Pro-Tyr-Arg-Cit-Cys-Arg-NH$_2$ |
| AcTC14018 | 13 | Ac-Cit-Arg-Nal-Cys-Tyr-Arg-Lys-DCit-Pro-Tyr-Arg-Cit-Cys-Arg-NH$_2$ |
| AcTC14020 | 14 | Ac-Arg-Arg-Nal-Cys-Tyr-Arg-Lys-DCit-Pro-Tyr-Cit-Cit-Cys-Arg-NH$_2$ |
| AcTC14022 | 15 | Ac-Cit-Arg-Nal-Cys-Tyr-Arg-Lys-DLys-Pro-Tyr-Cit-Cit-Cys-Arg-NH$_2$ |
| TE14001 | 16 | H-DGlu-Arg-Nal-Cys-Tyr-Arg-Lys-DLys-Pro-Tyr-Arg-Cit-Cys-Arg-OH |
| TE14002 | 17 | H-Arg-Glu-Nal-Cys-Tyr-Arg-Lys-DLys-Pro-Tyr-Arg-Cit-Cys-Arg-OH |
| TE14003 | 18 | H-Arg-Arg-Nal-Cys-Tyr-Glu-Lys-DLys-Pro-Tyr-Arg-Cit-Cys-Arg-OH |
| TE14004 | 19 | H-Arg-Arg-Nal-Cys-Tyr-Arg-Glu-DLys-Pro-Tyr-Arg-Cit-Cys-Arg-OH |
| TE14005 | 20 | H-Arg-Arg-Nal-Cys-Tyr-Arg-Lys-DGlu-Pro-Tyr-Arg-Cit-Cys-Arg-OH |
| TE14006 | 21 | H-Arg-Arg-Nal-Cys-Tyr-Arg-Lys-DLys-Pro-Tyr-Glu-Cit-Cys-Arg-OH |
| TE14007 | 22 | H-Arg-Arg-Nal-Cys-Tyr-Arg-Lys-DLys-Pro-Tyr-Arg-Cit-Cys-Glu-OH |
| TE14011 | 23 | H-Arg-Arg-Nal-Cys-Tyr-Cit-Lys-DGlu-Pro-Tyr-Arg-Cit-Cys-Arg-NH$_2$ |
| TE14012 | 24 | H-Arg-Arg-Nal-Cys-Tyr-DGlu-Lys-DCit-Pro-Tyr-Arg-Cit-Cys-Arg-NH$_2$ |
| TE14013 | 25 | H-Arg-Arg-Nal-Cys-Tyr-DGJu-Lys-DGlu-Pro-Tyr-Arg-Cit-Cys-Arg-NH$_2$ |

TABLE 1-continued

T-140 and currently preferred T-140 analogs

| Analog | SEQ ID NO: | Amino acid sequence |
|---|---|---|
| TE14014 | 26 | H-DGlu-Arg-Nal-Cys-Tyr-Cit-Lys-DGlu-Pro-Tyr-Arg-Cit-Cys-Arg-NH$_2$ |
| TE14015 | 27 | H-Arg-Arg-Nal-Cys-Tyr-Cit-Lys-DGlu-Pro-DGlu-Arg-Cit-Cys-Arg-NH$_2$ |
| TE14016 | 28 | H-Arg-Arg-Nal-Cys-Tyr-Cit-Lys-DGlu-Pro-Tyr-Arg-DGlu-Cys-Arg-NH$_2$ |
| AcTE14014 | 29 | Ac-DGlu-Arg-Nal-Cys-Tyr-Cit-Lys-DGlu-Pro-Tyr-Arg-Cit-Cys-Arg-NH$_2$ |
| AcTE14015 | 30 | Ac-Arg-Arg-Nal-Cys-Tyr-Cit-Lys-DGlu-Pro-DGlu-Arg-Cit-Cys-Arg-NH$_2$ |
| AcTE14016 | 31 | Ac-Arg-Arg-Nal-Cys-Tyr-Cit-Lys-DGlu-Pro-Tyr-Arg-DGlu-Cys-Arg-NH$_2$ |
| TF1: AcTE14011 | 32 | Ac-Arg-Arg-Nal-Cys-Tyr-Cit-Lys-DGlu-Pro-Tyr-Arg-Cit-Cys-Arg-NH$_2$ |
| TF2: guanyl-TE14011 | 33 | guanyl-Arg-Arg-Nal-Cys-Tyr-Cit-Lys-DGlu-Pro-Tyr-Arg-Cit-Cys-Arg-NH$_2$ |
| TF3: TMguanyl-TE14011 | 34 | TMguanyl-Arg-Arg-Nal-Cys-Tyr-Cit-Lys-DGlu-Pro-Tyr-Arg-Cit-Cys-Arg-NH$_2$ |
| TF4: TMguanyl-TE14011 (2-14) | 35 | TMguanyl-Arg-Nal-Cys-Tyr-Cit-Lys-DGlu-Pro-Tyr-Arg-Cit-Cys-Arg-NH$_2$ |
| TF5: 4F-benzoyl-TE14011 | 36 | 4F-benzoyl-Arg-Arg-Nal-Cys-Tyr-Cit-Lys-DGlu-Pro-Tyr-Arg-Cit-Cys-Arg-NH$_2$ |
| TF6: 2F-benzoyl-TE1411 | 37 | 2F-benzoyl-Arg-Arg-Nal-Cys-Tyr-Cit-Lys-DGlu-Pro-Tyr-Arg-Cit-Cys-Arg-NH$_2$ |
| TF7: APA-TE14011 (2-14) | 38 | APA-Arg-Nal-Cys-Tyr-Cit-Lys-DGlu-Pro-Tyr-Arg-Cit-Cys-Arg-NH$_2$ |
| TF8: desamino-R-TE14011 | 39 | desamino-R-Arg-Nal-Cys-Tyr-Cit-Lys-DGlu-Pro-Tyr-Arg-Cit-Cys-Arg-NH$_2$ |
| TF9: guanyl-TE14011 (2-14) | 40 | Guanyl-Arg-Nal-Cys-Tyr-Cit-Lys-DGlu-Pro-Tyr-Arg-Cit-Cys-Arg-NH$_2$ |
| TF10: succinyl-TE14011 (2-14) | 41 | succinyl-Arg-Nal-Cys-Tyr-Cit-Lys-DGlu-Pro-Tyr-Arg-Cit-Cys-Arg-NH$_2$ |
| TF11: glutaryl-TE14011 (2-14) | 42 | glutaryl-Arg-Nal-Cys-Tyr-Cit-Lys-DGlu-Pro-Tyr-Arg-Cit-Cys-Arg-NH$_2$ |
| TF12: deaminoTMG-APA-TL14011 (2-14) | 43 | deaminoTMG-APA-Arg-Nal-Cys-Tyr-Cit-Lys-DGlu-Pro-Tyr-Arg-Cit-Cys-Arg-NH$_2$ |
| TF15: H-Arg-CH2NH-RTE14011 (2-14) | 44 | R-CH2-Arg-Nal-Cys-Tyr-Cit-Lys-DGlu-Pro-Tyr-Arg-Cit-Cys-Arg-NH$_2$ |
| TF17: TE14011 (2-14) | 45 | H-Arg-Nal-Cys-Tyr-Cit-Lys-DGlu-Pro-Tyr-Arg-Cit-Cys-Arg-NH$_2$ |
| TF18: TMguanyl-TC14012 | 46 | TMguanyl-Arg-Arg-Nal-Cys-Tyr-Cit-Lys-DCit-Pro-Tyr-Arg-Cit-Cys-Arg-NH$_2$ |
| TF19: ACA-TC14012 | 47 | ACA-Arg-Arg-Nal-Cys-Tyr-Cit-Lys-DCit-Pro-Tyr-Arg-Cit-Cys-Arg-NH$_2$ |
| TF20: ACA-T140 | 48 | ACA-Arg-Arg-Nal-Cys-Tyr-Arg-Lys-DLys-Pro-Tyr-Arg-Cit-Cys-Arg-OH |
| TZ14011 | 49 | H-Arg-Arg-Nal-Cys-Tyr-Cit-Arg-DLys-Pro-Tyr-Arg-Cit-Cys-Arg-NH$_2$ |
| AcTZ14011 | 50 | Ac-Arg-Arg-Nal-Cys-Tyr-Cit-Arg-DLys-Pro-Tyr-Arg-Cit-Cys-Arg-NH$_2$ |
| AcTN14003 | 51 | Ac-Arg-Arg-Nal-Cys-Tyr-Cit-Lys-DLys-Pro-Tyr-Arg-Cit-Cys-Arg-NH$_2$ |
| AcTN14005 | 52 | Ac-Arg-Arg-Nal-Cys-Tyr-Arg-Lys-DCit-Pro-Tyr-Arg-Cit-Cys-Arg-NH$_2$ |
| 4F-benzoyl-TN14011-Me | 53 | 4F-benzoyl-Arg-Arg-Nal-Cys-Tyr-Cit-Lys-DGlu-Pro-Tyr-Arg-Cit-Cys-Arg-NHMe |
| 4F-benzoyl-TN14011-Et | 54 | 4F-benzoyl-Arg-Arg-Nal-Cys-Tyr-Cit-Lys-DGlu-Pro-Tyr-Arg-Cit-Cys-Arg-NHEt |
| 4F-benzoyl-TN14011-iPr | 55 | 4F-benzoyl-Arg-Arg-Nal-Cys-Tyr-Cit-Lys-DGlu-Pro-Tyr-Arg-Cit-Cys-Arg-NHiPr |
| 4F-benzoyl-TN14011-Tyramine | 56 | 4F-benzoyl-Arg-Arg-Nal-Cys-Tyr-Cit-Lys-DGlu-Pro-Tyr-Arg-Cit-Cys-Arg-Tyramine |
| TA14001 | 57 | H-Ala-Arg-Nal-Cys-Tyr-Arg-Lys-DLys-Pro-Tyr-Arg-Cit-Cys-Arg-OH |
| TA14005 | 58 | H-Arg-Arg-Nal-Cys-Tyr-Ala-Lys-DLys-Pro-Tyr-Arg-Cit-Cys-Arg-OH |
| TA14006 | 59 | H-Arg-Arg-Nal-Cys-Tyr-Arg-Ala-DLys-Pro-Tyr-Arg-Cit-Cys-Arg-OH |
| TA14007 | 60 | H-Arg-Arg-Nal-Cys-Tyr-Arg-Lys-DAla-Pro-Tyr-Arg-Cit-Cys-Arg-OH |
| TA14008 | 61 | H-Arg-Arg-Nal-Cys-Tyr-Arg-Lys-DLys-Ala-Tyr-Arg-Cit-Cys-Arg-OH |
| TA14009 | 62 | H-Arg-Arg-Nal-Cys-Tyr-Arg-Lys-DLys-Pro-Ala-Arg-Cit-Cys-Arg-OH |
| TA14010 | 63 | H-Arg-Arg-Nal-Cys-Tyr-Arg-Lys-DLys-Pro-Tyr-Ala-Cit-Cys-Arg-OH |
| TC14001 | 64 | H-Cit-Arg-Nal-Cys-Tyr-Arg-Lys-DLys-Pro-Tyr-Arg-Cit-Cys-Arg-OH |
| TC14003 | 65 | H-Arg-Arg-Nal-Cys-Tyr-Cit-Lys-DLys-Pro-Tyr-Arg-Cit-Cys-Arg-OH |

TABLE 1-continued

T-140 and currently preferred T-140 analogs

| Analog | SEQ ID NO: | Amino acid sequence |
|---|---|---|
| TN14003 | 66 | H-Arg-Arg-Nal-Cys-Tyr-Cit-Lys-DLys-Pro-Tyr-Arg-Cit-Cys-Arg-NH$_2$ |
| TC14004 | 67 | H-Arg-Arg-Nal-Cys-Tyr-Arg-Cit-DLys-Pro-Tyr-Arg-Cit-Cys-Arg-OH |
| TC14012 | 68 | H-Arg-Arg-Nal-Cys-Tyr-Cit-Lys-DCit-Pro-Tyr-Arg-Cit-Cys-Arg-NH$_2$ |
| T-140 | 69 | H-Arg-Arg-Nal-Cys-Tyr-Arg-Lys-DLys-Pro-Tyr-Arg-Cit-Cys-Arg-OH |
| TC14011 | 70 | H-Arg-Arg-Nal-Cys-Tyr-Cit-Lys-DCit-Pro-Tyr-Arg-Cit-Cys-Arg-OH |
| TC14005 | 71 | H-Arg-Arg-Nal-Cys-Tyr-Arg-Lys-DCit-Pro-Tyr-Arg-Cit-Cys-Arg-OH |
| TC14018 | 72 | H-Cit-Arg-Nal-Cys-Tyr-Arg-Lys-DCit-Pro-Tyr-Arg-Cit-Cys-Arg-NH$_2$ |

In each one of SEQ ID NOS:1-72, two cysteine residues are preferably coupled in a disulfide bond.

Currently preferred peptides according to the present invention are peptides having an amino acid sequence as set forth in any one of SEQ ID NOS:1-72. More preferably, it has been previously reported that the T-140 derivatives having an amino acid sequence as set forth in any one of SEQ ID NOS: 1-68 and 70-72 presented in Table 1 may have improved stability in serum and reduced cytotoxicity relative to T-140 (SEQ ID NO:69). However, T-140 may be suitable for use in the methods of the present invention, e.g. when applied by local administration routes.

In another preferable embodiment, the peptide used in the compositions and methods of the invention consists essentially of an amino acid sequence as set forth in SEQ ID NO:1. In another preferable embodiment, the peptide used in the compositions and methods of the invention is of an amino acid sequence as set forth in SEQ ID NO:1. In another embodiment, the peptide is at least 60%, preferably at least 70% and more preferably at least 80% homologous to SEQ ID NO:1. In another embodiment, the peptide is at least about 90% homologous to SEQ ID NO:1. In another embodiment, the peptide is at least homologous to SEQ ID NO:1. In another embodiment, the peptide is at least about 95% homologous to SEQ ID NO:1. Each possibility represents a separate embodiment of the present invention.

In various other particular embodiments, the peptide is selected from SEQ ID NOS:1-72, wherein each possibility represents a separate embodiment of the present invention.

In another particular embodiment, said peptide has an amino acid sequence as set forth in any one of SEQ ID NOS:1-4, 10, 46, 47, 51-56, 65, 66, 68, 70 and 71. In another particular embodiment, said peptide has an amino acid sequence as set forth in any one of SEQ ID NOS:4, 10, 46, 47, 68 and 70. In another particular embodiment, said peptide has an amino acid sequence as set forth in any one of SEQ ID NOS:1, 2, 51, 65 and 66. In another particular embodiment, said peptide has an amino acid sequence as set forth in any one of SEQ ID NOS:53-56.

In a preferable particular embodiment, said peptide has an amino acid sequence as set forth in SEQ ID NO:1. In another particular embodiment, said peptide has an amino acid sequence as set forth in SEQ ID NO:2. In another particular embodiment, said peptide has an amino acid sequence as set forth in SEQ ID NO:51. In another particular embodiment, said peptide has an amino acid sequence as set forth in SEQ ID NO:66.

In another aspect, the invention relates to the use of a pharmaceutical composition comprising a peptide indicated by the following formula (II) or a salt thereof:

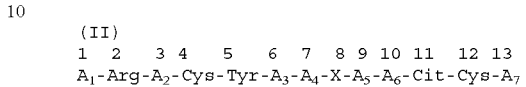

wherein:

A$_1$ represents a hydrogen atom, or an arginine, lysine, ornithine, citrulline or alanine residue or a N-α-substituted derivative of these amino acids;

A$_2$ represents an aromatic amino acid residue;

A$_3$, A$_4$ and A$_6$ each independently represent an arginine, lysine, ornithine, citrulline or alanine residue;

A$_5$ represents a tyrosine, phenylalanine, alanine, naphthylalanine or citrulline residue;

A$_7$ represents a lysine or arginine residue in which a carboxyl group may be amidated or esterified;

X is selected from the group consisting of:

(i) a peptide residue represented by the following formula (III):

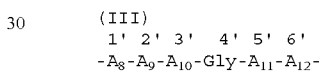

wherein A$_8$ and A$_{12}$ each independently represents an alanine, valine, leucine, isoleucine, serine, cysteine or methionine residue;

A$_9$ represents an aromatic amino acid residue, A$_{10}$ is selected from the same amino acid residues as in A$_3$, A$_{11}$ represents a tyrosine, phenylalanine, tryptophan, alanine, valine, leucine, isoleucine, serine, cysteine or methionine residue, provided that when both of the 1'-position and the 6'-position are cysteine residues, they may be bonded in a disulfide bond, (ii) a peptide selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, and a hydrogen atom of a side chain ω-amino group of D-arginine, L-arginine, D-lysine, L-lysine, D-ornithine or L-ornithine which are constitutional amino acids of said peptide residues may be substituted by a ω-aminoacyl group, and the peptide residues of (i) and (ii) represent a peptide residue which binds amino acid residues at the 7-position and the 9-position through a peptide bond;

and the cysteine residues at the 4-position and the 12-position may be bonded in a disulfide bond;

provided that, in the above polypeptide or a salt thereof, either of the amino acid residues of A$_1$, A$_3$, A$_4$, A$_5$, A$_6$ and A$_7$ is an alanine or citrulline residue; or (iii) a peptide residue containing a D-citrulline, D-alanine, citrulline, or alanine residue) or a salt thereof.

In the polypeptides of the formula (II) of the present invention, A$_1$ is preferably an arginine, alanine or citrulline residue;

$A_2$ is preferably a tryptophan or naphthylalanine residue; $A_3$ is preferably arginine, alanine or citrulline residue; $A_4$ is preferably a lysine, alanine or citrulline residue; X is preferably a D-lysyl-proline, D-alanyl-proline, D-lysyl-alanine or D-citrullyl-proline residue; $A_5$ is preferably a tyrosine or alanine residue; $A_6$ is preferably an arginine, alanine or citrulline residue; $A_7$ is preferably an arginine residue.

Exemplary peptides of the formula (II) are peptides wherein $A_1$, $A_6$ and $A_7$ are arginine residues, $A_2$ is a naphthylalanine residue, $A_3$ is a citrulline residue, $A_4$ is a lysine residue, X is a D-lysyl-proline residue, and $A_5$ is a tyrosine residue, a polypeptide of the formula (II) wherein $A_1$, $A_3$, $A_6$ and $A_7$ are arginine residues, $A_2$ is a naphthylalanine residue, $A_4$ is a lysine residue, X is a D-citrullyl-proline residue, and $A_5$ is a tyrosine residue, a polypeptide of the formula (II) wherein $A_1$, $A_6$ and $A_7$ are arginine residues, $A_2$ is a naphthylalanine residue, $A_3$ is a citrulline residue, $A_4$ is a lysine residue, X is a D-citrullyl-proline residue, $A_5$ is a tyrosine residue, and a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-citrullyl-proline residue, $A_5$ is a tyrosine residue.

The peptides of formula (II) may be exemplified in another embodiment by a peptide of the formula (II) wherein $A_1$, $A_6$ and $A_7$ are arginine residues, $A_2$ is a naphthylalanine residue, $A_3$ is a alanine residue, $A_4$ is a lysine residue, X is a D-lysyl-proline residue, and $A_5$ is a tyrosine residue, a polypeptide of the formula (II) wherein $A_1$ is a citrulline residue, $A_2$ is a naphthylalanine residue, $A_3$, $A_6$ and $A_7$ are arginine residues, $A_4$ is a lysine residue, X is a D-lysyl-proline residue, and $A_5$ is a tyrosine residue, a polypeptide of the formula (II) wherein $A_1$, $A_3$ and $A_7$ are arginine residues, $A_2$ is a naphthylalanine residue, $A_4$ is a lysine residue, X is a D-lysyl-proline residue, $A_5$ is a tyrosine residue, and $A_6$ is a citrulline residue, a polypeptide of the formula (II) wherein $A_1$ and $A_3$ are citrulline residues, $A_2$ is a naphthylalanine residue, $A_4$ is a lysine residue, X is a D-lysyl-proline residue, $A_5$ is a tyrosine residue, $A_6$ and $A_7$ are arginine residues, and a polypeptide of the formula (II) wherein $A_1$, $A_3$ and $A_7$ are arginine residues, $A_2$ is a naphthylalanine residue, $A_4$ is a lysine residue, X is a D-citrullyl-proline residue, $A_5$ is a tyrosine residue, and $A_6$ is a citrulline residue.

The amino acid of $A_7$ as presented in formula II herein is preferably one in which the carboxyl group is amidated for improving stability of the polypeptide in vivo such as in serum, etc.

A peptide of the present invention includes a peptide or its amide, ester or salt containing the amino acid sequence which is substantially the same amino acid sequence as the sequence of any of the above-mentioned peptides. Here, "substantially the same amino acid sequence" means an amino acid sequence that is qualitatively identical in the activity of the peptide or the biological activity of the peptide (e.g. MIP3α secretion) or the like. Accordingly, quantitative variances are acceptable to some extent (e.g. about 0.01 to 100 times, preferably 0.5 to 20 times, or more preferably 0.5 to 2 times). Therefore, one or more of the amino acids in the amino acid sequences indicated in any of the above-mentioned formula (I), (II) and SEQ ID NOS:1-72 can have variances, so far as they have any of the above-mentioned properties. That is to say, in the present invention, any peptide (variant peptide) resulting from the variance in the amino acid sequence such as substitution, deletion or insertion (addition) etc. which brings about any significant change (i.e. a qualitatively different change, or a qualitatively identical but quantitatively significantly different change) in the physiological property or chemical property of the original (non-variant) peptide is deemed as substantially the same as the original (non-variant) peptide having no such variance, and, the amino acid sequence of such variant peptide is deemed as substantially the same as the amino acid sequence of the original (non-variant) peptide.

It is a well-known fact that generally, the changes such as substitution, deletion or insertion (addition) of an amino acid in a peptide sequence often do not make a significant change to physiological properties or chemical properties of such peptide. For example, it is generally considered that substitution of a certain amino acid by another amino acid of similar chemical properties results in a peptide having minimized deviation from the properties of the original peptide.

Amino acids are classified, using the similarity of their properties as to one of the criteria, into the following classes, for example: (i) nonpolar (hydrophobic) amino acids (examples: alanine, leucine, isoleucine, valine, proline, phenylalanine, tryptophan, methionine, etc.); (ii) polar (neutral) amino acids (examples: glycine, serine, threonine, cysteine, tyrosine, asparagine, glutamine, etc.); (iii) basic amino acids carrying positive electric charge (examples: arginine, lysine, histidine, etc.); (iv) acidic amino acids carrying negative electric charge (examples: asparatic acid, glutamic acid, etc.), and accordingly, amino acid substitution within each class can be conservative with regard to the property of a peptide (namely, substitution generating "substantially same" amino acid sequences).

In other words, "substantially the same amino acid sequences" may include:

(i) amino acid sequences wherein 1 or more, or, in other embodiments, 1 to 3 amino acids were substituted by other amino acids in the amino acid sequences indicated in the above-mentioned formula (I), (II) and SEQ ID NOS:1-72;

(ii) amino acid sequences wherein 1 or more, or, in other embodiments, 1 to 3 amino acids were deleted in the amino acid sequences indicated in the above-mentioned formula (I), (II) and SEQ ID NOS:1-72;

(iii) amino acid sequences wherein 1 or more or, in other embodiments, 1 to 3 amino acids were added (inserted) in the amino acid sequences indicated in the above-mentioned formula (I), (II) and SEQ ID NOS:1-72; or (iv) peptides including modifications to amino acids (particularly, the side chains thereof) among the peptides having the amino acid sequences indicated in above (i), (ii) or (iii), or esters, amides or salts thereof.

A peptide of the present invention, if and when the substitution, deletion, insertion (addition), modification, etc. of above (i) to (iv) is intentionally or incidentally provided in the amino acid sequence thereof, can be varied to a stable peptide against heat or protease or a high-activity peptide having more enhanced activity. The peptides of the present invention include also these variant peptides or amides thereof, esters thereof or salts thereof.

Furthermore, among the peptides of the present invention are the peptide consisting of the amino acid sequence indicated in any of the above-mentioned formula (I), (II) and SEQ ID NOS:1-72, and the peptide containing the amino acid sequence sharing the homology of about 50 to 99.9% (preferably, 70 to 99.9%, more preferably 90 to 99.9%) with the foregoing amino acid sequence and having the activities of substantially the same nature as the peptide consisting of the amino acid sequence indicated in any of the above-mentioned formula (I), (II) and SEQ ID NOS:1-72, or amides thereof, esters thereof or salts thereof.

The amides, esters or salts of the peptide having the amino acid sequence indicated in any of the above-mentioned SEQ ID NOS:1-72 include the same ones as are exemplified for the peptide indicated in the above-mentioned formula (I). Preferably, the peptide having the amino acid sequence indicated in any of the above-mentioned SEQ ID NOS:1-72 is amidated at the carboxyl group of the C-terminal amino acid residue.

The peptides of the present invention including the peptide containing the amino acid sequence indicated in any of the above-mentioned SEQ ID NOS:1-72 can be produced by conventionally known methods of synthesizing peptides. For the syntheses of peptides, either solid phase peptide synthesis or liquid phase synthesis may be utilized. Namely, an expected peptide can be produced by condensing a partial peptide able to constitute a peptide or an amino acid with remaining portions, and if the product has a protecting group, by eliminating the protecting group. As the known condensation methods and elimination of protecting groups, the following examples (1) to (5) are included:
(1) M. Bodanszky and M. A. Ondetti, Peptide Synthesis, Interscience Publishers, New York (1966).
(2) Schroeder and Luebke, The Peptide, Academic Press, New York (1965).
(3) N. Izumiya, et. al., Peptide Synthesis, Basics and Practice, Maruzen, Tokyo (1975).
(4) H. Yajima and S. Sakakibara, Seikagaku-Jikken-Koza I, Protein Chemistry IV, Tokyo Kagakudojin, Tokyo, pp 205 (1977).
(5) H. Yajima, Zoku-Iyakuhin-no-Kaihatsu, Vol. 14, Peptide Synthesis, Hirokawa Publishing Co., Tokyo (1991).
As practical methods for syntheses of peptides, the following examples can be given:

Generally, commercially available resins for synthesis of polypeptides can be used. Such resins include, for example, chloromethyl resin, hydroxymethyl resin, benzhydroxylamine resin, aminomethyl resin, 4-hydroxybenzylalcohol resin, 4-methylbenzhydroxylamine resin, PAM resin, 4-hydroxymethylmethylphenylacetoamidomethyl resin, polyacrylamide resin, 4-(2',4'-dimetoxyphenyl-hydroxymethyl) phenoxy resin, 4-2',4'-dimetoxyphenyl-Fmoc aminoethylphenoxy resin, etc. Using such resin, an amino acid with suitably protected α-amino group and side chain functional group is condensed on the resin to the sequence of the expected polypeptide in accordance with conventionally known condensation methods. In the last stage of the reaction, the polypeptide is cleared from the resin and simultaneously various protective groups are removed, and then, by carrying out intramolecular disulfide bond-forming reaction in highly diluted solution, the expected polypeptide or amide thereof is obtained. For the above-mentioned condensation of the protected amino acid, various activated reagents usable for the syntheses of polypeptides can be used, but it is particularly better to use carboxylmides. Among such carboxylmides are DCC, N,N'-diisopropylcarbodiimide, N-ethyl-N'-(3-dimethylaminopropyl)carbodimide, etc. For the activation by these, together with racemization inhibitory additives (for example, HOBt, HOOBt), a protected amino acid is added directly to the resin, or after activating the protected amino acid as symmetric acid anhydride or HOBt ester or HOOBt ester, it can be added to ester resin.

Solvents used for the activation of protected amino acids and the condensation with resins can be chosen from among the solvents known to be usable for polypeptide condensation reactions. For example, acid amides such as N,N-dimethylformamide, N,N-dimethylacetoamide and N-methylpyrrolidone, halogenated hydrocarbons such as methylene chloride and chloroform, alcohols such as trifluoroethanol, sulfoxides such as methyl sulfoxide, ethers such as pyridine, dioxane and tetrahydrofuran, nitriles such as acetonitrile and propionitrile, esters such as methyl acetate and ethyl acetate, or appropriated mixtures of the foregoing are used. A solvent used for activation of a protected amino acid or its condensation with resin can be selected from among the solvents known to be usable for condensing reactions of polypeptides. The reaction temperature is appropriately set within the scope known to be applicable to polypeptide bond forming reactions, usually, at −20° C. to 50° C. Activated amino acid derivatives are usually used at 1.5 to 4 times excess. According to the result of tests adopting ninhydrin reaction, if the condensation is insufficient, the repetition of condensation reactions without eliminating protective groups can lead to sufficient condensation. If sufficient condensation is attained by the repetition of reactions, unreacted amino acids can be acetylated by the use of acetic anhydride or acetylimidazole.

The protective group of the amino group used as ingredients include, for example, Z, Boc, tertialypentyloxycarbony, isobornyloxycarbonyl, 4-methoxybenzyloxycabonyl, Cl—Z, Br—Z, adamantyloxycabonyl, trifluoroacetyl, phtaloyl, formyl, 2-nitrophenylsulphenyl, diphenylphosphinothioyl, Fmoc, etc. Carboxyl group can be protected, for example, by alkyl esterification (e.g. straight-chain, branching or circular alkyl esterification of methyl, ethyl, propyl, butyl, tertialbutyl, cyclopentyl, cyclohexyl, cycloheptyl, cyclooctyl, 2-adamantyl, etc.), aralkyl esterification (e.g. benzylester, 4-nitrobenzylester, 4-methoxybenzylester, 4-chlorbenzylester, benzhydryl esterification), phenacylesterification, benzylcarbonylhydrazidation, tertialybutoxycarbonylhydrazidation, tritylhydrazidation, etc. The hydroxyl group of serine can be protected, for example, by esterification or etherification. The groups suitable for this eterification include, for example, groups derivatized from carboxylic acid such as lower alkanoyl group such as acetyl group, aroyl group such as benzoyl group, benzyloxycarbonyl group, ethoxycarbonyl group. The groups suitable for etherification include, for example, benzyl group, tetrahydropiranyl group, tertiarybutyl group, etc. As the protective groups of phenolic OH group of tyrosine, for example, Bzl, Cl2-Bzl, 2-nitrobenzyl, Br—Z, tertiarlybutyl, etc. are used. As the protective groups of imidazole of histidine, for example, Tos, 4-methoxy-2,3,6-trimethylbenzenesulfonyl, DNP, benzyloxymethyl, Bum, Boc, Trt, Fmoc etc. are used.

Ingredients with activated carboxyl groups include, for example, corresponding acid anhydride, azide, active ester [ester of alcohol (e.g. pentachlorophenol, 2,4,5-trichlorophenol, 2,4-dinitrophenol, cyanomethylalcohol, p-nitrophenol, HONB, N-hydroxysuccimide, N-hydroxyphtalimide, HOBt)] are used. Ingredients with activated amino group include, for example, corresponding phosphoric amide. As the methods to remove (elimiate) protective groups, for example, catalytic reduction in hydrogen airstream in the presence of a catalyst such as Pd-black or Pd-carbon, acid treatment by anhydrous hydrogen fluoride, methanesulfonic acid, trifluoromethanesulfonic acid, trifluoroacetic acid or a mixture thereof, etc, base treatment by diisopropylethylamine, triethylamine, piperidine, piperadine, etc., and reduction by natrium in liquid ammonia are used. Elimination reaction by the above-mentioned acid treatment is done generally at the temperature of about −20° C. to 40° C., but in the acid treatment, it is effective to add a cation trapping agent such as anisole, phenol, thioanisole, m-cresol, p-cresol, dimethylsulfide, 1,4-butanedithiol, 1,2-ethanedithiol. 2,4-dinitrophenyl group used as the protective group of imidazole of histidine is removed by thiophenol treatment. Formyl group used as the protective group of indole of tryptophan is removed by elimination of protection by the above-mentioned acid treatment in the presence of 1,2-ethanedithiol, 1,4-butanedithiol, etc. and also is removed by alkaline treatment by dilute sodium hydroxide solution, dilute ammonia, etc.

Protection and protective group of functional groups not to be involved in the reaction of ingredients, and elimination of such protective group, and activation of functional groups to be involved in the reaction, etc. can be appropriately selected from among conventionally known groups or conventionally known measures. As alternative methods to obtain amides of polypeptides, there is, for example, a method to manufacture, after amidating and protecting α-carboxyl group of carboxy-terminal amino acid and then extending the peptide chain to the desired chain length on the side of amino group, a polypeptide eliminating the protective group of α-amino group of the N-terminus of such peptide chain and a polypeptide eliminating the protective group of carboxyl group of the C-terminus, and then these two peptides are condensed in the above-mentioned mixed solvent. The details of the condensation reaction are the same as described above. After purifying the protected polypeptide obtained by the condensation, the desired raw polypeptide can be obtained by eliminating all the protective groups by the above-mentioned method. Having purified this raw polypeptide using various known purification methods, if the main fraction is freeze-dried, an amide type of the desired polypeptide can be obtained. To get an ester type of the polypeptide, for example, make an amino acid ester by condensing α-carboxyl group of carboxy-terminal amino acid with the desired alcohols, and then, the ester type of the desired polypeptide can be obtained in the same way as the amide type of the polypeptide.

After the reaction, the peptides of the present invention can be purified and isolated by combining usual purification methods such as solvent extraction, distillation, column chromatography, liquid chromatography, re-crystallization, etc. If a peptide obtained by the above-mentioned methods is a salt-free type, it can be converted to a suitable salt by known methods, or if such peptide is a salt, it can be converted to a salt-free type by known methods.

Pharmaceutical Compositions and Kits

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences", Mack Publishing Co., Easton, Pa., which is herein fully incorporated by reference (Remington: The Science and Practice of Pharmacy, Gennaro, A., Lippincott, Williams & Wilkins, Philidelphia, Pa., $20^{th}$ ed, 2000).

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

The pharmaceutical compositions of the invention are suitable for administration systemically or in a local manner, for example, via injection of the pharmaceutical composition directly into a tissue region of a patient (e.g. intralesional injection).

For injection, the active ingredients of the pharmaceutical composition may be formulated in aqueous solutions, preferably in physiologically compatible buffers such as Hank's solution, Ringer's solution, or physiological salt buffer.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

Pharmaceutical compositions suitable for use in the context of the present invention include compositions wherein the active ingredients are contained in an amount effective to achieve the intended purpose. Determination of a therapeutically effective amount is well within the capability of those skilled in the art, especially in light of the detailed disclosure provided herein.

In certain embodiments, the composition may further comprise, in addition to a T-140 analog of the invention, one or more other agents that induce or enhance mobilization or growth factors affecting hematopoietic cells, e.g. stem cell factor (SCF). In some embodiments, the composition may contain at least one cytokine that stimulates mobilization of hematopoietic cells, for example or a colony-stimulating factor, e.g. granulocyte-colony stimulating factor (G-CSF) and granulocyte-macrophages colony stimulating factor (GM-CSF).

In another aspect, the invention provides a pharmaceutical composition comprising as active ingredients effective amounts of granulocyte-colony stimulating factor (G-CSF) and a peptide having an amino acid sequence as set forth in SEQ ID NO:1 or an analog or derivative thereof.

In some embodiments, the term "effective amount" of G-CSF may indicate an amount that is effective, when administered with a T-140 analog of the invention as detailed herein, to mediate the desired effect, e.g. to elevate the levels of WBC in the blood.

The term G-CSF in the context of the present specification and claims is used in its broadest sense in view of a protein having the biological activity of G-CSF as understood by the skilled artisan and comprises polypeptides (either of natural or synthetic including recombinant origin, either modified or not) as defined and described (including their preparation and use) in the scientific literature and, e.g., in any of the following patent publications: DE 30 27 105, EP 169 566, EP 215 126, EP 237 545, EP 396 158, EP 220 520, EP 217 404, EP 230 980, EP 231 819, DE 37 23 781, EP 263 490, EP 344 796, EP 355 811, EP 373 679, EP 401 384, EP 456 812, EP 459 630, EP 459 516, EP 459 795, EP 243 153, EP 272 703, EP 331 186, EP 335 423, WO 93/15211.

The term G-CSF comprises, in addition to G-CSF of natural origin and naturally-occurring variants thereof, any G-CSF coded by a DNA sequence which upon expression by conventional methods in a prokaryotic or eukaryotic (and preferably heterologous) host cell yields a polypeptide product having at least a part of the primary structure, and one or more of the biological properties of naturally-occurring G-CSF, which structure and properties are as defined in EP 237 545. Prokaryotic expression may be accomplished using known prokaryotic vectors and hosts, and may yield a G-CSF of this invention which has the characteristics of a prokaryotic expression product (for example an unglycosylated G-CSF).

As stated above the term G-CSF comprises G-CSF, either of natural or recombinant origin, also in modified form, e.g., coupled to chemical entities which without altering the basic biological activity of G-CSF are capable of modifying it in a therapeutically advantageous way, for example by improving its stability or solubility, or reducing its immunogenicity. A preferred and well-known modification of polypeptides such as G-CSF is by coupling to water-soluble polymers, such as polyethylene glycols or polypropylene glycols, within a wide range of molecular weights, e.g., from 500 to 20,000 daltons. This coupling provides protected G-CSFs, e.g., pegylated G-CSF, which should be substantially non-immunogenic. Various methods of coupling the polymer with G-CSF via different known linkers are known in the art and available to a skilled person. For example, some are described in U.S. Pat. No. 4,179,337. Modified G-CSFs and their preparation are described in EP 401 384, EP 335 423 and EP 473 268. Modified G-CSF also comprises G-CSF which shows a different glycosylation pattern than that known for naturally occurring or recombinant G-CSF, in particular by the addition of at least one polycarbohydrate chain as described in EP 370 205.

Examples of commercially available recombinant human G-CSF include filgrastim (Gran® and Neupogen®), lenograstim (Neutrogin® and Granocyte®) and nartograstim (Neu-up®). Neulasta™ (pegfilgrastim) is a covalent conjugate of recombinant methionyl human G-CSF (Filgrastim) and monomethoxypolyethylene glycol, indicated to decrease the incidence of infection, as manifested by febrile neutropenia, in patients with non-myeloid malignancies receiving myelosuppressive anti-cancer drugs associated with a clinically significant incidence of febrile neutropenia.

In another aspect, there is provided a kit comprising i) at least one cytokine that stimulates mobilization of hematopoietic cells, preferably G-CSF, and ii) a peptide having an amino acid sequence as set forth in SEQ ID NO:1 or an analog or derivative thereof.

In one embodiment, there is provided a pharmaceutical pack containing a course of treatment for one individual mammal comprising a container having a unit of a T-140 analog of the invention in unit dosage form, and a container having a unit of G-CSF.

In some embodiments, the combinations of the invention are provided in packs in a form ready for administration. In other embodiments, the combinations of the invention are provided in concentrated form in packs, optionally with the diluent required to make final solution(s) for administration. In still other embodiments, the product contains a compound useful in the invention in solid form and, optionally, a separate container with a suitable solvent or carrier for the compound useful in the invention.

In still other embodiments, the above packs/kits include other components, e.g., instructions for dilution, mixing and/or administration of the product, other containers, syringes, needles, etc. Other such pack/kit components will be readily apparent to one of skill in the art.

Therapeutic Uses

The present invention demonstrates for the first time, that 4F-benzoyl-TN14003 enhances the levels of hematopoietic precursor and mature cells in the blood and within the bone marrow (BM) in various animal models wherein BM depletion or suppression is involved.

The present invention provides, in another aspect, a method for elevating the levels of at least one type of hematopoietic cells in a subject comprising administering to the subject an effective amount of a peptide having an amino acid sequence as set forth in SEQ ID NO:1 or an analog or derivative thereof.

The term "hematopoietic cell" as used herein refers to any type of cell of the hematopoietic system, including, but not limited to, undifferentiated cells such as hematopoietic stem cells and progenitor cells, and differentiated cells e.g. leukocytes (for example granulocytes, monocytes and lymphocytes).

In another aspect, there is provided a method for elevating the levels of hematopoietic cells in peripheral blood of a subject comprising administering to the subject an effective amount of a peptide having an amino acid sequence as set forth in SEQ ID NO:1 or an analog or derivative thereof.

In another aspect, there is provided a method for elevating the levels of hematopoietic precursor, progenitor and/or stem cells in peripheral blood of a subject comprising administering to the subject an effective amount of a peptide having an amino acid sequence as set forth in SEQ ID NO:1 or an analog or derivative thereof.

The term "hematopoietic stem cell" is used in the broadest sense to refer to stem cells from which blood cells derive, including pluripotent stem cells, lymphoid and myeloid stem cells.

The term "hematopoietic progenitor cell" refers to the progeny of a pluripotent hematopoietic stem cell which are committed for a particular line of differentiation. These committed progenitor cells are irreversibly determined as ancestors of only one or a few blood cell types, e.g. erythrocytes, megakaryocytes, monocytes or granulocytes.

The term "hematopoietic precursor" as used herein includes hematopoietic stem cells, hematopoietic progenitor cells or any cell which gives rise to a cell in the hematopoietic lineages (e.g., lymphoid, myeloid). Examples of hematopoietic precursor cells are CFU-GEMM (colony forming unit-granulocyte-erythrocyte-megakaryocyte-monocyte), CFU-GM (colony forming unit-granulocyte-monocyte), CFU-E (colony forming unit-erythrocyte), BFU-E (burst forming unit-erythrocyte), CFU-G (colony forming unit-granulocyte), CFU-eo (colony forming unit-eosinophil), and CFU-Meg (colony forming unit-megakaryocyte).

According to some embodiments, the T-140 peptide analogs of the invention are herein demonstrated to be particularly useful for elevating peripheral blood level of neutrophils, mononuclear cells (e.g. monocytes, T cells and B cells), mature macrophages, hematopoietic progenitor cells and hematopoietic stem cells.

For example, it was surprisingly found that 4F-benzoyl-TN14003 is particularly potent in elevating blood levels of early progenitors. 4F-benzoyl-TN14003 synergized with G-CSF in elevating BFU-E blood counts, while AMD3100 did not affect G-CSF-induced BFU-E mobilization. In addition, the combination of 4F-benzoyl-TN14003 and G-CSF was much more potent in elevating CFU-GEMM counts than was the combination of AMD3100 and G-CSF.

Thus, in a particular embodiment, there is provided a method for elevating the levels of hematopoietic precursor cells in peripheral blood of a subject comprising administering to the subject an effective amount of a peptide having an amino acid sequence as set forth in SEQ ID NO:1 or an analog or derivative thereof. In one embodiment, the precursor cells are early precursor cells. In another embodiment, the precursor cells are BFU-E. In another embodiment, precursor cells are CFU-GEMM.

In another particular embodiment, there is provided a method for elevating the levels of hematopoietic stem cells having long-term repopulating activity in peripheral blood of a subject comprising administering to the subject an effective amount of a peptide having an amino acid sequence as set forth in SEQ ID NO:1 or an analog or derivative thereof.

In another aspect, there is provided a method for elevating the levels of leukocytes in peripheral blood of a subject comprising administering to the subject an effective amount of a peptide having an amino acid sequence as set forth in SEQ ID NO:1 or an analog or derivative thereof. In one embodiment, the leukocytes are other than natural killer (NK) cells.

In another aspect, there is provided a method for elevating the levels of neutrophils in peripheral blood of a subject comprising administering to the subject an effective amount of a peptide having an amino acid sequence as set forth in SEQ ID NO:1 or an analog or derivative thereof.

In another aspect, there is provided a method for elevating the levels of mononuclear cells in peripheral blood of a subject comprising administering to the subject an effective amount of a peptide having an amino acid sequence as set forth in SEQ ID NO:1 or an analog or derivative thereof.

In another aspect, there is provided a method for elevating the levels of monocytes in peripheral blood of a subject comprising administering to the subject an effective amount of a peptide having an amino acid sequence as set forth in SEQ ID NO:1 or an analog or derivative thereof.

In another aspect, there is provided a method for elevating the levels of mature or activated macrophages in peripheral blood of a subject comprising administering to the subject an effective amount of a peptide having an amino acid sequence as set forth in SEQ ID NO:1 or an analog or derivative thereof.

In another aspect, there is provided a method for elevating the levels of lymphocytes (e.g. B cells or T cells) in peripheral blood of a subject comprising administering to the subject an effective amount of a peptide having an amino acid sequence as set forth in SEQ ID NO:1 or an analog or derivative thereof.

In another embodiment, a T-140 analog of the invention, e.g. a peptide having an amino acid sequence as set forth in SEQ ID NO:1, is used for promoting the recovery of the bone marrow depleted e.g. by irradiation or chemotherapy, for example in cancer patients undergoing cancer associated chemotherapy or bone marrow transplantation and patients with irradiation injuries. Thus in another embodiment, there is provided a method for elevating the levels of hematopoietic precursor cells in the bone marrow of a subject suffering from or at risk of bone marrow suppression associated with exposure to radiation or chemotherapy, comprising administering to the subject an effective amount of a peptide having an amino acid sequence as set forth in SEQ ID NO:1 or an analog or derivative thereof. In a particular embodiment, said cells are hematopoietic progenitor cells. In another particular embodiment, said cells are hematopoietic stem cells.

In another embodiment, the methods are useful for stimulating the proliferation of bone marrow hematopoietic precursors and mature cells.

Without wishing to be bound by any theory or mechanism of action, 4F-benzoyl-TN14003, but not AMD3100 enhances the ability of the BM stroma to promote the recovery of the hematopoietic linage (see, e.g., example 13). This novel effect of 4F-benzoyl-TN14003 on the BM stroma has not been reported for other CXCR4 inhibitors.

In certain preferable embodiments, the peptide is administered to said subject in combination with one or more white blood cell mobilizing agents, e.g. progenitor and/or stem cell mobilizing agents. For example, the peptides may be administered in concurrent or sequential combination with one or more other growth factors or cytokines that affect mobilization, for example colony stimulating factors (e.g. granulocyte-colony stimulating factor, G-CSF and granulocyte-macrophages colony stimulating factor, GM-CSF) and stem cell factor, SCF). In other preferable embodiments, the peptide is administered in combination with G-CSF.

In other embodiment, the compositions of the invention are particularly useful for the treatment of cytopenia, e.g. neutropenia. The invention demonstrates, for the first time, that a combination of a neutrophil mobilizing agent such as G-CSF together with a T-140 analog of the invention is capable of restoring neutrophil counts to normal levels, thus recovering mice from neutropenia after 7 days from the onset of treatment. Thus, in another aspect, there is provided a method for reducing the period of neutropenia in a subject in need thereof comprising administering to the subject an effective amount of G-CSF in concurrent or sequential combination with a peptide having an amino acid sequence as set forth in SEQ ID NO:1 or an analog or derivative thereof.

The term "cytopenia" as used herein refers to a reduction of cellular elements in the circulating blood. Cytopenia may result from a variety of causes, and include both a general reduction of cell numbers in the blood as well as a specific reduction of a particular cell type, such as leukocyte reduction in leukopenia. Leukopenia is a reduction in the circulating WBC count to <4000/μL. It is usually characterized by a reduced number of circulating neutrophils, although a reduced number of lymphocytes, monocytes, eosinophils, or basophils may also contribute. Thus, immune function is generally greatly decreased. Neutropenia is a reduction in blood neutrophil count. Severe neutropenia is usually defined by an absolute neutrophil count <500/μL. It is more serious when accompanied by monocytopenia and lymphocytopenia. Lymphocytopenia, in which the total number of lymphocytes is <1000/μL in adults, is not always reflected in the total WBC count, because lymphocytes account for only 20 to 40% of the count.

In some embodiments, said subject is suffering from e.g. neutropenia associated with high dose chemotherapy, neutropenia associated with conventional oncology therapy, drug-induced neutropenia, toxin-induced neutropenia, and radiation-induced neutropenia. In certain other embodiments, the duration of neutropenia is reduced below 12 days, preferably below 10 days, more preferably below 8 days and most preferably below 7 days from the onset of treatment. In other embodiments, the duration of neutropenia is reduced below 5 days, preferably below 4 days, more preferably below 3 days, more preferably below 2 days and most preferably below one day from the onset of treatment. In another embodiment, the neutropenia is febrile neutropenia.

In another embodiment, the methods are useful for reducing the incidence of infection and for increasing survival following chemotherapy or radiation therapy in cancer patients.

In another aspect, there is provided a method for obtaining a therapeutically effective amount of hematopoietic progenitor and/or stem cells from a subject, comprising:
  a) administering to the subject an effective amount of a peptide having an amino acid sequence as set forth in SEQ ID NO:1 or an analog or derivative thereof;
  b) harvesting said progenitor and/or stem cells, e.g. by apheresis; and optionally
  c) repeating steps (a) and (b) until a therapeutically effective amount of hematopoietic progenitor and/or stem cells is obtained.

In certain embodiments, the peptide is administered to said subject in combination with one or more progenitor and/or stem cell mobilizing agents. In a particular embodiment, the peptide is administered in combination with G-CSF.

In another aspect, there is provided a method for enhancing engraftment of progenitor and/or stem cells, comprising the steps of:
  a) administering to a first subject an effective amount of a peptide having an amino acid sequence as set forth in SEQ ID NO:1 or an analog or derivative thereof;
  b) harvesting said progenitor and/or stem cells, e.g. by apheresis;
  c) optionally repeating steps (a) and (b) until a therapeutically effective amount of hematopoietic progenitor and/or stem cells is obtained; and
  d) transplanting the resulting cells to the first subject or to a second subject in need thereof.

In one embodiment, the peptide is administered to said subject in combination with one or more progenitor and/or stem cell mobilizing agents. In another particular embodiment, the peptide is administered in combination with G-CSF.

In a preferred embodiment, the second in a subject in need thereof is histocompatible with said first donor subject.

A further aspect of the invention is directed to a method of increasing G-CSF-induced progenitor and/or stem cell mobilization, comprising administering to a subject an effective amount of G-CSF in concurrent or sequential combination with a peptide having an amino acid sequence as set forth in SEQ ID NO:1 or an analog or derivative thereof.

In various embodiments of the present invention, the subject is selected from humans and non-human mammals. In a preferable embodiment, the subject is human.

In another aspect, the invention is directed to the use of a pharmaceutical composition comprising a peptide having an amino acid sequence as set forth in SEQ ID NO:1 or an analog or derivative thereof and optionally a colony stimulating factor (e.g. G-CSF) for the preparation of a medicament for elevating the levels of at least one type of hematopoietic cells in a subject, for elevating the levels of hematopoietic precursor cells in the bone marrow of a subject suffering from or at risk of bone marrow suppression associated with exposure to radiation or chemotherapy, for the treatment of cytopenia, for obtaining a therapeutically effective amount of hematopoietic progenitor and/or stem cells from a subject, for enhancing engraftment of progenitor and/or stem cells, and/or for increasing G-CSF-induced progenitor and/or stem cell mobilization.

In another aspect, there is provided a pharmaceutical composition comprising a peptide having an amino acid sequence as set forth in SEQ ID NO:1 or an analog or derivative thereof and optionally a colony stimulating factor (e.g. G-CSF) for elevating the levels of at least one type of hematopoietic cells in a subject, for elevating the levels of hematopoietic precursor cells in the bone marrow of a subject suffering from or at risk of bone marrow suppression associated with exposure to radiation or chemotherapy, for the treatment of cytopenia, for obtaining a therapeutically effective amount of hematopoietic progenitor and/or stem cells from a subject, for enhancing engraftment of progenitor and/or stem cells, and/or for increasing G-CSF-induced progenitor and/or stem cell mobilization.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans. An exemplary dosage range for human use may be from about 0.05 to about 10 mg/kg per administration (e.g. administered once or twice per day subcutaneously).

G-CSF may typically be used at a dosage range of from 0.001-50 mg/kg. By means of a non-limitative example, the recommended starting dose of NEUPOGEN® is 5 μg/kg/day, administered as a single daily injection by SC bolus injection, by short IV infusion (15 to 30 minutes), or by continuous SC or continuous IV infusion, for decreasing the incidence of infection, as manifested by febrile neutropenia, in patients with nonmyeloid malignancies receiving myelosuppressive anti-cancer drugs associated with a significant incidence of severe neutropenia with fever. Doses may be increased in increments of 5 μg/kg for each chemotherapy cycle, according to the duration and severity of the patient's condition. In some embodiments, co-administration of G-CSF with a peptide according to the invention may enable the use of a reduced dose of G-CSF (e.g. from about 0.005 mg/kg).

The following examples are presented in order to more fully illustrate some embodiments of the invention. They should, in no way be construed, however, as limiting the broad scope of the invention.

EXAMPLES

Materials and Methods

Reagents

AMD3100 was purchased from Sigma, Israel. Granulocyte colony-stimulating factor (G-CSF) (Filgrastim Neupogen) was kindly provided by Prof. Amon Nagler.

4F-benzoyl-TN14003 (SEQ ID NO:1) was synthesized by Novotide Ltd. In order to neutralize the activity of 4F-benzoyl-TN14003 in some experiments proteinase K was used as followed: 4F-benzoyl-TN14003 was incubated with Proteinase K (Dako), for 20 min at 37° C. following by 10 min incubation at 95° C.

Mice and Experimental Protocol

Female C57BL/6 mice (7-8 weeks old) were purchased from Harlan Israel and maintained under specific pathogen-free conditions at the Hebrew University Animal Facility (Jerusalem, Israel).

4F-benzoyl-TN14003 and AMD3100 were reconstituted in PBS at various concentrations (1, 2.5, 5 and 10 mg/kg). Mice were injected subcutaneously in a total volume of 200 μl 2 h before sacrifice. In some experiments mice were sacrificed at different time points -½, 1, 2, 4 and 24 hours post-injection. In the experiments with G-CSF, mice were subcutaneously injected with G-CSF at 2.5 μg/mouse twice a day for 4 days. In the combination experiments, 18 hours after the last injection of G-CSF mice were injected with either 4F-benzoyl-TN14003 or AMD3100. Control mice were injected with PBS at the appropriate volume.

In the chemotherapy-induced neutropenia model, a protocol as previously described was followed (Zuluaga et al., 2006). Briefly, Female C57BL/6 mice were injected intraperitoneally with 150 and 100 mg/kg of Cyclophosphamide (CPM) on days 1 and 4, respectively. Following the treatment with CPM, mice were injected s.c. with either G-CSF (5 mg), 4F-benzoyl-TN14003 (5 mg/kg) or their combination on day 4, 5, 6 and 7. Blood samples were drawn from each mouse on day 0 and two hours after G-CSF/4F-benzoyl-TN14003 injections on days 4, 5, 6 and 7. Lysis of the erythrocyte population in the blood samples was done using ACK lysis buffer. The number of neutrophils was determined by FACS after staining the cells with anti-PE-Gr-1 antibody.

Cell Isolation and Differential Counts

Peripheral blood cells were obtained from mice by cardiac puncture into heparin followed by lysis of erythrocyte population using ACK lysis buffer. BM cells were harvested from one femoral bone by flushing with cold PBS followed by extensive pipetting. Cells were counted using a hemocytometer and total number of cells per 1 ml of blood was calculated.

In some experiments blood samples were re-suspended and processed to cytospin slides, centrifuged, air dried, and stained with Giemsa. The percentage and the morphology of mobilized cells were determined by differential counts of Giemsa-stained cytospin slides.

Flow Cytometry

To assess the number of cells in blood and BM, and to distinguish between the different populations, FACScan flow cytometer was used. Cells derived from these organs were gated according to forward scatter and side scatter to exclude dead cells and to determine granulocytes, mononuclear cells and activated macrophage populations. The number of each cell population was counted. Cells were also stained in 0.1 ml FACS buffer with fluorescence antibodies directed against Gr-1, CD3, mac-1, F4/80, Nk1.1, B220 and Ter-119 molecules or matched isotype controls (all from eBiosience, San Diego, Calif.) for 30 min and washed with FACS buffer.

Immunostained cells were analyzed by flow cytometry using the FACS Caliber Flow Cytometer (BD Biosciences); the data were analyzed using software from CellQuest (version 3.3; BD Biosciences).

Hematopoietic Progenitor Cells (HPCs) Assay

In order to evaluate the number of progenitor cells, a colony-forming cell assay was used. Burst forming units erythrocyte (BFU-E), colony forming units granulocyte-macrophage (CFU-GM), colony forming units megakaryocytes (CFU-M), and colony forming units granulocyte-erythrocyte-monocyte-macrophage (CFU-GEMM) were assayed by plating the cells in Iscove's-modified Dulbecco's Medium (IMDM) containing 1% methylcellulose, 15% FBS, 1% bovine serum albumin (BSA), 3 U/mL rh EPO, $10^4$ M 2-mercaptoethanol, 2 mM L-glutamine, 50 ng/mL rmSCF, 10 ng/mL rmIL-3, 10 μg/mL rh Insulin, 10 ng/mL rh IL-6, and 200 μg/mL Human Transferrin (Methocult GF M3434; StemCell Technologies Inc.). The cultures were incubated at 37° C. in a humidified atmosphere containing 5% $CO_2$. Seven days later, typical colonies were visually scored by morphologic criteria using a light microscope and the frequency of CFU was calculated. Staining colonies with benzidine dihydrochloride (Sigma, Israel) was used to localize hemoglobin-containing cells.

Hematopoietic Stem Cells (HSCs) Assay

C57BL/6 mice, served as donors, were injected with 5 mg/kg of either 4F-benzoyl-TN14003 or AMD3100. 2 h later peripheral blood cells were collected following by ACK lysis and transferred into C57BL/6 recipient mice that were given a lethal dosing of irradiation (900 cGy) 24 h before i.v. injection of cells. A total cell obtained from 900 or 225 microliter of blood was transferred into single recipient mouse in a total volume of 200 μl PBS. Recipient mice transferred with cells obtained from blood of untreated mice or with normal BM cells were served as controls. Survival of mice was monitored for 4 months.

Additionally, 4 months post first transplantation BM cells recovered from lethally irradiated mice repopulated by donor cells were injected i.v. into lethally irradiated secondary mice.

Statistical Analysis

Results are expressed as average±SD. Statistical differences were determined by an analysis of two-tailed Student's t-test. Values of $p<0.05$ were considered to be statistically significant.

The label "4FB-TN14003" as it appears throughout the figures, is used to indicate 4F-benzoyl-TN14003 (SEQ ID NO:1).

Example 1

4F-benzoyl-TN14003 Induces MIP3α Secretion from Prostate Cell Lines in a CXCR4 Agonist Manner A PC3 prostate cell line that overexpresses high levels of CXCR4 was generated. Single cell clones were generated from this PC3-CXCR4 cell line, and one of the clones (PC3-CXCR4.5), which showed a high and stable expression level of CXCR4, was selected for the experiments. FIG. 1A presents FACS histograms of PC3 cells (left panel) and a single cell clone with stable overexpression of CXCR4, GFP and luc genes (PC3-CXCR4.5, right panel) that were stained for the control (IgG2a-PE, full histograms) and CXCR4 (IgG2a-12G5, empty histograms) antibodies.

Figure 1B:
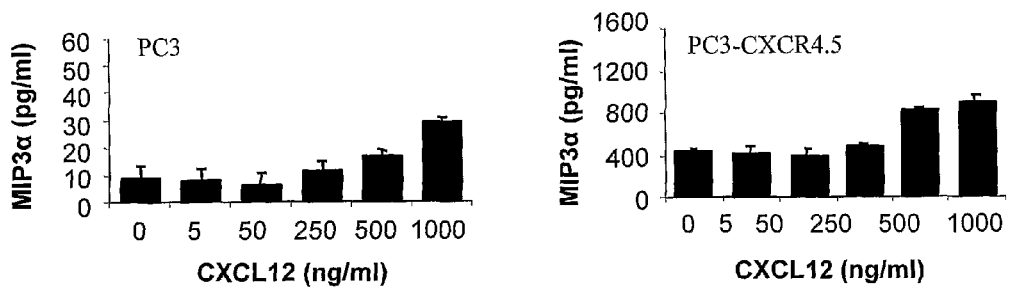
FIG. 1B illustrates MIP3α secretion, assessed by ELISA, of PC3 cells (left panel) and PC3-CXCR4.5 cells (right panel) stimulated with different concentrations of CXCL12 for 48 hours.

In this example, regulation of the chemokine MIP3α (macrophage inflammatory protein 3α) was examined. It was found that PC3-CXCR4.5 cells secreted higher levels of MIP3α than PC3 cells, and increasing doses of CXCL12 increased the secretion of MIP3α in both PC3 and PC3-CXCR4.5 cells (FIG. 1B). In FIG. 1B, PC3 (left panel) and PC3-CXCR4.5 (right panel) cells were stimulated with the indicated concentrations of CXCL12 for 48 hours and MIP3α secretion was assessed by ELISA. The results represent the average of triplicates±STDEV.

Figure 1C:
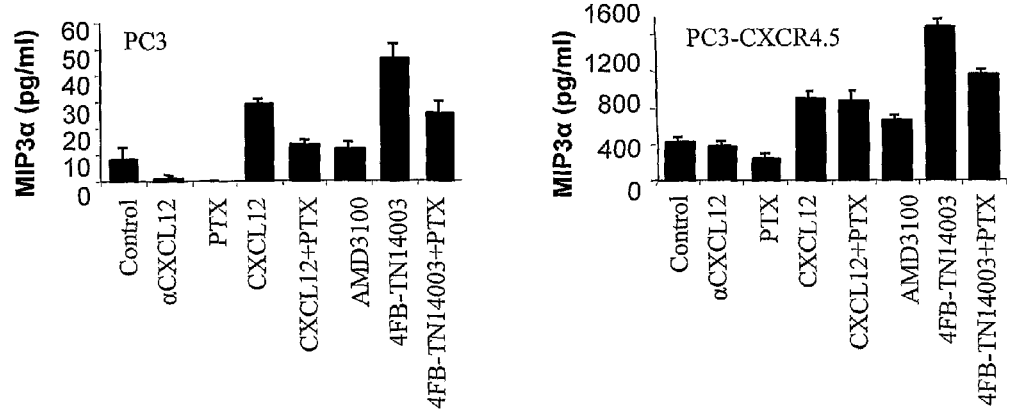
FIG. 1C illustrates MIP3α secretion, assessed by ELISA, of PC3 cells (left panel) and PC3-CXCR4.5 cells (right panel) treated with anti-CXCL12 antibodies, Pertussis toxin, AMD3100 or 4F-benzoyl-TN14003, alone or in combination with CXCL12.
Figure 10:
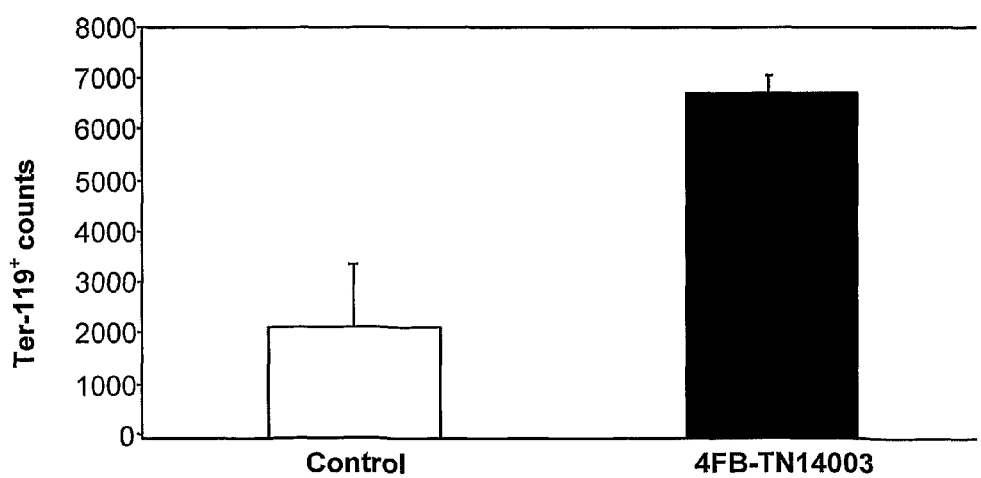
FIG. 10 depicts the number of proerythroblast cells evaluated by FACS following staining with anti-Ter-119 (FITC) of blood cells obtained from control and 4F-benzoyl-TN14003 treated mice.

In PC3 cells, treatment with neutralizing antibodies against CXCL12 (αCXCL12) or with Pertussis toxin (PTX; alone or in combination with CXCL12) effectively inhibited the secretion of MIP3α (FIG. 1C). In contrast, in PC3-CXCR4.5 cells, anti-CXCL12 antibodies did not quite affect the secretion level of MIP3α; with PTX treatment alone, secretion of MIP3α was decreased, but PTX in combination with CXCL12 did not demonstrate an inhibitory effect on the level of MIP3α (FIG. 1C). The effects of the CXCR4 antagonist AMD3100 and of 4F-benzoyl-TN14003 (4FB-TN14003), hitherto known as a CXCR4 antagonist, on MIP3α secretion were further tested. Surprisingly, 4F-benzoyl-TN14003, but not AMD3100 induced in both cell lines MIP3α secretion in an agonist manner (FIG. 10). The effect of 4F-benzoyl-TN14003 was partially inhibited by PTX treatment in both cell lines (FIG. 10). In FIG. 10, CXCR4 signaling in PC3 (left panel) and PC3-CXCR4.5 (right panel) cells was inhibited with anti-CXCL12 antibodies (αCXCL12) and Pertussis toxin (PTX) treatments alone or in combination with CXCL12, as indicated. Secretion of MIP3α was assessed by ELISA. The results represent the average of triplicates±STDEV.

PC3-CXCR4.5 cells secreted higher levels of MIP3α than PC3 cells, and increasing doses of CXCL12 increased the secretion of MIP3α from these cells. Spontaneous secretion of MIP3α is CXCL12 and PTX independent in these cells. The spontaneous, CXCL12-induced and 4F-benzoyl-TN14003-induced secretion was found to be CXCR4 dependent, as determined by evaluation of CXCR4 and MIP3α expression following transfection with CXCR4-specific or control siRNA.

Example 2

Effects of 4f-benzoyl-TN14003 Administration on WBC Mobilization

The effects of 4F-benzoyl-TN14003 on mobilization of cells to the blood of intact mice were evaluated, and the kinetics and dose response of these effects were analyzed. First, mice were injected with 5 mg/kg of 4F-benzoyl-TN14003 and the mobilization of white-blood-cells (WBC), at various time points post-injection, was examined. At ½, 1, 2, 4 and 24 hours post injection of 4F-benzoyl-TN14003, mice were sacrificed and cells were collected from blood and BM. Cells were counted using a hemocytometer and total number of cells per 1 ml of blood was calculated.

Figure 2A:
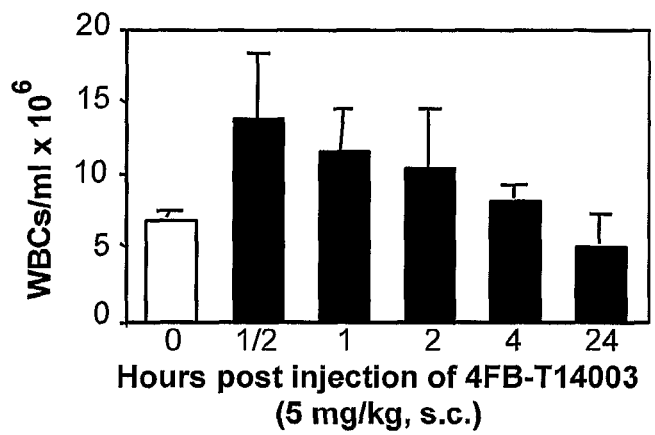
FIG. 2A presents a time course of total WBC mobilization in response to single s.c. injection of 5 mg/kg 4F-benzoyl-TN14003 into C57BL/6 mice, counted using a hemocytometer.
Figure 2B:
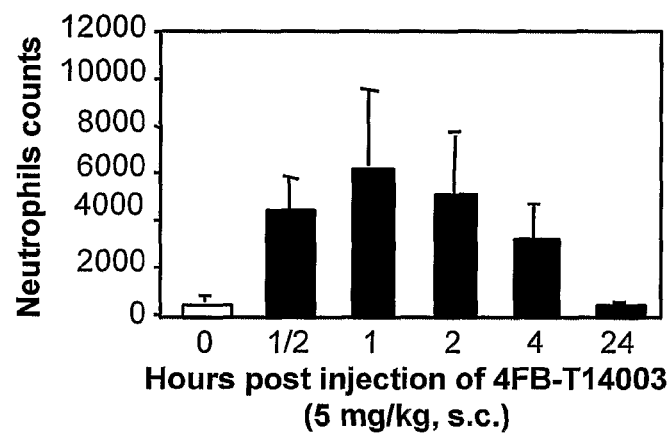
FIGS. 2B, 2C and 2D present the results of FACS analyses preformed to distinguish between different population of the cells, wherein the numbers of neutrophils (FIG. 2B), MNCs (FIG. 2C) and activated macrophages (FIG. 2D) following 4F-benzoyl-TN14003 administration were determined.
Figure 2C:
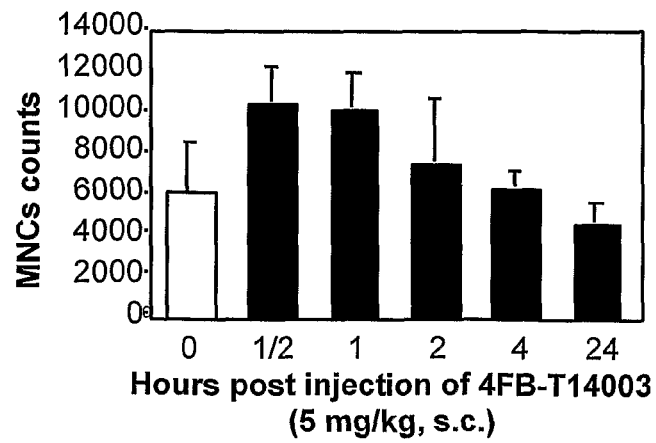
Figure 2D:
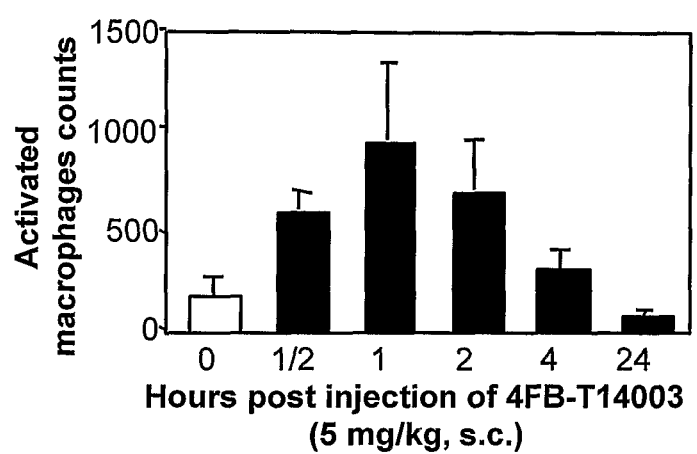

Single dose administration of 5 mg/kg 4F-benzoyl-TN14003 resulted in a rapid elevation in the number of total WBC in blood, 2-fold change from control after 30 minutes which slowly decreased until full return to the baseline level after 24 hours (FIG. 2A). Nevertheless, no changes were observed in the number of white blood cells within the BM of the intact mice. Characterization of the mobilized WBC, using a FACScan flow cytometer, has shown alteration in the absolute number of granulocytes (stained positive with Gr-1), mononuclear cells (MNCs) and activated macrophages (stained positive with both mac-1 and F4/80). Further characterization using cytospin assay defined the granulocyte population as neutrophils. The cells were gated according to forward scatter and side scatter and subpopulation of neutrophils, MNCs and activated macrophages were defined. When the number of neutrophils in the blood was determined, an elevation was observed starting 30 min post injection, reaching a peak after 1 to 2 hours (more than a 12-fold change from control), and slowly decreasing to the baseline level after 24 hours (FIG. 2B). The same pattern was observed for elevation of activated macrophages which reached a peak 1 hour post injection of 4F-benzoyl-TN14003 and returned to the baseline level after 24 hours (FIG. 2D). When the effect of 4F-benzoyl-TN14003 on the mobilization of mononuclear cells (MNCs) was determined, a rapid 2-fold elevation from control was observed after 30 minutes, which rapidly decreased until full return to the baseline level was observed after 4 hours (FIG. 2C). In FIG. 2, data are expressed as average±SD of six mice/group from a total of tow separate experiments performed.

Figure 3A:
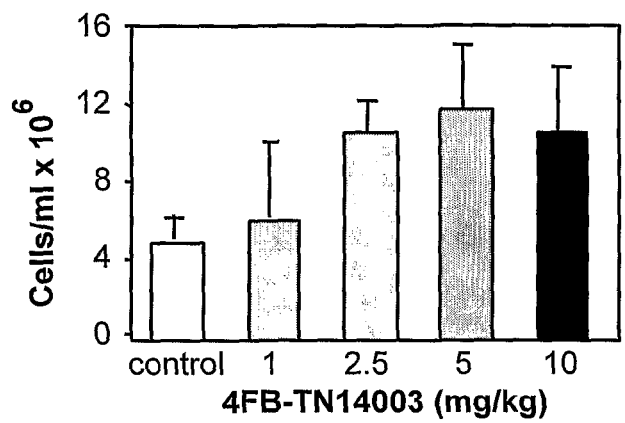
FIG. 3A, total WBCs counted using a hemocytometer.
Figure 3B:
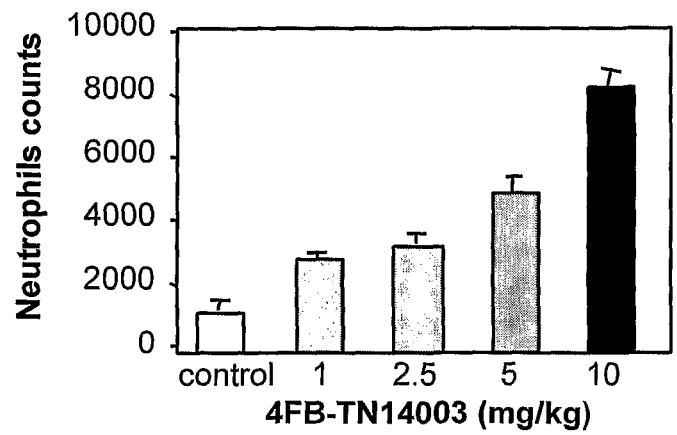
FIG. 3B, neutrophil counts evaluated by FACS.
Figure 3C:
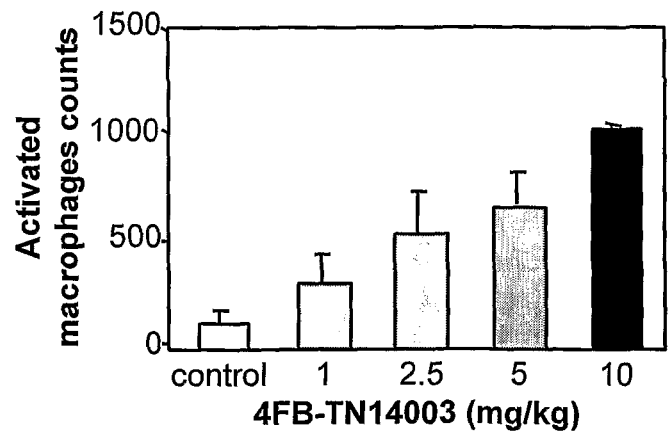
FIG. 3C, activated macrophage counts evaluated by FACS.
Figure 3D:
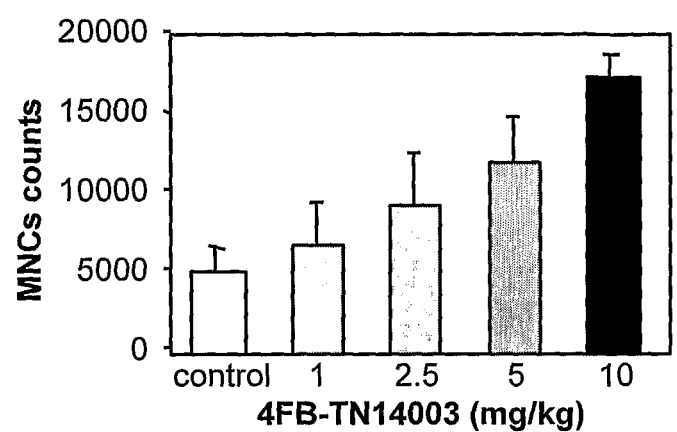
FIG. 3D, MNC counts evaluated by FACS.

The results demonstrate that 4F-benzoyl-TN14003 can efficiency induce mobilization of WBC. In order to determine the effect of different doses of 4F-benzoyl-TN14003, concentrations of 1, 2.5, 5 and 10 mg/kg were subcutaneously injected into C57BL/6 mice. Two hours post-injection, mice were sacrificed and blood and BM cells were collected. The total number of WBC in 1 ml of blood was evaluated using a hemocytometer. A dose response elevation was observed in the number of WBC in blood after treatment with 4F-benzoyl-TN14003. Peak mobilization of the cells occurred at a dose of 5 mg/kg of 4F-benzoyl-TN14003, a 2.5-fold elevation compared to the mobilization level of control mice (FIG. 3A). When the different populations were examined, a similar dose response elevation was found in the absolute number of neutrophils with nearly 8-fold change compared to that of control mice, activated macrophages (6-fold change from control) and MNCs (3.5-fold change from control) in the blood, reaching a peak at 10 mg/kg of 4F-benzoyl-TN14003 (FIGS. 3B, 3C and 3D respectively).

In FIG. 3, data are expressed as average±SD of six mice/group from a total of tow separate experiments performed. In FIG. 3A, WBC counts were evaluated using a hemocytometer. In FIGS. 3B, 3C and 3D the number of neutrophils, activated macrophages and MNCs, respectively, were evaluated by FACS according to forward scatter and side scatter.

In order to further identify the different populations of MNCs that were mobilized by 4F-benzoyl-TN14003, the cells were stained with specific antibodies: CD3 for T cells, B220 for B cells, Mac-1 for monocytes and Nk1.1 for NK cells (FIGS. 4A and 4B).

Figure 4A:
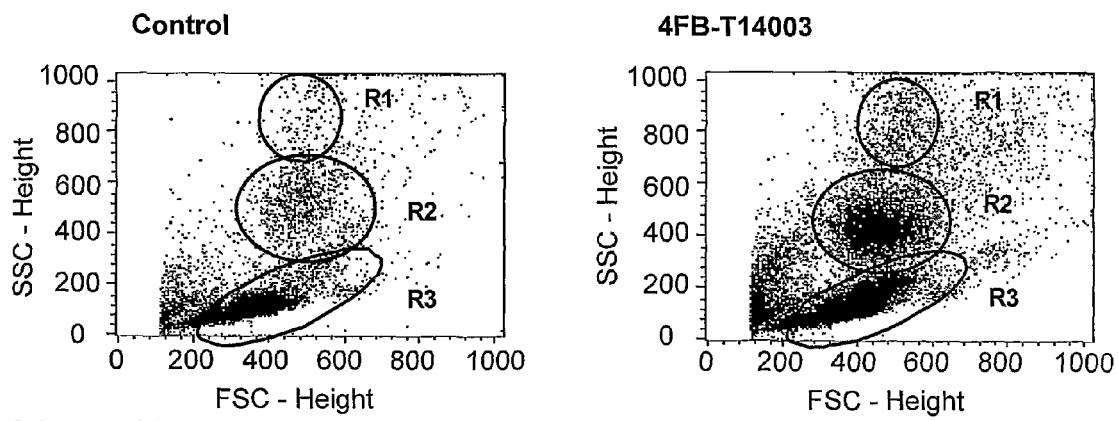
FIG. 4 depicts a representative FACS analysis of blood cells gated according to forward and side scatter (FIG. 4A) to defined activated macrophages (R1), granulocytes (R2) and MNC (R3) subpopulation (FIG. 4B) following staining with anti-FITC-Mac-1 and APC-F4/80 (for activated macrophages) or anti-PE-Gr-1 (for granulocytes). In order to analyze the MNC subpopulations, blood cells were stained with anti-Nk1.1 (PE) for NK cells, Mac-1 (FITC) for monocytes, CD3 (CY) for T cells, and B220 (CY) for B cells.
Figure 4B:
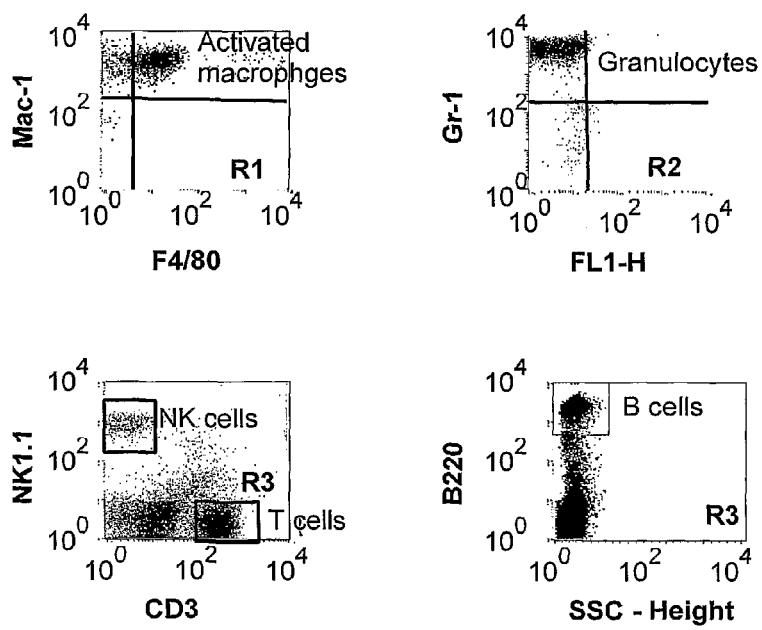

FIG. 4A depicts a representative FACS analysis of blood cells gated according to forward and side scatter to defined activated macrophages (R1), granulocytes (R2) and MNC (R3) subpopulation. Mature macrophages were further identified by staining with anti-FITC-Mac-1 and APC-F4/80. Neutrophils were also identified by staining with or anti-PE-Gr-1. Left panel, control mice; right panel, 4F-benzoyl-TN14003-treated mice. FIG. 4B represents a FACS analysis of blood cells stained with anti-Nk1.1 (PE) for NK cells, Mac-1 (FITC) for monocytes, CD3 (CY) for T cells, and B220 (CY) for B cells. Top left panel, activated macrophages; bottom left panel, NK cells and T cells; top right panel, granulocytes; and bottom right panel, B cells.

Figure 5:
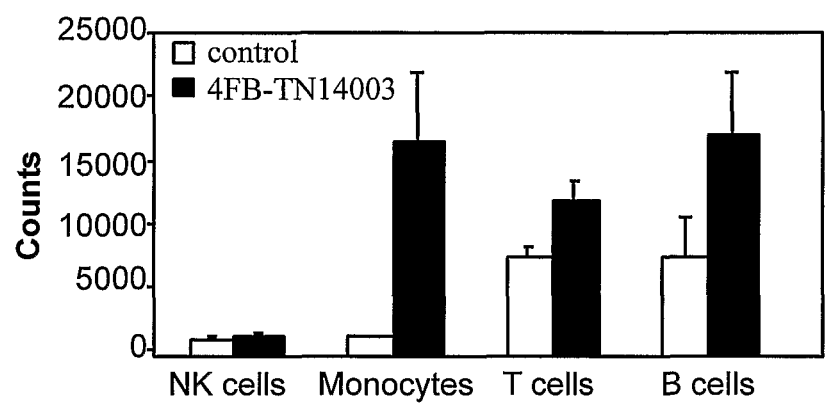
FIG. 5 summarizes results of FACS analysis following 4F-benzoyl-TN14003 administration presented by positive counts following cell staining as described in FIG. 4.

FIG. 5 presents results of the FACS analysis following 4F-benzoyl-TN14003 administration presented by positive counts following cells staining as described above. Mice treated with PBS served as control. Data are expressed as average±SD of six mice/group from a total of two separate experiments performed. White columns, control mice; black columns, 4F-benzoyl-TN14003-treated mice.

As shown in FIG. 5, 4F-benzoyl-TN14003 had an effect on the mobilization of T cells, B cells and monocytes but had no effect on the mobilization of NK cells. Alteration in the number of platelets or other coagulation factor in blood following treatment with 4F-benzoyl-TN14003 was not observed.

Example 3

4F-benzoyl-TN14003 Synergizes with G-CSF to Mobilize WBC

To further study the effect of 4F-benzoyl-TN14003 on mobilization of WBC, the inventors compared its effects with those induced by the conventional treatment with G-CSF. Recently, the CXCR4 antagonist AMD3100 was reported to promote mobilization of stem cells and was found to synergistically augment G-CSF-induced mobilization of hematopoietic progenitor cells. Thus, the mobilizing capability of 4F-benzoyl-TN14003 was compared to that of G-CSF, AMD3100, and the combination of either AMD3100 or 4F-benzoyl-TN14003 with G-CSF. Optimal mobilization induced by AMD3100 or 4F-benzoyl-TN14003 in this experimental protocol was observed using a s.c injection of 5 mg/kg of either agent for 2 hours. G-CSF was subcutaneously injected into C57BL/6 mice 2.5 µg twice a day for 4 days. Eighteen hours after the last injection, 4F-benzoyl-TN14003 or AMD3100 (5 mg/kg) were injected and 2 hours later mice were sacrificed.

Figure 6A:
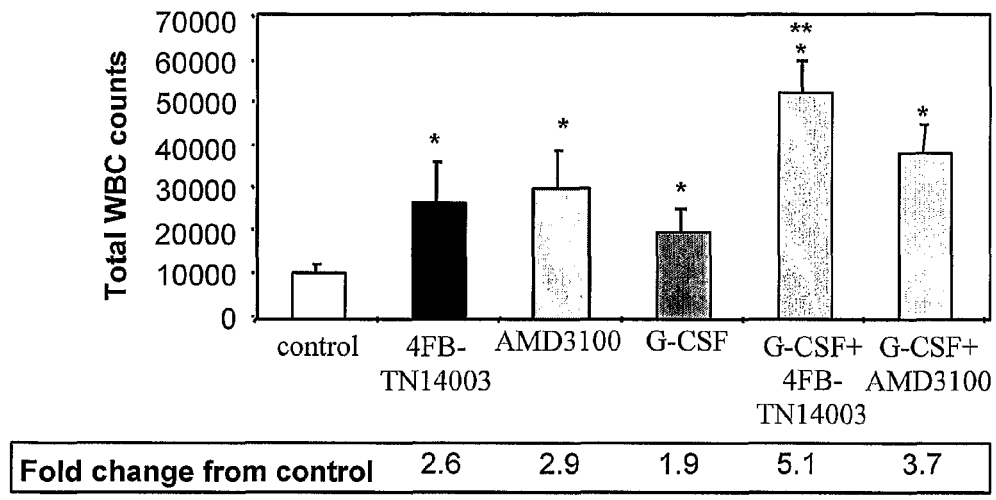
FIG. 6A, total number of WBCs in the blood was counted by FACS.

When the total number of WBC in the blood was analyzed, the inventors found that 4F-benzoyl-TN14003 and AMD3100 alone induced the same level of elevation, i.e. more than 2.5 fold from the control level. G-CSF alone induced an elevation of 1.9 fold from the control level, but the combination of 4F-benzoyl-TN14003 with G-CSF induced an elevation of 5.1-fold from the control level which was significantly higher than the 3.7-fold elevation induced by AMD3100 combined with G-CSF (FIG. 6A).

Analysis of the number of neutrophils in the blood showed a significant elevation induced by 4F-benzoyl-TN14003 and AMD3100 (6.1 and 8-fold change from control, respectively). G-CSF alone induced an elevation of no more than 4.4 fold, while the combination of 4F-benzoyl-TN14003 or AMD3100 with G-CSF induced a synergistic elevation in the number of neutrophils (13.3 and 11.7-fold change from control, respectively; FIG. 6C).

When the number of MNCs in the blood was evaluated, the inventors observed a similar effect of both 4F-benzoyl-TN14003 and AMD3100, which induced an elevation of 2.3 and 3.4-fold change from the control level, respectively. However, only the combination of 4F-benzoyl-TN14003 with G-CSF induced a synergistic elevation of more than 4-fold change from the control level while AMD3100 combined with G-CSF induced an elevation of only 2.6-fold (FIG. 6D). This synergistic effect induced by 4F-benzoyl-TN14003 and G-CSF was also observed when the number of activated macrophages was analyzed. 4F-benzoyl-TN14003 alone increased the number of activated macrophages up to 4.2-fold from the control level; G-CSF alone induced a 1.4-fold elevation from the control level while their combination induced a 8.3-fold elevation from the control level. On the other hand, AMD3100 alone induced a significantly higher elevation (6.1-fold change from the control level) compared to 4F-benzoyl-TN14003 alone; however, its combination with G-CSF did not produce any further elevation (6-fold change from control; FIG. 6E).

Figure 6B:
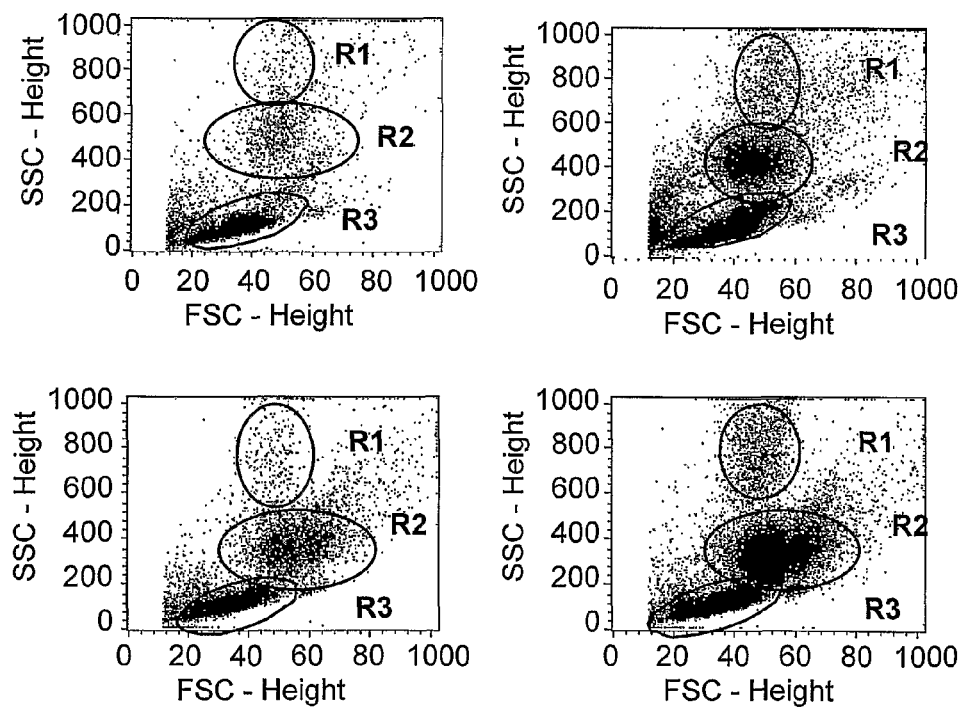
FIG. 6B, a representative FACS analysis of blood cells gated according to forward scatter and side scatter in which subpopulation of activated macrophages (R1), neutrophils (R2) and MNCs (R3) were defined.
Figure 6C:
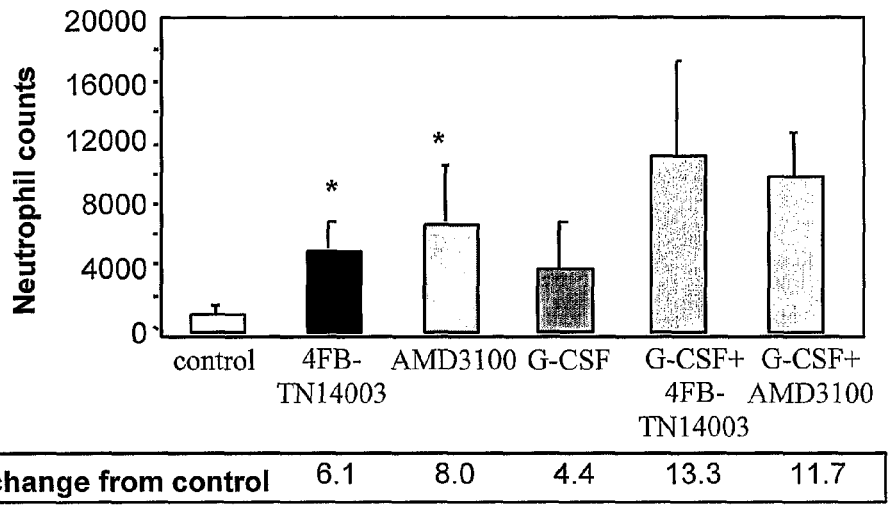
FIGS. 6C, 6D and 6E depict the numbers of neutrophils, activated macphges and MNCs, respectively, following the different treatments.
Figure 6D:
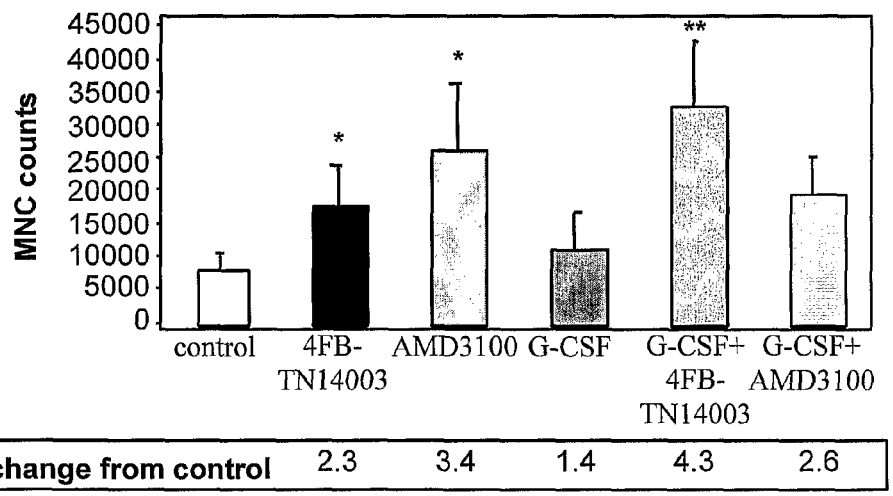
Figure 6E:
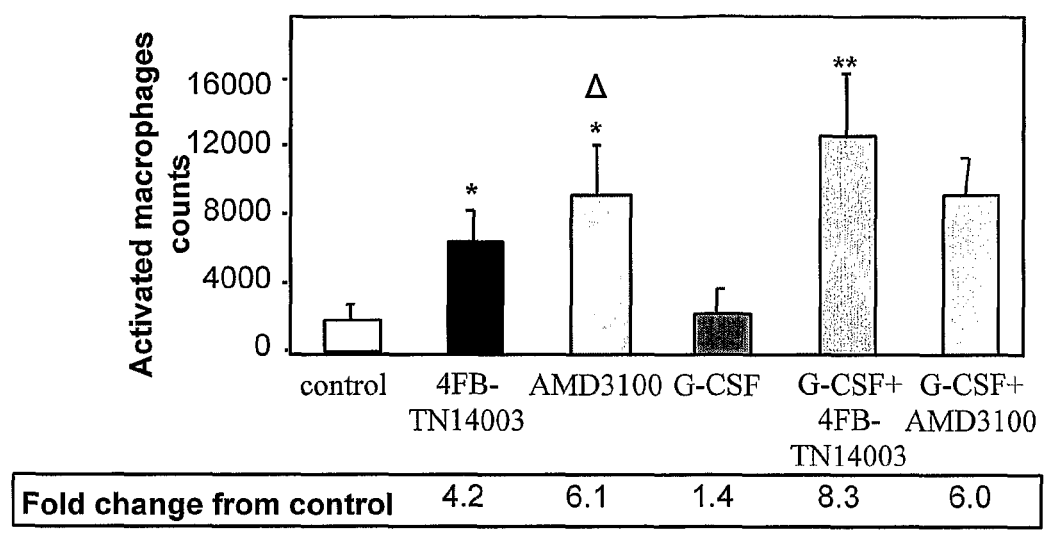

FIG. 6B depicts a representative FACS analysis of blood cells gated according to forward scatter and side scatter, in which subpopulations of activated macrophages (R1), neutrophils (R2) and MNCs (R3) were defined.

In FIGS. 6A, 6C, 6D and 6E, * represents a significant elevation compared to the control group; ** represents a significant elevation in the GCSF+4F-benzoyl-TN14003 treated group compared to the G-CSF+AMD31000 treated group; and A represents a significant elevation (of at least $p<0.05$) of the 4F-benzoyl-TN14003 treated group compared to the AMD31000 treated group. Data are expressed as average±SD of four mice/group from a total of four separate experiments performed. Table 2 below summarizes the changes in measured cell counts compared to the control group:

TABLE 2

| | fold elevation of cell counts | | | | |
|---|---|---|---|---|---|
| | 4F-benzoyl-TN14003 | AMD31000 | G-CSF | G-CSF + 4F-benzoyl-TN14003 | G-CSF + AMD31000 |
| Total WBC | 2.6 | 2.9 | 1.9 | 5.1 | 3.7 |
| Neutrophils | 6.1 | 8.0 | 4.4 | 13.3 | 11.7 |
| MNC | 2.3 | 3.4 | 1.4 | 4.3 | 2.6 |
| Activated macrophages | 4.2 | 6.1 | 1.4 | 8.3 | 6.0 |

Thus, 4F-benzoyl-TN14003, but not AMD3100, synergized with G-CSF to further stimulate the mobilization of MNCs and mature macrophages.

Example 4

Effects of 4F-benzoyl-TN14003 Administration on Progenitor Cell Mobilization

Figure 7A:
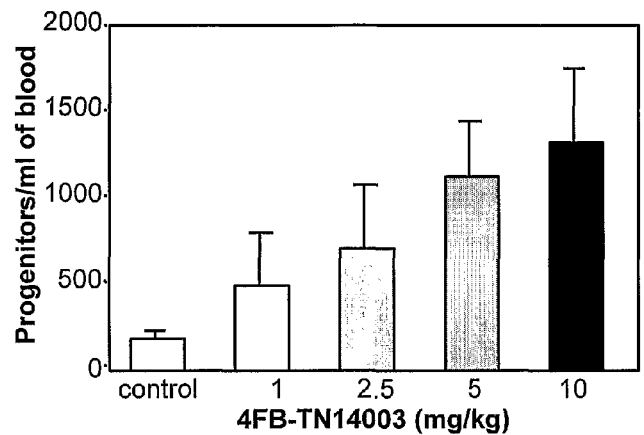
FIG. 7A, dose response analysis at 2 h post s.c. injection of 1, 2.5, 5 or 10 mg/kg 4F-benzoyl-TN14003 into C57BL/6 mice. Peripheral blood cells were obtained and the number of progenitor cells in blood was evaluated by colony-forming cell assay.

In order to study the specific effect of 4F-benzoyl-TN14003 on mobilization of hematopoietic progenitor cells (HPCs), a colony-forming assay was used. 2 h post s.c. injection of 1, 2.5, 5 or 10 mg/kg 4F-benzoyl-TN14003 into C57BL/6 mice, peripheral blood cells were obtained and the number of progenitor cells (CFU-GM, CFU-M, CFU-GEMM and BFU-E) in the blood was evaluated. A dose response elevation in the number of progenitor cells in the blood was detected. Administration of 5 or 10 mg/kg 4F-benzoyl-TN14003 caused an elevation of nearly 10-fold in the number of progenitor cells in 1 ml of blood compared to that of non-treated mice (FIG. 7A).

Figure 7B:
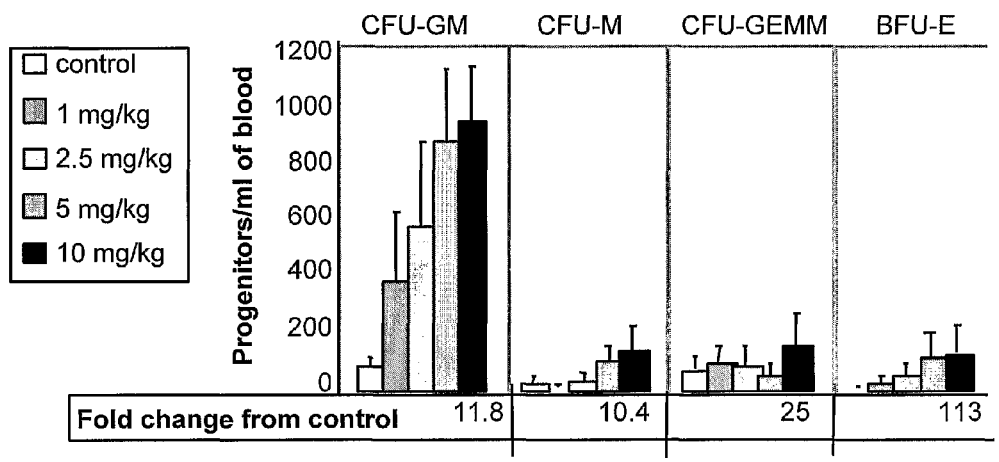
FIG. 7B, dose response analysis for each progenitor cell type (CFU-GM, CFU-M, CFU-GEMM and BFU-E).

When the type of progenitor stem cells was characterized, it was found that following treatment with 4F-benzoyl-TN14003, while most of the mobilized progenitor cells belonged to the CFU-GM subgroup, the same pattern of a dose response elevation also occurred in the CFU-M, CFU-GEMM and BFU-E subgroups, reaching a peak at 5 and 10 mg/kg of 4F-benzoyl-TN14003. A 11.8-fold elevation from the control level was observed in the number of CFU-GM;

similarly, an elevation occurred in the number of CFU-M and CFU-GEMM (10.4 and 2.5 fold elevation from the control level, respectively). The most dramatic alteration was observed in the number of BFU-E, reaching an elevation of more than 110-fold from the control level after administration of 5 and 10 mg/kg of 4F-benzoyl-TN14003 (FIG. 7B).

Figure 7C:
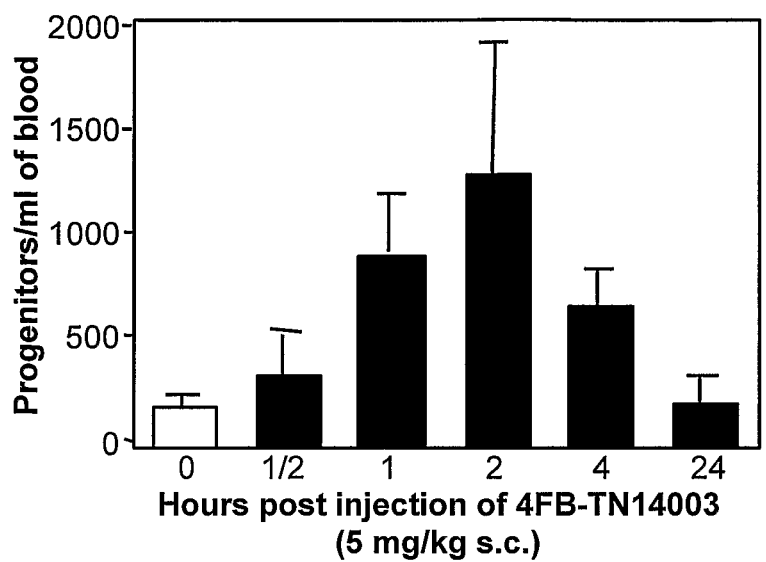
FIG. 7C, time course of hematopoietic progenitor cells mobilization in response to a single s.c. injection of 5 mg/kg of 4F-benzoyl-TN14003.
Figure 7D:
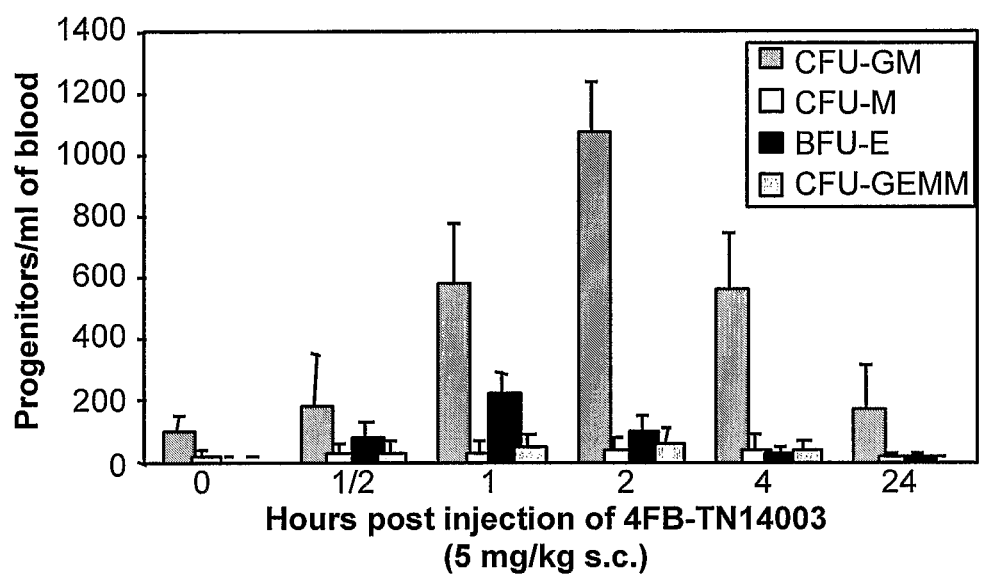
FIG. 7D, time course analysis for each progenitor cell type (CFU-GM, CFU-M, CFU-GEMM and BFU-E).

Next, time course of hematopoietic progenitor cell mobilization in response to a single s.c. injection of 5 mg/kg of 4F-benzoyl-TN14003 was examined. A kinetic study of this effect indicated a dose response elevation in the number of progenitor cells per 1 ml of blood, showing the same bell pattern which started after 30 min (3.2-fold change from control) and reached a peak 1 and 2 hours post-injection of 4F-benzoyl-TN14003 (9.5 and 13.6-fold change from control, respectively). This elevation in the number of progenitor cells in blood almost disappeared 24 hours post-injection (FIG. 7C). When the type of progenitor cells was characterized, it was found that following treatment with 4F-benzoyl-TN14003 a 12.5-fold elevation from control occurs after 2 h in CFU-GM population, 4-fold change occurs 4 h in CFU-M and more than 200-fold change from control observed in the BFU-E 1 h post injection and disappear after 24 h (FIG. 7D).

In FIG. 7, data are expressed as average±SD of six mice/group from a total of two separate experiments performed. Untreated mice served as a control.

Staining mobilized cells with another marker for proerythroblasts, known as Ter119, showed that administration of 4F-benzoyl-TN14003 caused a 3.2-fold elevation from the control level in the number of proerythroblasts in blood (FIG. 10). C57BL/6 mice were s.c. injected with 5 mg/kg 4F-benzoyl-TN14003. 2 hours later blood was obtained and the number of proerythroblast cells was evaluated by FACS following staining with anti-Ter-119 (FITC). Data are expressed as average±SD of five mice/group.

Consistent with the finding that an effect of 4F-benzoyl-TN14003 on the number of WBC within the BM has not been observed in intact mice, a significant change in the total number of marrow progenitor cells following 4F-benzoyl-TN14003 treatment was not detected even at doses as high as 20 mg/kg.

Example 5

4F-benzoyl-TN14003 Synergizes with G-CSF to Mobilize HPC and is More Potent in this Ability than AMD3100

Figure 8A:
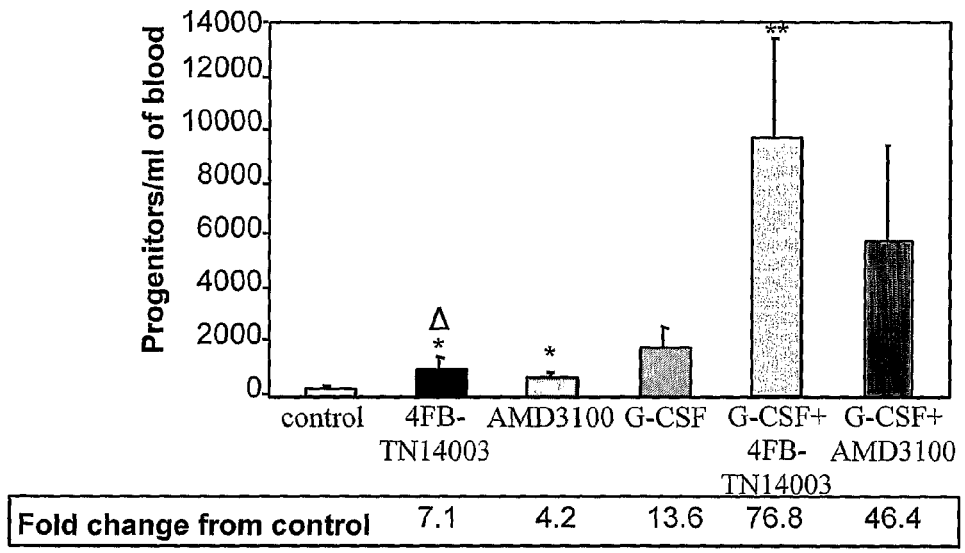
FIG. 8A depicts the number of total progenitor cells in the blood was evaluated by colony-forming cell assay.

When the effects of 4F-benzoyl-TN14003 on progenitor cell mobilization were compared to those of AMD3100, the inventors observed that 4F-benzoyl-TN14003 alone was significantly more potent in its ability to mobilize progenitor cells into the blood. 4F-benzoyl-TN14003 alone increased the number of progenitor cells up to 7.1-fold from control, a significantly higher elevation compared to the 4.2-fold change induced by AMD3100 alone. G-CSF alone induced a 13.6-fold elevation from control while its combination with 4F-benzoyl-TN14003 induced a 76.8-fold elevation from control. This elevation was significantly higher than the synergistic elevation induced by the combination of G-CSF with AMD3100 (a 46.4-fold change from control; FIG. 8A).

Figure 8B:
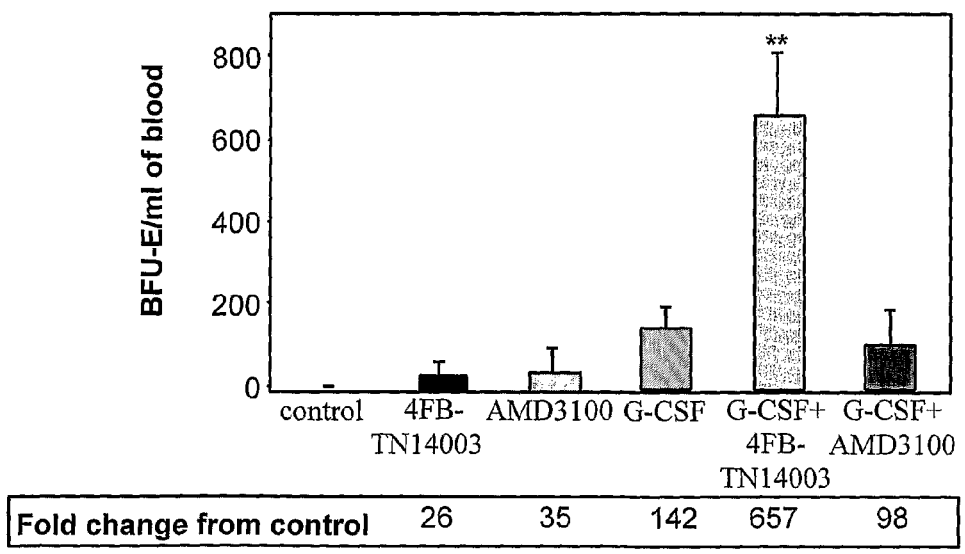
FIGS. 8B and 8C depict the number of BFU-E and CFU-GEMM, respectively, evaluated following staining the colonies with benzidine dihydrochloride to localize hemoglobin-containing cells.
Figure 8C:
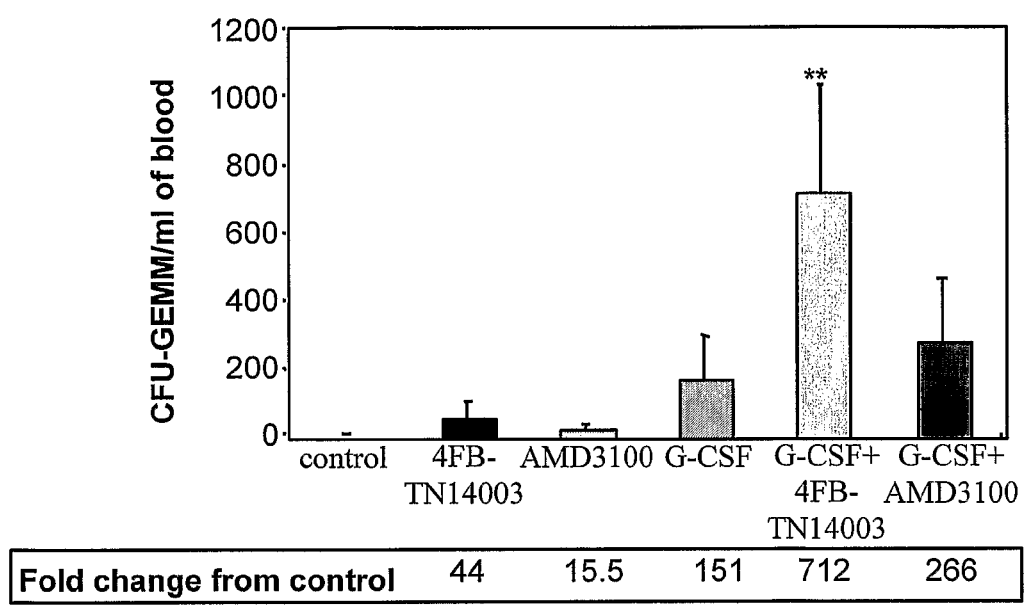

When the specific types of progenitor cells mobilized by those different treatments were characterized, the inventors found the most dramatic change in the mobilization of BFU-E progenitor cells. 4F-benzoyl-TN14003 and AMD3100 alone induced almost the same elevation in the number of BFU-E (nearly 30-fold change from control); G-CSF alone induced a 142-fold elevation from control that did not change upon addition of AMD3100 (98-fold change); however, G-CSF, in combination with 4F-benzoyl-TN14003, induced a significantly higher elevation of BFU-E (660-fold change from control; FIG. 8B). The same pattern was observed when the number of CFU-GEMM colonies that contain mixed progenitor populations including erythroblasts was analyzed. 4F-benzoyl-TN14003 alone was significantly more potent in its ability to mobilize CFU-GEMM (a 44-fold compared to a 15.5-fold change, respectively). G-CSF alone induced a 151-fold elevation from control while its combination with 4F-benzoyl-TN14003 induced a 712-fold elevation from control. This elevation was significantly higher than the elevation induced by the combination of G-CSF with AMD3100 (a 266-fold change from control; FIG. 8C).

In FIG. 8, * represents a significant elevation (of at least $p<0.05$) compared to the control group; ** represents a significant elevation (of at least $p<0.05$) of the G-CSF+4F-benzoyl-TN14003 treated group compared to the G-CSF+AMD31000 treated group; and A represents a significant elevation (of at least $p<0.05$) of the 4F-benzoyl-TN14003 treated group compared to the AMD31000 treated group. Data are expressed as average±SD of four mice/group from a total of four separate experiments performed. Table 3 below summarizes the changes in measured cell counts:

TABLE 3

| | fold elevation of cell counts | | | | |
|---|---|---|---|---|---|
| | 4F-benzoyl-TN14003 | AMD31000 | G-CSF | G-CSF + 4F-benzoyl-TN14003 | G-CSF + AMD31000 |
| Progenitors | 7.1 | 4.2 | 13.6 | 76.8 | 46.4 |
| BFU-E | 26 | 35 | 142 | 657 | 98 |
| CFU-GEMM | 44 | 15.5 | 151 | 712 | 266 |

Example 6

4F-benzoyl-TN14003 Mobilizes HSCS with Long-Term Repopulating Capacity in the Transplantation Model and is More Potent in this Ability than AMD3100

Although mobilization of HPCs may be of use for short-term repopulation in a transplantation setting, HSCs are required for long-term repopulation. To assess the effect of 4F-benzoyl-TN14003 on mobilization of murine HSCs, a transplantation model was used, in which donor C57Bl/6 mice were treated with 4F-benzoyl-TN14003 or AMD3100. After 2 h, blood was collected and cells isolated from an equal volume of blood obtained from each treated group (900 or 225 microliter in different experiments) were transferred for engraftment in lethally irradiated recipient C57Bl/6 mice. Survival of the recipient mice, indicative for long-term repopulating (LTR) activity and presence of HSCs, was monitored.

Figure 9A:
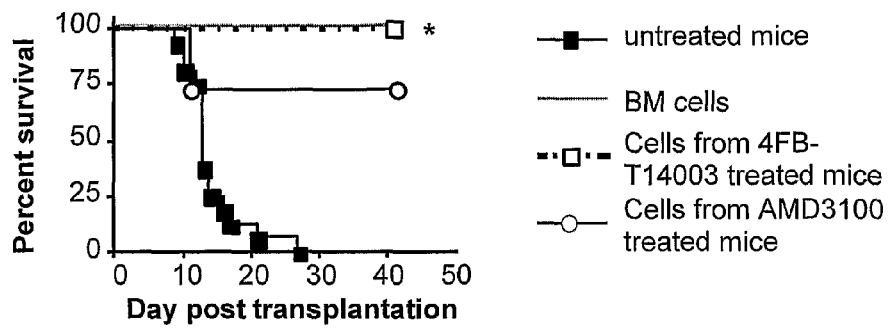
FIG. 9 demonstrates that 4F-benzoyl-TN14003 mobilizes hematopoietic stem cells with long-term repopulating capacity in the transplantation model and is more potent in this ability than AMD3100. C57BL/6 mice, served as donors, were injected with 5 mg/kg of either 4F-benzoyl-TN14003 or AMD3100. 2 h later peripheral blood cells were collected following by ACK lysis and transferred into C57BL/6 recipient mice that were given a lethal dosing of irradiation (900 cGy) 24 h before i.v. injection of cells. Cells obtained from 900 (FIG. 9A) or 225 microliter (FIG. 9B) of blood were transferred into a single recipient mouse.
Figure 9B:
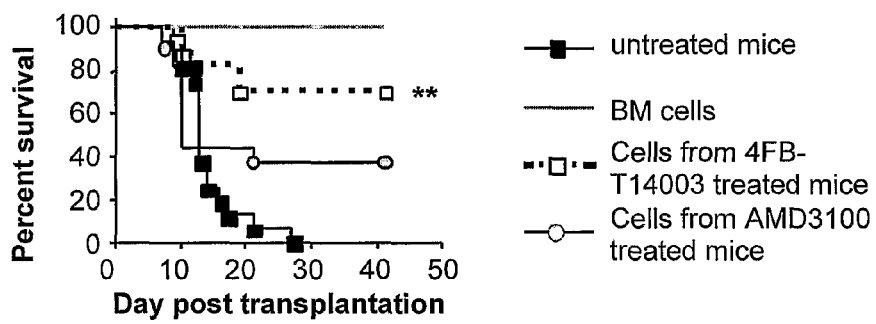

As shown in FIG. 9, one hundred percent of the mice transplanted with cells mobilized by 4F-benzoyl-TN14003, which were obtained from 900 microliter of blood, survived until day 42 post transplantation. Interestingly, cells which were mobilized by AMD3100 did not show an LTR activity as efficient as those mobilized by 4F-benzoyl-TN14003-only 73% of the mice survived at day 11 post transplantation (FIG. 9A). Transfer of 225 microliter of blood resulted at day 33 post transplantation in 70.6% survival of mice which received cells from 4F-benzoyl-TN14003 treated mice, as compared to only 37.5% survival in mice that received cells obtained from the same volume of blood from AMD3100 treated mice. Untreated mice were all dead at day 27 post transplantation and 100% survival was observed in mice that received normal BM cells (FIG. 9B).

The significantly increased ability of cells mobilized by 4F-benzoyl-TN14003 to rescue mice from irradiation, as compared to cells mobilized by AMD3100, demonstrates the improved efficiency of 4F-benzoyl-TN14003 to mobilize HSCs.

In FIG. 9, open squares represent mice transplanted with cells from 4F-benzoyl-TN14003 treated mice, circles represent mice transplanted with cells from AMD3100 treated mice. Recipient mice transplanted with cells obtained from the blood of untreated mice (full squares) or with normal BM cells (gray lines) served as controls. * represents a difference (p=0.06) between the 4F-benzoyl-TN14003 and AMD3100 treatments when 900 microliter were transferred; ** represents a difference (p<0.05) between the 4F-benzoyl-TN14003 and AMD3100 treatments when 225 microliter were transferred. Data are expressed as average of seventeen mice/group from a total of four separate experiments performed.

Example 7

Neutralization of 4F-benzoyl-TN14003 Function

Figure 11A:
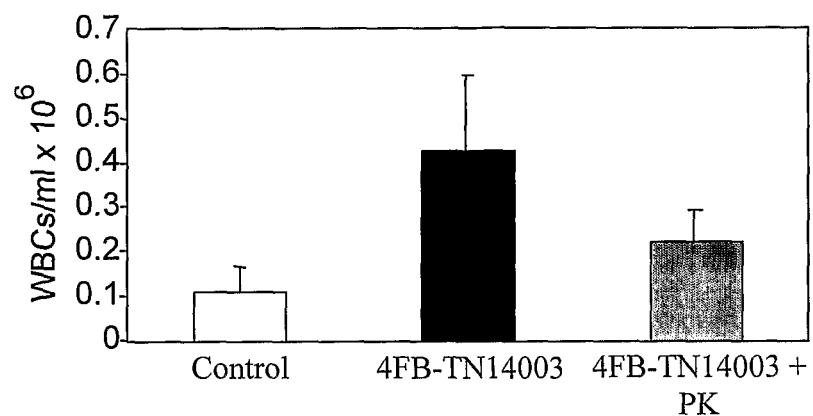
FIG. 11A, the number of WBCs in the blood evaluated using a hemocytometer.
Figure 11B:
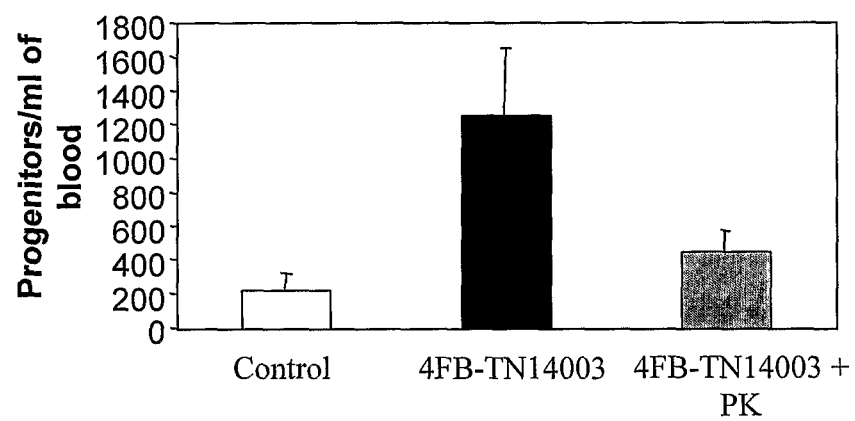
FIG. 11B, mobilization of progenitor cells evaluated by a colony-forming cell assay.

In order to verify that the effects observed are specifically related to the activity of 4F-benzoyl-TN14003, neutralized 4F-benzoyl-TN14003 (treated with proteinase K) was used and its effect was compared to that of natural 4F-benzoyl-TN14003. As shown in FIG. 11, 4F-benzoyl-TN14003 treated with proteinase K could not induce mobilization of WBC or progenitor cells into the blood (FIGS. 11A and 11B, respectively). These results demonstrate that the effect observed on cell mobilization is specifically related to 4F-benzoyl-TN14003 activity.

Neutralization of 4F-benzoyl-TN14003 was done after incubation with proteinase K for 20 min at 37° C. following by 10 min incubation at 95° C. C57BL/6 mice were s.c. injected with 5 mg/kg of either native 4F-benzoyl-TN14003 or neutralized 4F-benzoyl-TN14003. 2 h post injection mice were sacrificed and peripheral blood cells were obtained. Untreated mice served as controls. In FIG. 11A the number of WBCs in the blood was evaluated using a hemocytometer. In FIG. 11B mobilization of progenitor cells was evaluated by a colony-forming cell assay. Data are expressed as average±SD of four mice/group.

Example 8

Figure 12A:
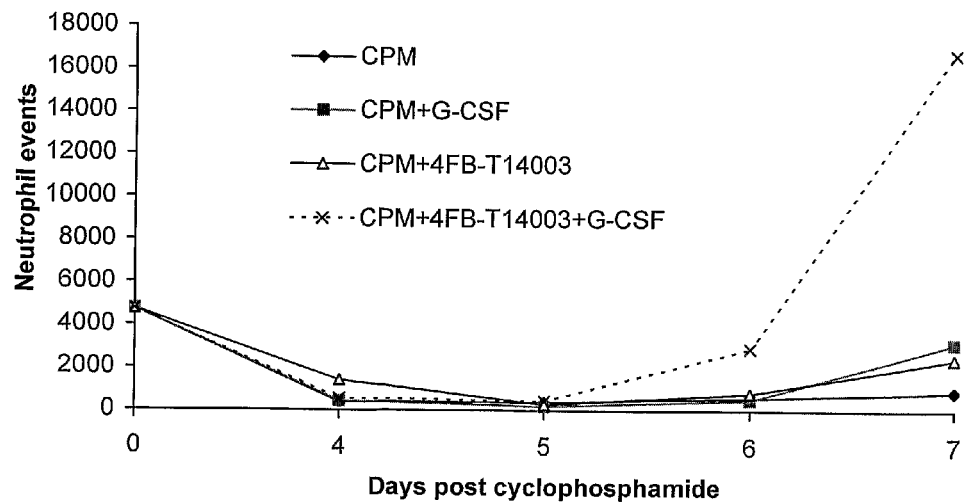
FIG. 12A, the number of neutrophils in the blood sample.
Figure 12B:
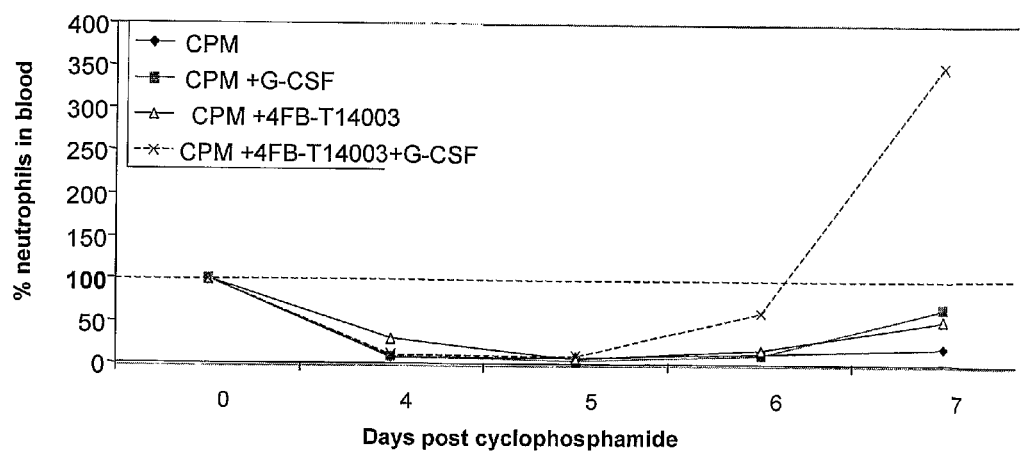
FIG. 12B, the percentage of the neutrophils from the control level in normal, untreated mice.

4F-benzoyl-TN14003 Synergizes with G-CSF in Alleviating Chemotherapy-Induced Neutropenia Neutropenia was induced in female C57BL/6 mice by administration of a total dose of 250 mg/kg cyclophosphamide (CPM) in two 0.5 mL intraperitoneal injections scheduled at day 1 (150 mg/kg) and day 4 (100 mg/kg). The CPM protocol caused 4 days of neutropenia (from day 4 to day 8). When mice were treated with the combination of G-CSF and 4F-benzoyl-TN14003, a significant number of neutrophils was detected in the blood on day 6, as compared to mice that were treated with CPM only or with G-CSF or 4F-benzoyl-TN14003 alone (FIG. 12). The number of neutrophils detected following treatment with a combination of G-CSF and 4F-benzoyl-TN14003 was almost 62% of the initial number of neutrophils in normal (untreated) mice, while other treatments showed only a mild effect. On day 7, the effect of the combination of G-CSF and 4F-benzoyl-TN14003 was even greater, as demonstrated by the ability of this treatment to elevate the number of neutrophils up to 350% from their initial number, while all other treatments were not sufficient to elevate neutrophil counts to their normal level.

In FIG. 12, diamonds represent cyclophosphamide treated mice; squares represent mice treated with cyclophosphamide and G-CSF; triangles represent mice treated with cyclophosphamide and 4F-benzoyl-TN14003; and crosses represent mice treated with cyclophosphamide, 4F-benzoyl-TN14003 and G-CSF.

Example 9

Figure 13A:
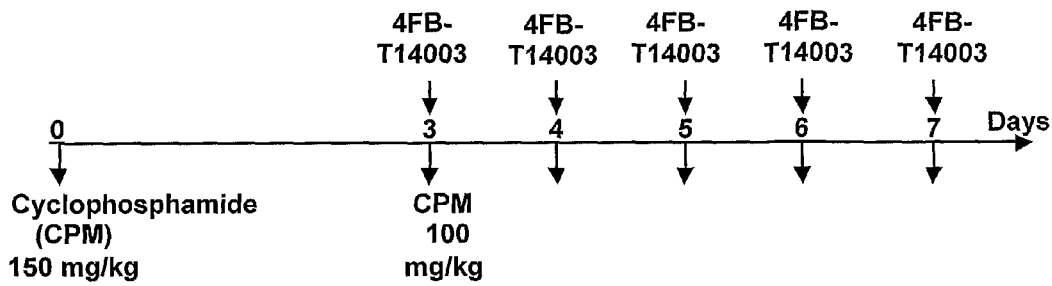
FIG. 13A is a schematic representation of the experimental model.

The Effect of 4F-benzoyl-TN14003 on Granulocyte Counts in a Chemotherapy Model Mice received a total dose of 250 mg/kg cyclophosphamide (CPM) by two 0.25 ml intra-peritoneal injections scheduled at day 0 (150 mg/kg) and day 3 (100 mg/kg). Mice were subcutaneously treated with 0.2 ml of 4F-benzoyl-TN14003 (5 mg/kg) at the indicated time points, as detailed in FIG. 13A. Flow cytometry was used to assess the number of cells in the blood and bone marrow (BM), and distinguish between the different populations. Cells were gated according to forward scatter and side scatter to exclude dead cells and to identify granulocytes (GR-1 positive cells).

Figure 13B:
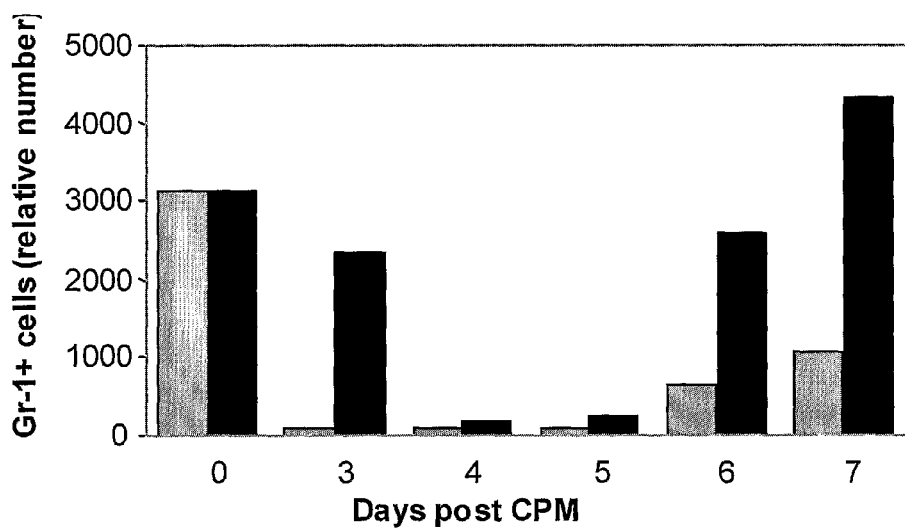
FIG. 13B depicts the relative numbers (relative to untreated WT mice) of granulocytes (GR-1 positive cells) in the blood in mice receiving 250 mg/kg cyclophosphamide (CPM, striped columns) or CPM and 4F-benzoyl-TN14003 (black columns), assessed by flow cytometry.
Figure 13C:
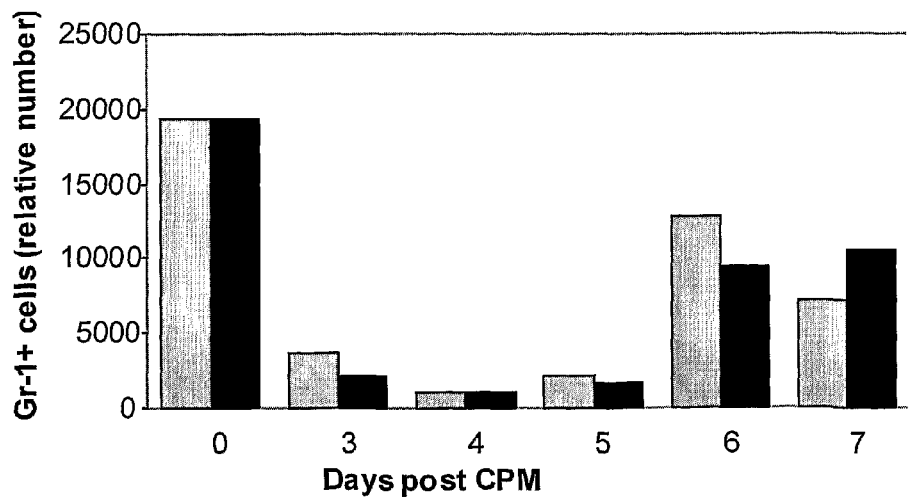
FIG. 13C depicts the relative numbers of granulocytes in the blood in mice receiving CPM (striped columns) or CPM and 4F-benzoyl-TN14003 (black columns).
Figure 13D:
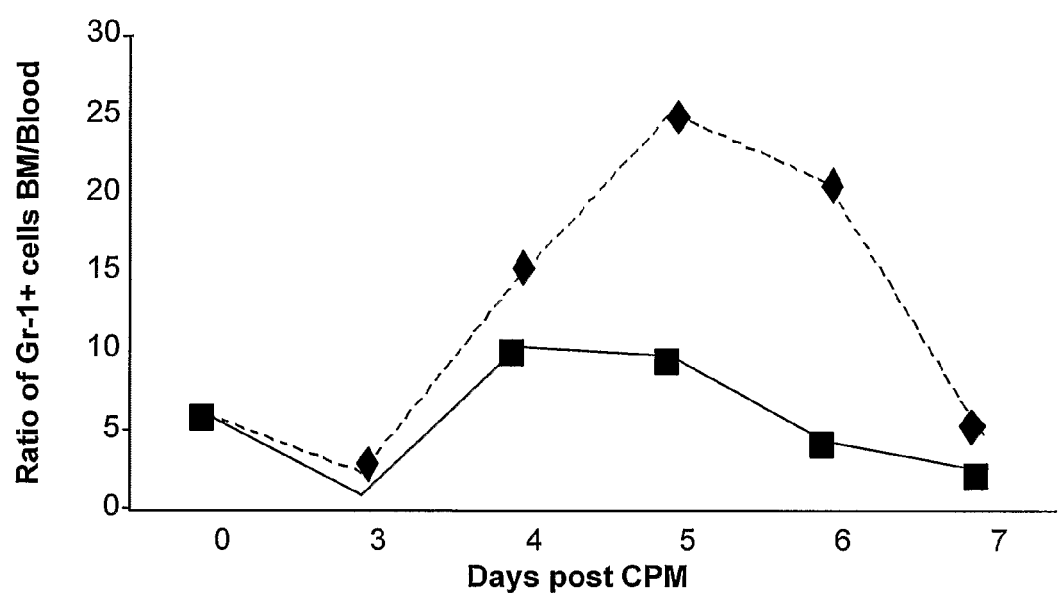
FIG. 13D depicts the ratio of GR-1 positive cells in the blood and BM of mice receiving CPM (diamonds) or CPM and 4F-benzoyl-TN14003 (squares).

The ability of 4F-benzoyl-TN14003 to mobilize GR-1 positive cells to the blood and reduce neutropenia is shown in FIG. 13B, wherein striped columns represent cells obtained from CPM-treated mice and black columns represent cells obtained from mice treated with CPM and 4F-benzoyl-TN14003. The number of GR-1 positive cells in the BM is shown in FIG. 13C, wherein striped columns represent cells obtained from CPM-treated mice and black columns represent cells obtained from mice treated with CPM and 4F-benzoyl-TN14003. The relative numbers of GR-1 positive cells in the blood and BM are shown in FIG. 13D, clearly demonstrating an inhibition of GR-1$^+$ cells release from the BM and the ability of 4F-benzoyl-TN14003 to release cells from the inhibitory effect of the BM stroma. In FIG. 13D, diamonds represent cells obtained from CPM treated mice and squares represent cells obtained from mice treated with CPM and 4F-benzoyl-TN14003.

Example 10

Figure 14A:
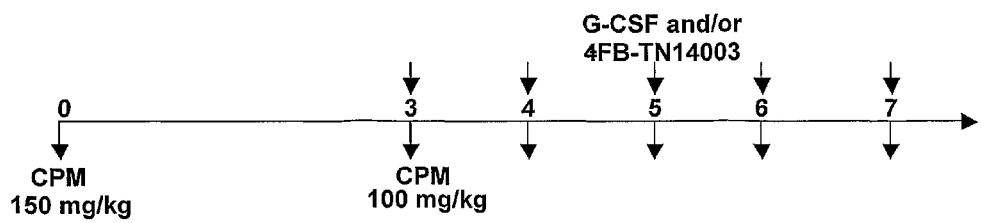
FIG. 14A is a schematic representation of the experimental model.

The Effects of 4F-benzoyl-TN14003 and G-CSF on Granulocyte Counts in a Chemotherapy Model Mice received a total dose of 250 mg/kg CPM by two 0.25 ml intra-peritoneal injections scheduled at day 0 (150 mg/kg) and day 3 (100 mg/kg). Mice were subcutaneously treated with 0.2 ml of 4F-benzoyl-TN14003 (5 mg/kg) or G-CSF 5 µg/mouse or the combination of both at the indicated time points as detailed in FIG. 14A. Flow cytometry was used to assess the number of cells in the blood and bone marrow (BM) and distinguish between the different populations. Cells were gated according to forward scatter and side scatter to exclude dead cells and to determine granulocytes (GR-1 positive cells).

Figure 14B:
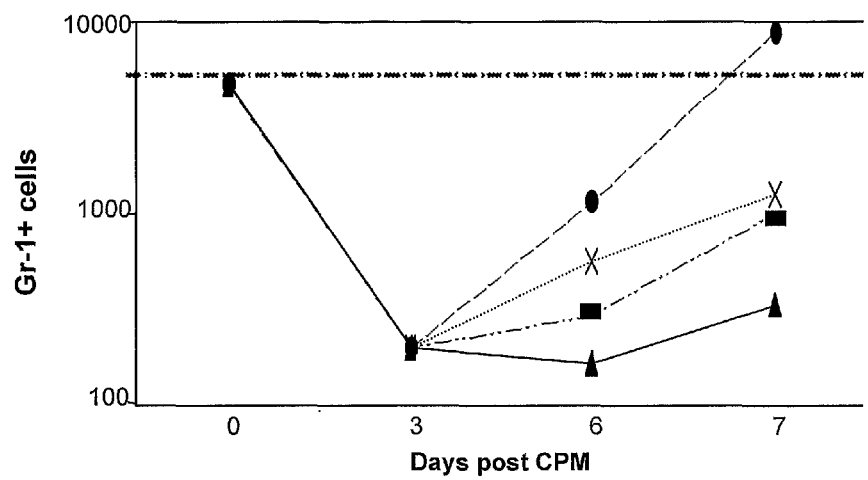
FIG. 14B depicts the relative numbers of granulocytes (GR-1 positive cells) in the blood in mice receiving 250 mg/kg cyclophosphamide (CPM, diamonds), CPM and 4F-benzoyl-TN14003
Figure 14C:
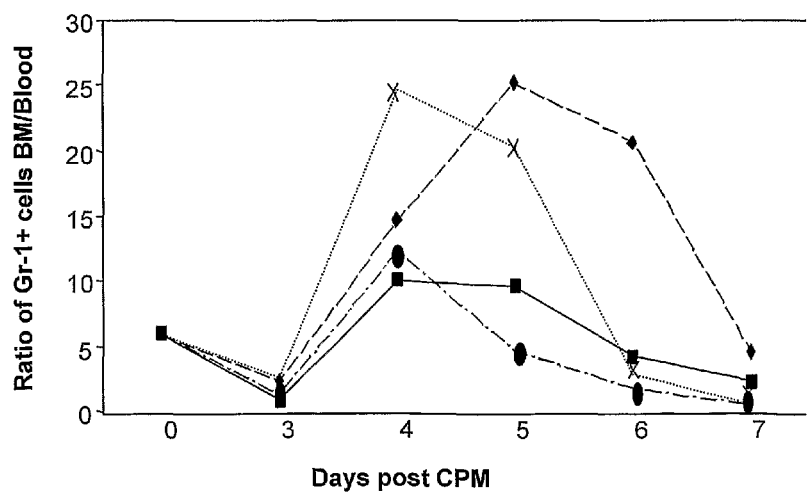
FIG. 14C depicts the ratio of GR-1 positive cells in the blood and BM of mice receiving CPM (diamonds), CPM and 4F-benzoyl-TN14003 (squares), CPM and G-CSF (crosses) or CPM, G-CSF and 4F-benzoyl-TN14003 (circles).

The ability of 4F-benzoyl-TN14003 and G-CSF by themselves or in combination, to mobilize GR-1 positive cells and reduce neutropenia is shown in FIG. 14B. The relative numbers of GR-1 positive cells in the blood and BM are shown in FIG. 14C, clearly demonstrating an inhibition of GR-1 cells release from the BM and the ability of 4F-benzoyl-TN14003 by itself or in combination of G-CSF to release cells from the inhibitory effect of the BM. In FIGS. 14B and 14C, diamonds represent cells obtained from CPM treated mice, squares represent cells obtained from mice treated with CPM and 4F-benzoyl-TN14003, crosses represent cells obtained from mice treated with CPM and G-CSF, and circles represent cells obtained from mice treated with CPM, G-CSF and 4F-benzoyl-TN14003.

Example 11

Figure 15A:
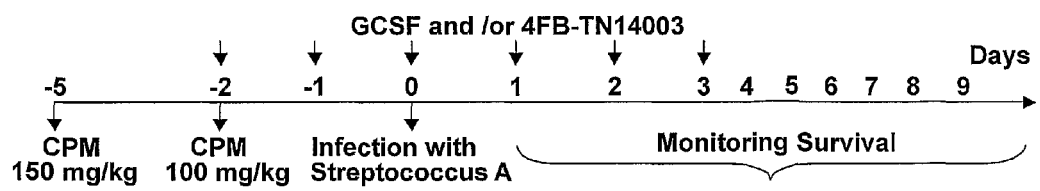
FIG. 15A is a schematic representation of the experimental model.

The Effects of 4F-benzoyl-TN14003 and G-CSF on the Survival of Mice Upon Bacterial Infection in a Chemotherapy Model Mice received a total dose of 250 mg/kg CPM by two 0.25 ml intra-peritoneal injections scheduled at day −5 (150 mg/kg) and day −2 (100 mg/kg). Mice were subcutaneously treated with 0.2 ml of 4F-benzoyl-TN14003 (5 mg/kg), alone or in combination with G-CSF (5 µg/mouse), at the time points indicated in FIG. 15A. On day 0, *Streptococcus* A were subcutaneously injected ($10^8$/mouse) and the mice were then treated as detailed in FIG. 15A.

Figure 15B:
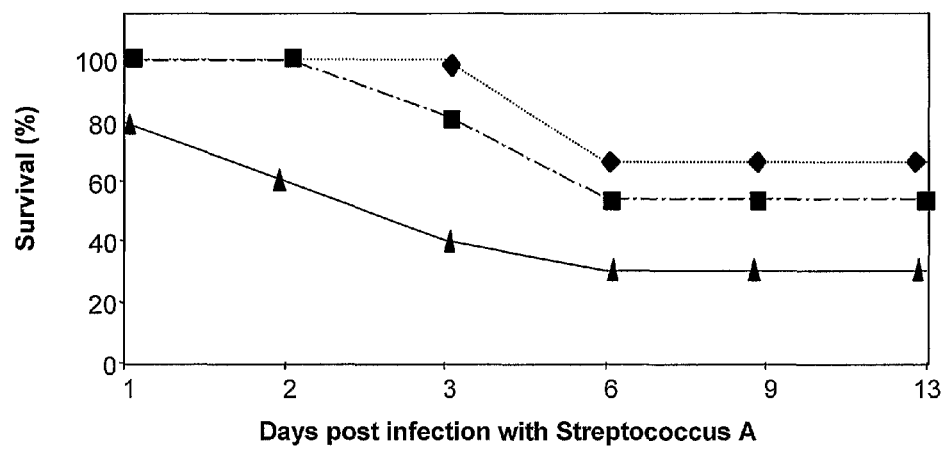
FIG. 15B presents the survival (in %) of control mice (diamonds), CPM treated mice (triangles), and mice treated with CPM and 4F-benzoyl-TN14003 (squares).
Figure 15C:
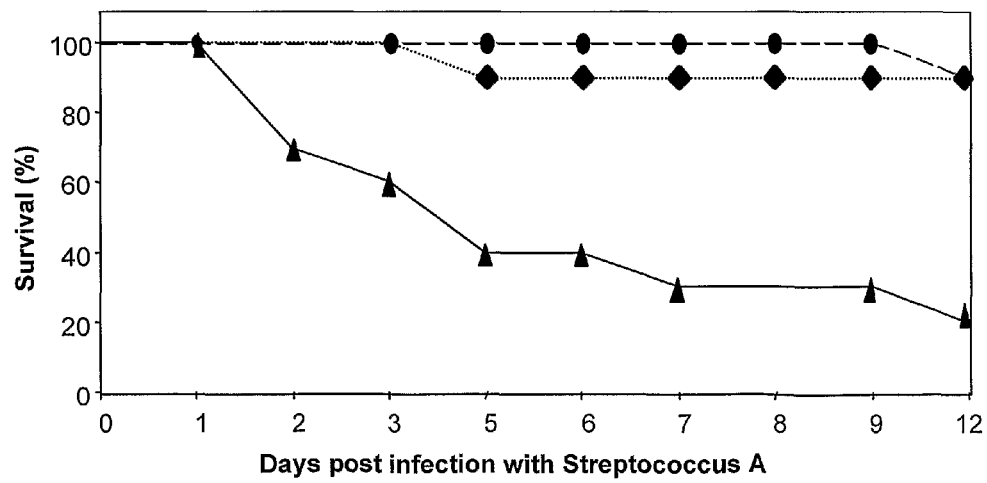
FIG. 15C presents the survival (in %) of control mice (diamonds), CPM treated mice (triangles), and mice treated with CPM, G-CSF and 4F-benzoyl-TN14003 (circles).

The ability of 4F-benzoyl-TN14003 alone or in combination with G-CSF to save the mice from death induced by the pathogen is shown in FIGS. 15B and 15C, wherein diamonds represent survival of control mice, triangles represent survival of CPM treated mice, squares represent survival of mice treated with CPM and 4F-benzoyl-TN14003, and circles represent survival of mice treated with CPM, G-CSF and 4F-benzoyl-TN14003.

Example 12

Figure 16A:
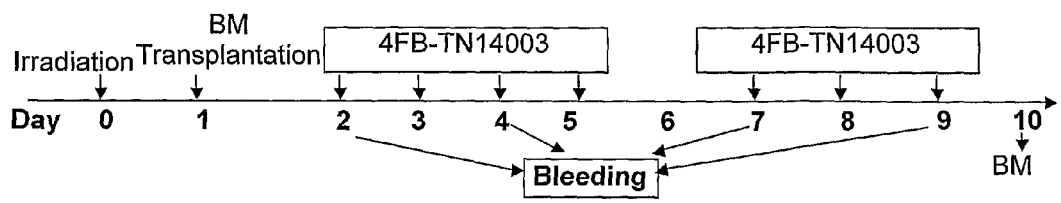
FIG. 16A is a schematic representation of the experimental model.

The Effect of 4F-benzoyl-TN14003 on Cell Counts in a Bone Marrow Transplantation Model Mice received lethal total body irradiations of 900 Rad and were subsequently transplanted with BM cells from donor healthy mice ($5 \times 10^6$/mouse). Mice were then subcutaneously treated with 0.2 ml of 4F-benzoyl-TN14003 (5 mg/kg) at different time points, as indicated in FIG. 16A. Flow cytometry was used to assess the number of cells in the blood and bone marrow (BM), and distinguish between the different populations. Cells were gated according to forward scatter and side scatter to exclude dead cells and to determine granulocytes (GR-1 positive cells) and mononuclear cells (MNC).

Figure 16B:
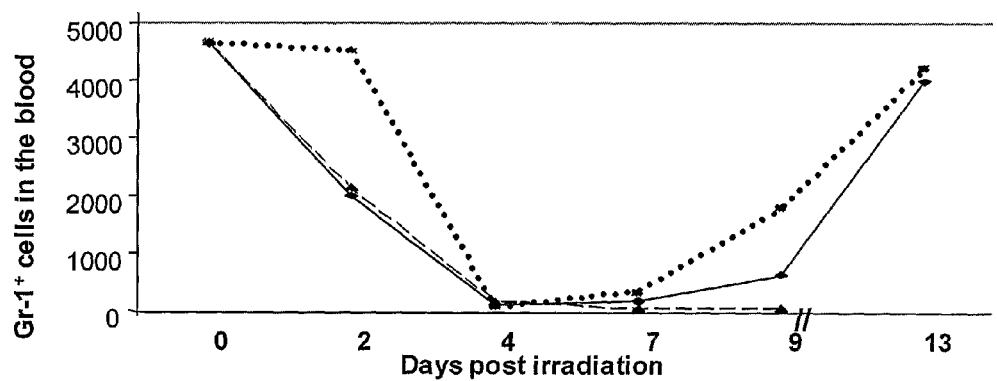
FIG. 16B presents the numbers of GR-1 positive cells in the blood of control mice (full line), irradiated mice (dashed line) and irradiated mice treated with 4F-benzoyl-TN14003 (dotted line).
Figure 16C:
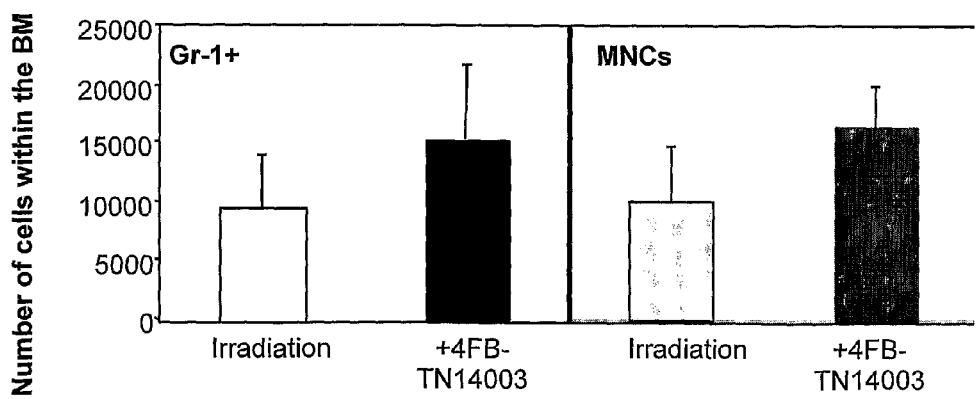
FIG. 16C depicts GR-1 (left panel) and MNC (right panel) cell counts in the BM of the mice.

The ability of 4F-benzoyl-TN14003 to mobilize GR-1 positive cells and reduce neutropenia is shown in FIG. 16B, wherein the full line indicates untreated mice, the dashed line indicates irradiated mice and the dotted line indicates irradiated mice treated with 4F-benzoyl-TN14003. The ability of 4F-benzoyl-TN14003 to stimulate GR-1 (left panel) and MNC (right panel) production in the BM is shown in FIG. 16C.

Figure 16D:
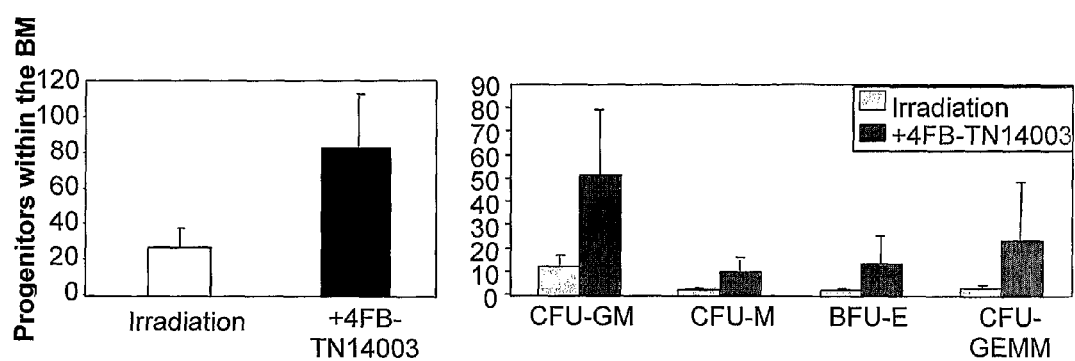
FIG. 16D shows the number of total progenitor cell counts (left panel) or counts of CFU-GM, CFU-M, BFU-E and CFU-GEMM in BM of irradiated mice and irradiated mice treated with 4F-benzoyl-TN14003.

The ability of 4F-benzoyl-TN14003 to stimulate production of various progenitors in the BM is shown in FIG. 16D. These results clearly demonstrate the ability of 4F-benzoyl-TN14003 to induce production of cells in the BM of transplanted mice. In FIG. 16D, the left panel depicts total progenitor cell counts in BM of irradiated mice (white column) and irradiated mice treated with 4F-benzoyl-TN14003 (black column); the right panel depicts counts of CFU-GM, CFU-M, BFU-E and CFU-GEMM in BM of irradiated mice (vertically striped columns) and irradiated mice treated with 4F-benzoyl-TN14003 (diagonally striped columns).

Example 13

In Vitro Production of Progenitors and Mature Cells

Figure 17A:
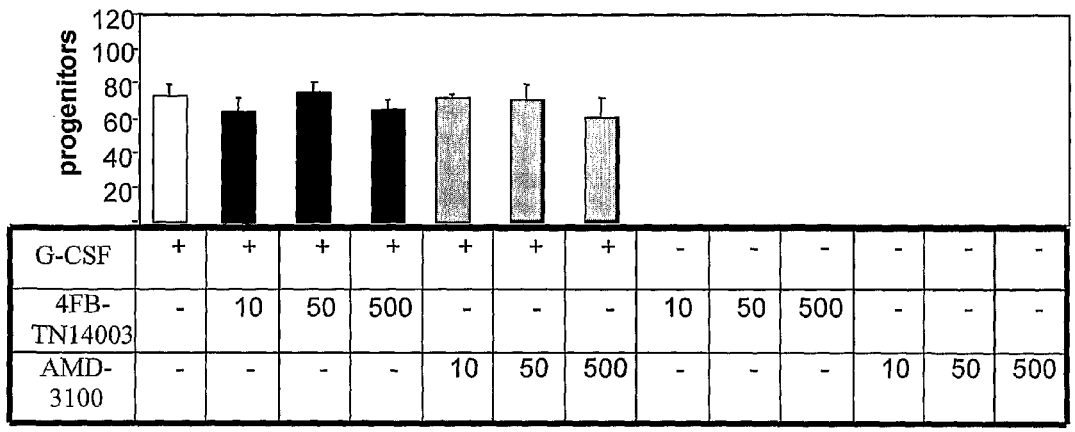
FIG. 17A, the number of progenitor cells produced upon in vitro incubation of 4F-benzoyl-TN14003, G-CSF and/or AMD3100 with progenitor cells in the absence of stromal cells.

In order to evaluate the number of progenitor cells, a colony-forming cell assay was used. Burst forming units erythrocyte (BFU-E), colony forming units granulocyte-macrophage (CFU-GM), colony forming units megakaryocytes (CFU-M), and colony forming units granulocyte-erythrocyte-monocyte-macrophage (CFU-GEMM) were assayed by plating the cells ($10^5$/ml) in Iscove's-modified Dulbecco's Medium (IMDM) containing 1% methylcellulose, 15% FBS, 1% bovine serum albumin (BSA), and 4F-benzoyl-TN14003 by itself (10-500 ng/ml) or in combination with G-CSF (in concentrations of 10-500 ng/ml). As can be seen in FIG. 17A, 4F-benzoyl-TN14003 by itself or in combination with G-CSF did not stimulate the production of colonies in vitro.

Figure 17B:
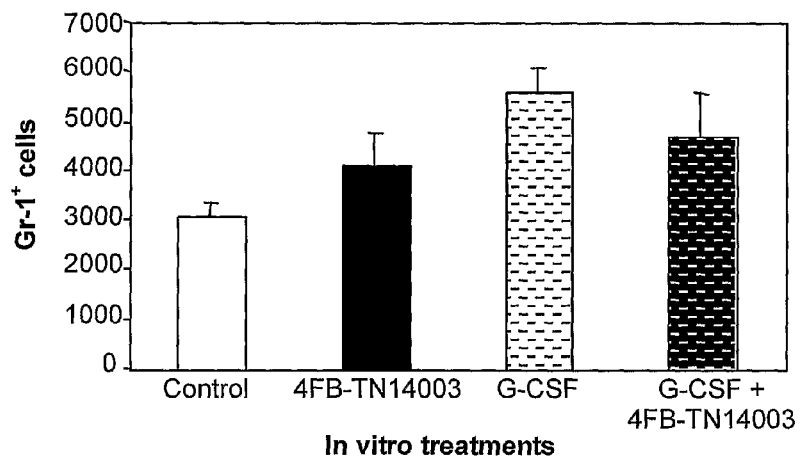
FIG. 17B, the number of Gr-1$^+$ cells produced upon in vitro incubation 4F-benzoyl-TN14003, G-CSF and/or AMD3100 with progenitor cells and stromal cells.
Figure 17C:
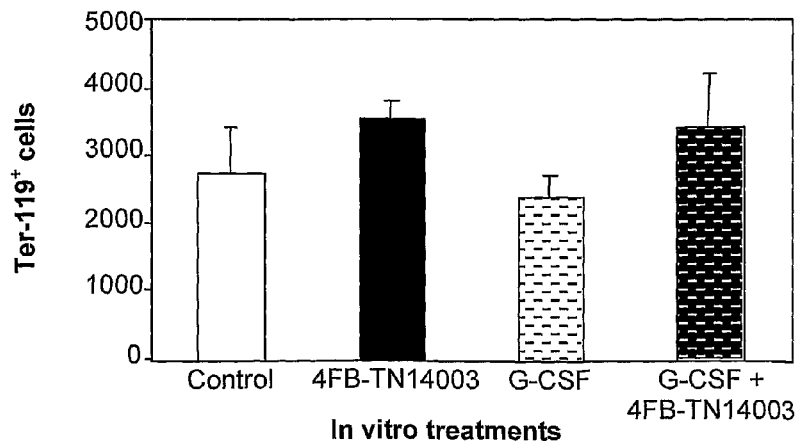
FIG. 17C, the number of Ter-119$^+$ cells produced upon in vitro incubation 4F-benzoyl-TN14003, G-CSF and/or AMD3100 with progenitor cells and stromal cells.
Figure 17D:
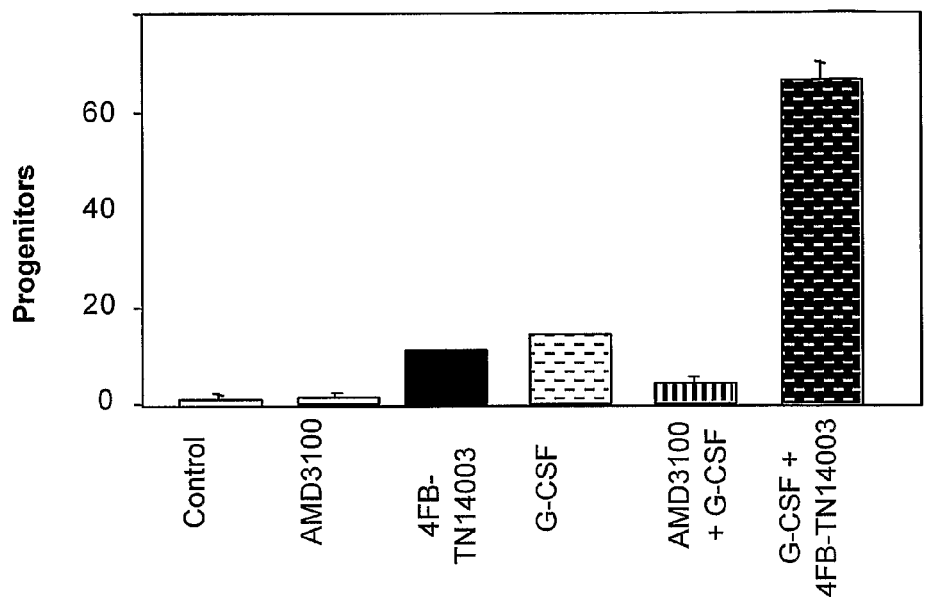
FIG. 17D, the number of progenitor cells produced upon in vitro incubation 4F-benzoyl-TN14003, G-CSF and/or AMD3100 with progenitor cells and stromal cells.

However, when 4F-benzoyl-TN14003 by itself (10 microgram/ml) or in combination of G-CSF (100 ng/ml) were added to stromal cells (14F1.1) seeded with BM cells ($5 \times 10^5$/plate), both treatments stimulated the production of GR-1 and Ter119 positive cells as well as progenitors, as demonstrated in FIGS. 17B-17D, respectively. More specifically, the number of colonies was assayed by collecting the cells ($10^5$/plate) 4 days after treatment form the treated and control (untreated) plates, and evaluating the number of progenitor cells using a colony-forming cell assay. Burst forming units erythrocyte (BFU-E), colony forming units granulocyte-macrophage (CFU-GM), colony forming units megakaryocytes (CFU-M), and colony forming units granulocyte-erythrocyte-monocyte-macrophage (CFU-GEMM) were assayed by plating the cells in Iscove's-modified Dulbecco's Medium (IMDM) containing 1% methylcellulose, 15% FBS, 1% bovine serum albumin (BSA), 3 U/mL rh EPO, 104 M 2-mercaptoethanol, 2 mM L-glutamine, 50 ng/mL rmSCF, 10 ng/mL rmIL-3, 10 mg/mL rh Insulin, 10 ng/mL rh IL-6, and 200 mg/mL Human Transferrin (Methocult GF M3434; StemCell Technologies Inc.). The cultures were incubated at 37° C. in a humidified atmosphere containing 5% $CO_2$. Seven days later, typical colonies were visually scored by morphologic criteria using a light microscope and the frequency of CFU was calculated. Staining colonies with benzidine dihydrochloride (Sigma, Israel) was used to localize hemoglobin-containing cells. As shown in FIG. 17D, AMD3100 did not demonstrate this effect.

Figure 17E:
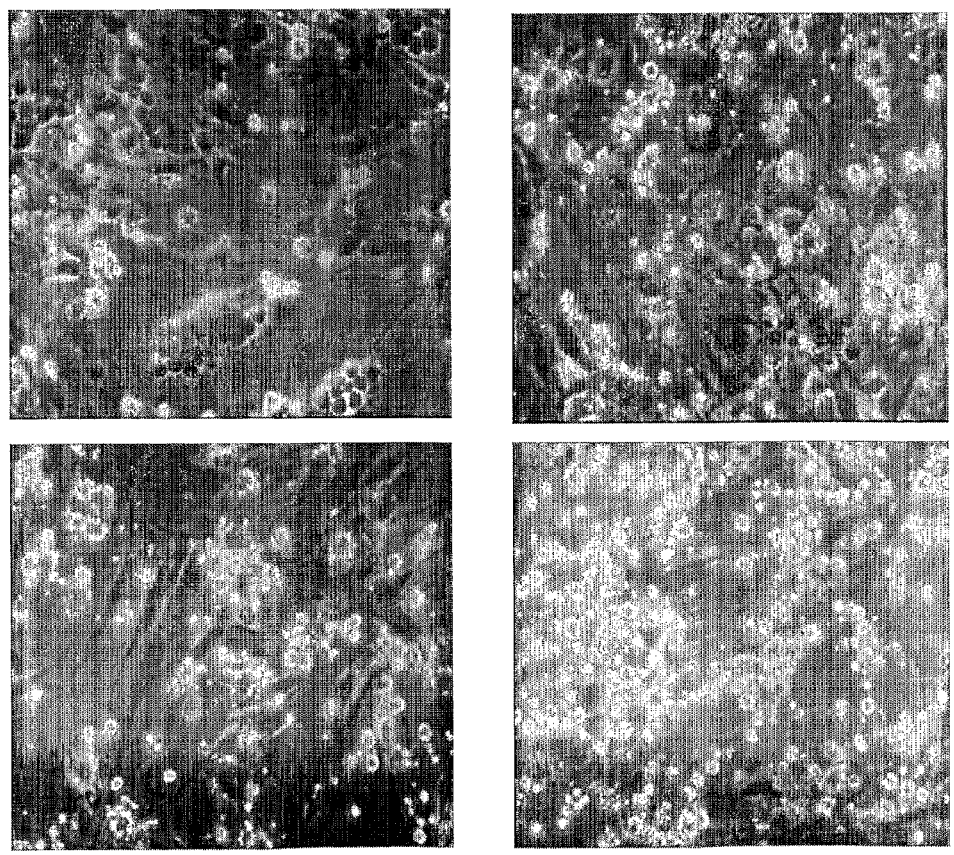
FIG. 17E, micrographs of a colony forming assay wherein 4F-benzoyl-TN14003, G-CSF and/or AMD3100 were incubated in vitro with progenitor cells and stromal cells.

FIG. 17E presents micrographs of a representative experiment. The top left panel shows that when BM cells are seeded on top of stromal cells they form cobblestone areas with limited proliferation and differentiation. The top right panel shows BM cells differentiating and proliferating after treated with 4F-benzoyl-TN14003; the bottom left panel shows BM cells differentiating and proliferating after treatment with G-CSF; and the bottom right panel shows BM cells differentiating and proliferating after treatment with G-CSF and 4F-benzoyl-TN14003.

REFERENCES

Avniel, S. et al., *J. Invest. Dermatol.* 2006, 126(2): 468-76.
Balkwill, F. Semi. in *Canc. Biol.* 2004, 14: 171-179.
Broxmeyer, H. E. et al., *J. Exp. Med.* 2005, 201(8): 1307-1318.
Dar, A. et al., *Nat. Immunol.* 2005. 6(10): 1038-1046.
Flomenberg, N. et al., *Blood,* 2005, 106(5): 1867-1874.

Kim, C. H. and Broxmeyer H. E., *Blood,* 1998, 91(1): 100-110.
Kollet, O. et al., *Blood,* 2002, 100(8): 2778-2786.
Lack, N. A. et al., *Clin. Pharmacol. Ther.* 2005, 77(5): 427-436.
Lapidot, T. and Kollet, O., *Leukemia,* 2002 16(10): 1992-2003.
Lapidot, T. et al., *Blood,* 2005, 106(6): 1901-1910.
Levesque, J. P. et al., *J. Clin. Invest.* 2003, 111(2): 187-196.
Martin, C. et al., *Immunity,* 2003, 19(4): 583-593.
Muller, A. et al., *Nature,* 2001, 410: 50-56.
Nagasawa, T. et al., *Proc. Nat. Aca. Sci.* 1994, 91: 2305-2309.
Peled, A., et al., *Science,* 1999, 283(5403): 845-848.
Phillips, R. et al., *Amer. J. Respir. Critic. Care Med.* 2003, 167: 1676-1686.
Princen, K. and Schols, D., *Cytokine Grow. Fac. Rev.* 2005, 16(6): 659-677.
Rossi, D. and Zlotnik, A., *Ann. Rev. Immun.* 2000, 18: 217-242.
Tamamura, H. et al., *Biochem. Biophys. Res. Commun.* 1998, 253(3): 877-882.
Tamamura, H. et al., *Org. Biomol. Chem.* 2003, 1: 3663-3669.
Tamamura, H. and Fujii, N., *Expert Opin. Ther. Targets,* 2005, 9(6): 1267-1282.
Zuluaga A F, et al. *BMC Infect Dis.* 2006 Mar. 17; 6: 55.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

SEQUENCE LISTING

```
<160> NUMBER OF SEQ ID NOS: 77

<210> SEQ ID NO 1
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 1

Xaa Arg Xaa Cys Tyr Xaa Lys Xaa Pro Tyr Arg Xaa Cys Arg
1               5                   10

<210> SEQ ID NO 2
<211> LENGTH: 14
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
```

-continued

<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 2

Arg Arg Xaa Cys Tyr Xaa Lys Xaa Pro Tyr Arg Xaa Cys Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATION
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 3

Arg Arg Xaa Cys Tyr Arg Lys Xaa Pro Tyr Arg Xaa Cys Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 4

Arg Arg Xaa Cys Tyr Xaa Lys Xaa Pro Tyr Arg Xaa Cys Arg
1               5                   10

```
<210> SEQ ID NO 5
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 5

Arg Arg Xaa Cys Tyr Xaa Lys Xaa Pro Tyr Xaa Xaa Cys Arg
1               5                   10

<210> SEQ ID NO 6
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 6

Xaa Arg Xaa Cys Tyr Xaa Lys Xaa Pro Tyr Arg Xaa Cys Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' acetylated citrulline
<220> FEATURE:
<221> NAME/KEY: MOD_RES
```

```
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 7

Xaa Arg Xaa Cys Tyr Arg Lys Xaa Pro Tyr Arg Xaa Cys Arg
1               5                   10

<210> SEQ ID NO 8
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
<223> OTHER INFORMATION: citrulline

<400> SEQUENCE: 8

Arg Arg Xaa Cys Tyr Arg Lys Xaa Pro Tyr Xaa Xaa Cys Arg
1               5                   10

<210> SEQ ID NO 9
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline

<400> SEQUENCE: 9

Xaa Arg Xaa Cys Tyr Arg Lys Xaa Pro Tyr Xaa Xaa Cys Arg
1               5                   10

<210> SEQ ID NO 10
<211> LENGTH: 14
<212> TYPE: PRT
<213> ORGANISM: Artificial Sequence
<220> FEATURE:
```

-continued

```
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 10

Arg Arg Xaa Cys Tyr Xaa Lys Xaa Pro Tyr Arg Xaa Cys Arg
1               5                  10

<210> SEQ ID NO 11
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 11

Arg Arg Xaa Cys Tyr Xaa Lys Xaa Pro Tyr Xaa Xaa Cys Arg
1               5                  10

<210> SEQ ID NO 12
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
```

```
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: AMIDATED

<400> SEQUENCE: 12

Xaa Arg Xaa Cys Tyr Xaa Lys Xaa Pro Tyr Arg Xaa Cys Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 13

Xaa Arg Xaa Cys Tyr Arg Lys Xaa Pro Tyr Arg Xaa Cys Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (11)..(12)
```

```
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 14

Arg Arg Xaa Cys Tyr Arg Lys Xaa Pro Tyr Xaa Xaa Cys Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (11)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 15

Xaa Arg Xaa Cys Tyr Arg Lys Xaa Pro Tyr Xaa Xaa Cys Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 16

Xaa Arg Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 17

Arg Glu Xaa Cys Tyr Arg Lys Xaa Pro Tyr Arg Xaa Cys Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 18

Arg Arg Xaa Cys Tyr Glu Lys Xaa Pro Tyr Arg Xaa Cys Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 19

Arg Arg Xaa Cys Tyr Arg Glu Xaa Pro Tyr Arg Xaa Cys Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
```

```
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline

<400> SEQUENCE: 20

Arg Arg Xaa Cys Tyr Arg Lys Xaa Pro Tyr Arg Xaa Cys Arg
1               5                   10

<210> SEQ ID NO 21
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 21

Arg Arg Xaa Cys Tyr Arg Lys Xaa Pro Tyr Glu Xaa Cys Arg
1               5                   10

<210> SEQ ID NO 22
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 22

Arg Arg Xaa Cys Tyr Arg Lys Xaa Pro Tyr Arg Xaa Cys Glu
1               5                   10

<210> SEQ ID NO 23
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
```

<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 23

Arg Arg Xaa Cys Tyr Xaa Lys Xaa Pro Tyr Arg Xaa Cys Arg
1               5                   10

<210> SEQ ID NO 24
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 24

Arg Arg Xaa Cys Tyr Xaa Lys Xaa Pro Tyr Arg Xaa Cys Arg
1               5                   10

<210> SEQ ID NO 25
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: D-glutamic acid
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 25

Arg Arg Xaa Cys Tyr Xaa Lys Xaa Pro Tyr Arg Xaa Cys Arg

<210> SEQ ID NO 26
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 26

Xaa Arg Xaa Cys Tyr Xaa Lys Xaa Pro Tyr Arg Xaa Cys Arg
1               5                   10

<210> SEQ ID NO 27
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 27

Arg Arg Xaa Cys Tyr Xaa Lys Xaa Pro Xaa Arg Xaa Cys Arg
1               5                   10

<210> SEQ ID NO 28
<211> LENGTH: 14
<212> TYPE: PRT

```
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 28

Arg Arg Xaa Cys Tyr Xaa Lys Xaa Pro Tyr Arg Xaa Cys Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED D-glutamic acid
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 29

Xaa Arg Xaa Cys Tyr Xaa Lys Xaa Pro Tyr Arg Xaa Cys Arg
1               5                   10

<210> SEQ ID NO 30
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
```

```
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (10)..(10)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 30

Arg Arg Xaa Cys Tyr Xaa Lys Xaa Pro Xaa Arg Xaa Cys Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: D-glutamic acid
<220> FEATURE:
<221> NAME/KEY: MOD_RES
<222> LOCATION: (14)..(14)
<223> OTHER INFORMATION: c' amidated

<400> SEQUENCE: 31

Arg Arg Xaa Cys Tyr Xaa Lys Xaa Pro Tyr Arg Xaa Cys Arg
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
```

```
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 32

Arg Arg Xaa Cys Tyr Xaa Lys Xaa Pro Tyr Arg Xaa Cys Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 33

Xaa Arg Xaa Cys Tyr Xaa Lys Xaa Pro Tyr Arg Xaa Cys Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
```

```
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 34

Xaa Arg Xaa Cys Tyr Xaa Lys Xaa Pro Tyr Arg Xaa Cys Arg
1               5                   10

<210> SEQ ID NO 35
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tetramethylguanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 35

Xaa Xaa Cys Tyr Xaa Lys Xaa Pro Tyr Arg Xaa Cys Arg
1               5                   10

<210> SEQ ID NO 36
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
```

```
<221> NAME/KEY: MOD_RES
<222> LOCATION: (14)..(14)
<223> OTHER INFORMATION: amidated

<400> SEQUENCE: 36

Xaa Arg Xaa Cys Tyr Xaa Lys Xaa Pro Tyr Arg Xaa Cys Arg
1               5                   10

<210> SEQ ID NO 37
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 37

Xaa Arg Xaa Cys Tyr Xaa Lys Xaa Pro Tyr Arg Xaa Cys Arg
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 5-aminopentanoyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 38
```

Xaa Xaa Cys Tyr Xaa Lys Xaa Pro Tyr Arg Xaa Cys Arg
1               5                   10

<210> SEQ ID NO 39
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 2-desamino-arginyl
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 39

Xaa Arg Xaa Cys Tyr Xaa Lys Xaa Pro Tyr Arg Xaa Cys Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 40

Xaa Xaa Cys Tyr Xaa Lys Xaa Pro Tyr Arg Xaa Cys Arg
1               5                   10

<210> SEQ ID NO 41
<211> LENGTH: 13

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Succinyl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 41

Xaa Xaa Cys Tyr Xaa Lys Xaa Pro Tyr Arg Xaa Cys Arg
1               5                   10

<210> SEQ ID NO 42
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Glutaryl-arginine
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 42

Xaa Xaa Cys Tyr Xaa Lys Xaa Pro Tyr Arg Xaa Cys Arg
1               5                   10

<210> SEQ ID NO 43
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
```

```
<222> LOCATION: (1)..(1)
<223> OTHER INFORMATION: desaminoTMG-APA (formula IV in the
      specification)
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 43

Xaa Arg Xaa Cys Tyr Xaa Lys Xaa Pro Tyr Arg Xaa Cys Arg
1               5                   10

<210> SEQ ID NO 44
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: R-CH2 - formula (V) in the specification
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: c' amidated

<400> SEQUENCE: 44

Xaa Arg Xaa Cys Tyr Xaa Lys Xaa Pro Tyr Arg Xaa Cys Arg
1               5                   10

<210> SEQ ID NO 45
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: 3-((2-naphthyl) alanine
<220> FEATURE:
<221> NAME/KEY: MOD_RES
<222> LOCATION: (5)..(5)
```

```
<223> OTHER INFORMATION: citrulline
<220> FEATURE:
<221> NAME/KEY: MOD_RES
<222> LOCATION: (7)..(7)
<223> OTHER INFORMATION: D-glutamic acid
<220> FEATURE:
<221> NAME/KEY: MOD_RES
<222> LOCATION: (11)..(11)
<223> OTHER INFORMATION: citrulline
<220> FEATURE:
<221> NAME/KEY: MOD_RES
<222> LOCATION: (13)..(13)
<223> OTHER INFORMATION: c' amidated

<400> SEQUENCE: 45

Arg Xaa Cys Tyr Xaa Lys Xaa Pro Tyr Arg Xaa Cys Arg
1               5                   10

<210> SEQ ID NO 46
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: tetramethylguanyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 46

Xaa Arg Xaa Cys Tyr Xaa Lys Xaa Pro Tyr Arg Xaa Cys Arg
1               5                   10

<210> SEQ ID NO 47
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
```

```
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 47

Xaa Arg Xaa Cys Tyr Xaa Lys Xaa Pro Tyr Arg Xaa Cys Arg
1               5                   10

<210> SEQ ID NO 48
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 6-aminohexanoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 48

Xaa Arg Xaa Cys Tyr Arg Lys Xaa Pro Tyr Arg Xaa Cys Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 49

Arg Arg Xaa Cys Tyr Xaa Arg Xaa Pro Tyr Arg Xaa Cys Arg
1               5                   10

<210> SEQ ID NO 50
<211> LENGTH: 14
<212> TYPE: PRT
<213> ORGANISM: Artificial Sequence
```

```
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' amidated

<400> SEQUENCE: 50

Arg Arg Xaa Cys Tyr Xaa Arg Xaa Pro Tyr Arg Xaa Cys Arg
1               5                   10

<210> SEQ ID NO 51
<211> LENGTH: 14
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (1)..(1)
<223> OTHER INFORMATION: N' ACETYLATED
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 51

Arg Arg Xaa Cys Tyr Xaa Lys Xaa Pro Tyr Arg Xaa Cys Arg
1               5                   10

<210> SEQ ID NO 52
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: N' ACETYLATED
```

```
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 52

Arg Arg Xaa Cys Tyr Arg Lys Xaa Pro Tyr Arg Xaa Cys Arg
1               5                   10

<210> SEQ ID NO 53
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-methyl group

<400> SEQUENCE: 53

Xaa Arg Xaa Cys Tyr Xaa Lys Xaa Pro Tyr Arg Xaa Cys Arg
1               5                   10

<210> SEQ ID NO 54
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
```

```
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by a NH-ethyl group

<400> SEQUENCE: 54

Xaa Arg Xaa Cys Tyr Xaa Lys Xaa Pro Tyr Arg Xaa Cys Arg
1               5                   10

<210> SEQ ID NO 55
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
<220> FEATURE:
<221> NAME/KEY: MISC_FEATURE
<222> LOCATION: (14)..(14)
<223> OTHER INFORMATION: derivatization by NH-isopropyl

<400> SEQUENCE: 55

Xaa Arg Xaa Cys Tyr Xaa Lys Xaa Pro Tyr Arg Xaa Cys Arg
1               5                   10

<210> SEQ ID NO 56
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-fluorobenzoyl-arginine
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-glutamic acid
<220> FEATURE:
<221> NAME/KEY: MOD_RES
<222> LOCATION: (12)..(12)
<223> OTHER INFORMATION: citrulline
```

```
<220> FEATURE:
<221> NAME/KEY: MISC_FEATURE
<222> LOCATION: (14)..(14)
<223> OTHER INFORMATION: derivatization with a tyramine residue

<400> SEQUENCE: 56

Xaa Arg Xaa Cys Tyr Xaa Lys Xaa Pro Tyr Arg Xaa Cys Arg
1               5                   10

<210> SEQ ID NO 57
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 57

Ala Arg Xaa Cys Tyr Arg Lys Xaa Pro Tyr Arg Xaa Cys Arg
1               5                   10

<210> SEQ ID NO 58
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 58

Arg Arg Xaa Cys Tyr Ala Lys Xaa Pro Tyr Arg Xaa Cys Arg
1               5                   10

<210> SEQ ID NO 59
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
```

```
<400> SEQUENCE: 59

Arg Arg Xaa Cys Tyr Arg Ala Xaa Pro Tyr Arg Xaa Cys Arg
1               5                   10

<210> SEQ ID NO 60
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-alanine
<220> FEATURE:
<221> NAME/KEY: MOD_RES
<222> LOCATION: (12)..(12)
<223> OTHER INFORMATION: citrulline

<400> SEQUENCE: 60

Arg Arg Xaa Cys Tyr Arg Lys Xaa Pro Tyr Arg Xaa Cys Arg
1               5                   10

<210> SEQ ID NO 61
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 61

Arg Arg Xaa Cys Tyr Arg Lys Xaa Ala Tyr Arg Xaa Cys Arg
1               5                   10

<210> SEQ ID NO 62
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 62

Arg Arg Xaa Cys Tyr Arg Lys Xaa Pro Ala Arg Xaa Cys Arg
1               5                   10
```

<210> SEQ ID NO 63
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 63

Arg Arg Xaa Cys Tyr Arg Lys Xaa Pro Tyr Ala Xaa Cys Arg
1               5                   10

<210> SEQ ID NO 64
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 64

Xaa Arg Xaa Cys Tyr Arg Lys Xaa Pro Tyr Arg Xaa Cys Arg
1               5                   10

<210> SEQ ID NO 65
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 65

Arg Arg Xaa Cys Tyr Xaa Lys Xaa Pro Tyr Arg Xaa Cys Arg
1               5                   10

<210> SEQ ID NO 66
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 66

Arg Arg Xaa Cys Tyr Xaa Lys Xaa Pro Tyr Arg Xaa Cys Arg
1               5                   10

<210> SEQ ID NO 67
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (7)..(7)
<223> OTHER INFORMATION: citrulline
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 67

Arg Arg Xaa Cys Tyr Arg Xaa Xaa Pro Tyr Arg Xaa Cys Arg
1               5                   10

<210> SEQ ID NO 68
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline

```
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' AMIDATED

<400> SEQUENCE: 68

Arg Arg Xaa Cys Tyr Xaa Lys Xaa Pro Tyr Arg Xaa Cys Arg
1               5                   10

<210> SEQ ID NO 69
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-lysine
<220> FEATURE:
<221> NAME/KEY: MOD_RES
<222> LOCATION: (12)..(12)
<223> OTHER INFORMATION: citrulline

<400> SEQUENCE: 69

Arg Arg Xaa Cys Tyr Arg Lys Xaa Pro Tyr Arg Xaa Cys Arg
1               5                   10

<210> SEQ ID NO 70
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (6)..(6)
<223> OTHER INFORMATION: citrulline
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 70

Arg Arg Xaa Cys Tyr Xaa Lys Xaa Pro Tyr Arg Xaa Cys Arg
1               5                   10

<210> SEQ ID NO 71
<211> LENGTH: 14
<212> TYPE: PRT
<213> ORGANISM: Artificial Sequence
<220> FEATURE:
<223> OTHER INFORMATION: synthetic peptide
<220> FEATURE:
```

```
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline

<400> SEQUENCE: 71

Arg Arg Xaa Cys Tyr Arg Lys Xaa Pro Tyr Arg Xaa Cys Arg
 1               5                  10

<210> SEQ ID NO 72
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: citrulline
<220> FEATURE:
<221> NAME/KEY: MOD_RES
<222> LOCATION: (3)..(3)
<223> OTHER INFORMATION: 3-((2-naphthyl) alanine
<220> FEATURE:
<221> NAME/KEY: MOD_RES
<222> LOCATION: (8)..(8)
<223> OTHER INFORMATION: D-citrulline
<220> FEATURE:
<221> NAME/KEY: MOD_RES
<222> LOCATION: (12)..(12)
<223> OTHER INFORMATION: citrulline
<220> FEATURE:
<221> NAME/KEY: MOD_RES
<222> LOCATION: (14)..(14)
<223> OTHER INFORMATION: C' Amidated

<400> SEQUENCE: 72

Xaa Arg Xaa Cys Tyr Arg Lys Xaa Pro Tyr Arg Xaa Cys Arg
 1               5                  10

<210> SEQ ID NO 73
<211> LENGTH: 14
<212> TYPE: PRT
<213> ORGANISM: Artificial Sequence
<220> FEATURE:
<223> OTHER INFORMATION: SYNTHETIC FORMULA PEPTIDE
<220> FEATURE:
<221> NAME/KEY: MISC_FEATURE
<222> LOCATION: (1)..(1)
<223> OTHER INFORMATION: Xaa is Arg, Lys, ornithine, citrulline, Ala or
     Glu which may be derivatized at the N-terminal, or is absent.
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: When Xaa of (1) is Arg, Lys, ornithine,
     citrulline, Ala or Glu which may be derivatized at the N-terminal,
     Xaa is Arg or Glu, and when Xaa of (1) is absent, Xaa is Arg or
     Glu which may be derivatized at the N-terminal
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: DISULFID
<222> LOCATION: (4)..(13)
```

```
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(6)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (7)..(7)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (8)..(8)
<223> OTHER INFORMATION: Xaa is Pro, Gly, ornithine, Lys, Ala,
      citrulline, Arg or Glu.
<220> FEATURE:
<221> NAME/KEY: MISC_FEATURE
<222> LOCATION: (9)..(9)
<223> OTHER INFORMATION: Xaa is Pro, Gly, ornithine, Lys, Ala,
      citrulline or Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu.
<220> FEATURE:
<221> NAME/KEY: MISC_FEATURE
<222> LOCATION: (11)..(11)
<223> OTHER INFORMATION: Xaa is Arg, Lys, ornithine, citrulline, Ala or
      Glu.
<220> FEATURE:
<221> NAME/KEY: MISC_FEATURE
<222> LOCATION: (12)..(12)
<223> OTHER INFORMATION: Xaa is Arg, Lys, citrulline or Glu.
<220> FEATURE:
<221> NAME/KEY: MISC_FEATURE
<222> LOCATION: (14)..(14)
<223> OTHER INFORMATION: Xaa is Arg, Glu, Lys or citrulline which may be
      derivatized at the C-terminal.

<400> SEQUENCE: 73

Xaa Xaa Xaa Cys Tyr Xaa Xaa Xaa Xaa Xaa Xaa Xaa Cys Xaa
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic formula peptide
<220> FEATURE:
<221> NAME/KEY: MISC_FEATURE
<222> LOCATION: (1)..(1)
<223> OTHER INFORMATION: Xaa is Arg, Ala or Citrulline
<220> FEATURE:
<221> NAME/KEY: MISC_FEATURE
<222> LOCATION: (3)..(3)
<223> OTHER INFORMATION: Xaa is Trp or naphtylalanine
<220> FEATURE:
<221> NAME/KEY: MISC_FEATURE
<222> LOCATION: (6)..(6)
<223> OTHER INFORMATION: Xaa is Arg, Ala or Citrulline
<220> FEATURE:
<221> NAME/KEY: MISC_FEATURE
<222> LOCATION: (7)..(7)
<223> OTHER INFORMATION: Xaa is Lys, Ala or Citrulline
<220> FEATURE:
<221> NAME/KEY: MISC_FEATURE
<222> LOCATION: (8)..(9)
<223> OTHER INFORMATION: These positions represent a dipeptide selected
      from: D-lysyl-proline, D-alanyl-proline, D-lysyl-alanine and
      D-citrullyl-proline
<220> FEATURE:
<221> NAME/KEY: MISC_FEATURE
<222> LOCATION: (10)..(10)
<223> OTHER INFORMATION: Xaa is Tyr or Ala
```

-continued

```
<220> FEATURE:
<221> NAME/KEY: MISC_FEATURE
<222> LOCATION: (11)..(11)
<223> OTHER INFORMATION: Xaa is Arg, Ala or Citrulline
<220> FEATURE:
<221> NAME/KEY: MISC_FEATURE
<222> LOCATION: (12)..(12)
<223> OTHER INFORMATION: Xaa is Citrulline

<400> SEQUENCE: 74

Xaa Arg Xaa Cys Tyr Xaa Xaa Xaa Xaa Xaa Xaa Xaa Cys Arg
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic formula peptide
<220> FEATURE:
<221> NAME/KEY: MISC_FEATURE
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: D-citrulline, D-alanine, citrulline or alanine
<220> FEATURE:
<221> NAME/KEY: MISC_FEATURE
<222> LOCATION: (9)..(9)
<223> OTHER INFORMATION: Tyr, Phe, Ala, naphthylalanine or citrulline
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (11)..(11)
<223> OTHER INFORMATION: citrulline
<220> FEATURE:
<221> NAME/KEY: MISC_FEATURE
<222> LOCATION: (13)..(13)
<223> OTHER INFORMATION: Lys or Arg; a carboxyl group may be amidated

<400> SEQUENCE: 75

Xaa Arg Xaa Cys Tyr Xaa Xaa Xaa Xaa Xaa Xaa Cys Xaa
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic formula peptide
<220> FEATURE:
<221> NAME/KEY: MISC_FEATURE
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: MISC_FEATURE
<222> LOCATION: (1)..(14)
<223> OTHER INFORMATION: this sequence is structured with the proviso
      that either of the amino acid residues at positions 1, 6, 7, 10,
```

11 and 14 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: DISULFID
<222> LOCATION: (4)..(13)
<223> OTHER INFORMATION: Cys at 4-position and Cys at 13-position may
      form a disulfid bond.
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(9)
<223> OTHER INFORMATION: D-orn-pro, pro-D-orn, D-lys-pro, pro-D-lys,
      D-arg-pro, pro-D-arg, D-cit-pro, D-cit-ala, D-ala-cit, pro-D-cit,
      gly-orn, orn-gly, gly-lys, lys-gly, gly-arg, arg-gly, gly-cit,
      cit-gly, D-ala-pro or D-lys-ala
<220> FEATURE:
<221> NAME/KEY: MISC_FEATURE
<222> LOCATION: (10)..(10)
<223> OTHER INFORMATION: Tyr, Phe, Ala, naphthylalanine or citrulline
<220> FEATURE:
<221> NAME/KEY: MISC_FEATURE
<222> LOCATION: (11)..(11)
<223> OTHER INFORMATION: Arg, Lys, Ala, ornithine or citrulline
<220> FEATURE:
<221> NAME/KEY: MISC_FEATURE
<222> LOCATION: (14)..(14)
<223> OTHER INFORMATION: Lys or Arg; a carboxyl group may be amidated

<400> SEQUENCE: 76

Xaa Arg Xaa Cys Tyr Xaa Xaa Xaa Xaa Xaa Xaa Xaa Cys Xaa
1               5                   10

<210> SEQ ID NO 77
<211> LENGTH: 18
<212> TYPE: PRT
<213> ORGANISM: Artificial Sequence
<220> FEATURE:
<223> OTHER INFORMATION: Synthetic formula peptide
<220> FEATURE:
<221> NAME/KEY: MISC_FEATURE
<222> LOCATION: (1)..(1)
<223> OTHER INFORMATION: Arg, Lys, Ala, ornithine, citrulline, any
      N-alpha-substituted derivative of these amino acids, or not
      present
<220> FEATURE:
<221> NAME/KEY: MISC_FEATURE
<222> LOCATION: (1)..(18)
<223> OTHER INFORMATION: this sequence is structured with the proviso
      that either of the amino acid residues at positions 1, 6, 7, 14,
      15 and 18 is Ala or citrulline
<220> FEATURE:
<221> NAME/KEY: MISC_FEATURE
<222> LOCATION: (3)..(3)
<223> OTHER INFORMATION: Any aromatic amino acid
<220> FEATURE:
<221> NAME/KEY: DISULFID
<222> LOCATION: (4)..(17)
<223> OTHER INFORMATION: Cys at 4-position and Cys at 17-position may
      form a disulfid bond.
<220> FEATURE:
<221> NAME/KEY: MISC_FEATURE
<222> LOCATION: (6)..(7)
<223> OTHER INFORMATION: Each position independently represents Arg,
      Lys, Ala, ornithine or citrulline
<220> FEATURE:
<221> NAME/KEY: MISC_FEATURE
<222> LOCATION: (8)..(8)
<223> OTHER INFORMATION: Ala, Val, Leu, Ile, Ser, Cys or Met
<220> FEATURE:
<221> NAME/KEY: DISULFID
<222> LOCATION: (8)..(13)

```
<223> OTHER INFORMATION: when positions 8 and 13 are Cys, they may form
      a disulfide bond
<220> FEATURE:
<221> NAME/KEY: MISC_FEATURE
<222> LOCATION: (9)..(9)
<223> OTHER INFORMATION: Any aromatic amino acid
<220> FEATURE:
<221> NAME/KEY: MISC_FEATURE
<222> LOCATION: (10)..(10)
<223> OTHER INFORMATION: Arg, Lys, Ala, ornithine or citrulline
<220> FEATURE:
<221> NAME/KEY: MISC_FEATURE
<222> LOCATION: (12)..(12)
<223> OTHER INFORMATION: Tyr, Phe, Trp, Ala, Val, Leu, Ile, Ser, Cys or
      Met
<220> FEATURE:
<221> NAME/KEY: MISC_FEATURE
<222> LOCATION: (13)..(13)
<223> OTHER INFORMATION: Ala, Val, Leu, Ile, Ser, Cys or Met

<400> SEQUENCE: 77

Xaa Arg Xaa Cys Tyr Xaa Xaa Xaa Xaa Xaa Gly Xaa Xaa Xaa Xaa Xaa
1               5                   10                  15

Cys Xaa
```

The invention claimed is:

1. A method for obtaining a therapeutically effective amount of hematopoietic precursor cells from a subject, comprising:
   a) administering to the subject an effective amount of a peptide having the amino acid sequence as set forth in SEQ ID NO:1;
   b) harvesting said precursor cells by apheresis; and optionally
   c) repeating steps (a) and (b) until a therapeutically effective amount of hematopoietic precursor cells is obtained, wherein said method does not comprise administering G-CSF.

2. A method for obtaining long-term engraftment of hematopoietic precursor cells, comprising:
   (a) administering to a first subject an effective amount of a peptide having the amino acid sequence as set forth in SEQ ID NO:1;
   (b) harvesting said precursor cells by apheresis;
      optionally repeating steps (a) and (b) until a therapeutically effective amount of hematopoietic precursor cells is obtained; and
   (c) transplanting the resulting cells to the first subject or to a second subject in need thereof, wherein said method does not comprise administering G-CSF.

* * * * *